United States Patent
Peyman et al.

Patent Number: 6,127,346
Date of Patent: Oct. 3, 2000

[54] PHOSPHONOMONOESTER NUCLEIC ACIDS PROCESS FOR THEIR PREPARATION AND THEIR USE

[75] Inventors: Anuschirwan Peyman, Kelkheim; Eugen Uhlmann, Glashütten; Gerhard Breipohl, Frankfurt; Holger Wallmeier, Sulzbach, all of Germany

[73] Assignee: Hoechst Aktiengesellschaft, Frankfurt am Main, Germany

[21] Appl. No.: 09/196,132

[22] Filed: Nov. 20, 1998

Related U.S. Application Data

[63] Continuation of application No. 08/613,417, Mar. 11, 1996, Pat. No. 5,874,553.

[30] Foreign Application Priority Data

Mar. 13, 1995 [DE] Germany .............. 195 08 923
Nov. 24, 1995 [DE] Germany .............. 195 43 865

[51] Int. Cl.[7] .............. A01N 43/04; C12Q 1/70; C12Q 1/68; C07H 19/00; C07H 21/02
[52] U.S. Cl. .............. 514/44; 514/1; 435/5; 435/6; 536/22.1; 536/23.1; 536/24.3; 536/25.3; 536/25.32
[58] Field of Search .............. 435/5, 6; 536/22.1, 536/23.1, 24.3, 25.3, 25.32; 514/1, 44

[56] References Cited

U.S. PATENT DOCUMENTS

| | | | |
|---|---|---|---|
| 4,344,949 | 8/1982 | Hoefle et al. | 424/258 |
| 4,350,704 | 9/1982 | Hoefle et al. | 424/274 |
| 4,374,847 | 2/1983 | Gruenfeld | 424/274 |
| 5,166,394 | 11/1992 | Breipohl et al. | 558/301 |
| 5,264,562 | 11/1993 | Matteucci | 536/23.1 |

FOREIGN PATENT DOCUMENTS

| | | |
|---|---|---|
| 2087818 | 7/1993 | Canada . |
| 2165971A | 1/1995 | Canada . |
| 2144475 | 9/1995 | Canada . |
| 0 460 446 B1 | 12/1991 | European Pat. Off. . |
| 0 552 766 A2 | 7/1993 | European Pat. Off. . |
| 0 672 677 A2 | 9/1995 | European Pat. Off. . |
| 4321946A1 | 1/1995 | Germany . |
| 44 08 528 A1 | 9/1995 | Germany . |
| WO 94/22864 | 10/1994 | WIPO . |
| WO 94/22891 | 10/1994 | WIPO . |
| WO 95/11911 | 5/1995 | WIPO . |

*Primary Examiner*—Jezia Riley
*Attorney, Agent, or Firm*—Finnegan, Henderson, Farabow, Garrett & Dunner, L.L.P.

[57] ABSTRACT

Novel oligonucleotide analogs of the formula [I] are described,

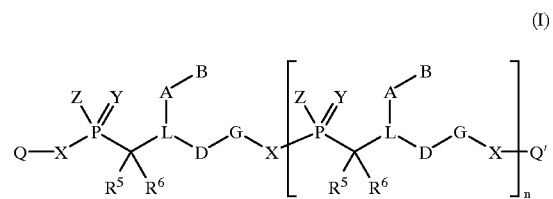

in which A, B, D, G, L, P, Q, Q', $R^5$, $R^6$, X, Y, Z and n are as defined in the description, which have useful physical, biological and pharmacological properties, as well as a process for their preparation. Their application relates to use as inhibitors of gene expression (antisense oligonucleotides, ribozymes, sense oligonucleotides and triplex-forming oligonucleotides), as probes for the detection of nucleic acids and as auxiliaries in molecular biology.

6 Claims, 2 Drawing Sheets

PHOSPHONOMONOESTER NUCLEIC ACIDS PROCESS FOR THEIR PREPARATION AND THEIR USE

This is a continuation of application Ser. No. 08/613,417, filed Mar. 11, 1996, now U.S. Pat. No. 5,874,553, which is incorporated herein by reference.

The present invention relates to novel oligonucleotide analogs having useful physical, biological and pharmacological properties, and to a process for their preparation. Their application relates to use as inhibitors or gene expression (antisense oligonucleotides, ribozymes, sense oligonucleotides and triplex-forming oligonucleotides), as probes for the detection of nucleic acids and as auxiliaries in molecular biology.

The disclosure of all documents referred to in this specification are incorporated in whole by reference.

Oligonucleotides are applied to a growing extend as inhibitors of gene expression (J. F. Milligan, M. D. Matteucci and J. C. Martin, J. Med. Chem. 36 (1993) 1923; E. Uhlmann and A. Peyman, Chemical Reviews 90 (1990) 543; S. T. Crooke, Annu. Rev. Pharmacol. Toxicol. 32 (1992) 329).

Antisense oligonucleotides are nucleic acid fragments whose base sequence is complementary to an mRNA to be inhibited. This target mRNA can be of cellular, viral or other pathogenic origin. Possible cellular target sequences are, for example, those of receptors, enzymes, growth factors, immunomodulators, ion channels or oncogenes. The inhibition of virus replication with the aid of antisense oligonucleotides was described, for example, for RSV (rous sarcoma virus), HSV-1 and -2 (herpes simplex virus type I and II), HIV (human immunodeficiency virus) and influenza viruses. In this case, oligonucleotides are employed which are complementary to the viral nucleic acid.

The sequence of sense oligonucleotides is designed, however, such that they bind ("capture"), for example, nucleic acid-binding proteins or nucleic acid-processing enzymes and thus inhibit their biological activity (C. Hélène and J. J. Toulmé, Biochim. Biophys. Acta 1049 (1990) 99). Viral targets which may be mentioned here are, for example, reverse transcriptase, DNA polymerase and transactivator proteins. In general, triplex-forming oligonucleotides have DNA as a target and, after binding to this, form a triple helical structure.

Whereas with the aid of the antisense oligonucleotides, the processing (splicing etc.) of the mRNA or its translation into the protein are in general inhibited, triplex-forming oligonucleotides inhibit the transcription or replication of the DNA (N. T. Thuong, and C. Hélène, Angew. Chem. 105 (1993) 697; Uhlmann and Peyman, Chemical Reviews 90 (1990) 543). However, it is also possible to bind single-stranded nucleic acids with an antisense oligonucleotide in a first hybridization with formation of a double strand, which then forms a triplex structure in a second hybridization with a triplex-forming oligonucleotide. The antisense and triplex-binding regions can in this case either be accommodated in two separate oligonucleotides or else in one oligonucleotide.

A further application of synthetic oligonucleotides are the so-called ribozymes, which destroy the target RNA as a result of their ribonuclease activity (D. Castanotto, J. J. Rossi, J. O. Deshler, Critical Rev. Eukar. Gene Expr. 2 (1992) 331).

In DNA diagnosis, nucleic acid fragments with suitable labelling are employed as so-called DNA probes for the specific hybridization of a nucleic acid to be detected. The specific formation of the new double strand is in this case monitored with the aid of the labelling, which is preferably not radioactive. In this manner, genetic, malignant, viral or other pathogen-caused diseases can be detected.

For most applications mentioned, oligonucleotides in their naturally occurring form are not very suitable or completely unsuitable. They must be chemically modified such that they meet the specific requirements. In order that oligonucleotides can be employed in biological systems, for example for the inhibition of virus replication, they must fulfill the following requirements:

1. They must have a sufficiently high stability under in vivo conditions, i.e. both in serum and intracellularly.
2. They must be constituted such that they can pass through the cell and nucleus membrane.
3. They must bind to their target nucleic acid in base-specific manner under physiological conditions in order to display the inhibitory effect.

These requirements are not indispensable for DNA probes; however, these oligonucleotides must be derivatized such that detection is possible, for example by means of fluorescence, chemiluminescence, colorimetry or specific staining (Beck and Köster, Anal. Chem. 62 (1990) 2258).

A multiplicity of chemical variations of oligonucleotides are known which have been synthesized with the aim of fulfilling the abovementioned requirements better than the unmodified oligonucleotides. The chemical modification of the oligonucleotides is usually carried out by appropriately modifying the phosphate backbone, ribose unit or the nucleobases (Uhlmann and Peyman, Chemical Review 90 (1990) 543). The modifications also include those in which both the phosphate bridge and the sugar unit have been replaced by other groups, for example by "morpholino-nucleoside" oligomers (E. P. Stirchak et al., Nucleic Acids Res. 17 (1989) 6129) or "PNAs" (P. E. Nielsen et al, Bioconj. Chem. 5 (1994) 3). PNAs, in particular, are distinguished by unusually high affinities for target RNA, but suffer from other unfavorable properties such as lack of solubility or deficient cell penetration (W. Wang et al., Tetrahedron Letters 36 (1995) 1181; M. Egholm et al., in "Innovation and Perspectives in Solid Phase Synthesis, Peptides, Proteins, Nucleic Acids", Roger Epton, Ed. Mayflower Worldwide Limited, Birmingham, 1994, 145–148).

It is therefore an object to find novel oligonucleotide analogs having favorable properties.

Figure 1:
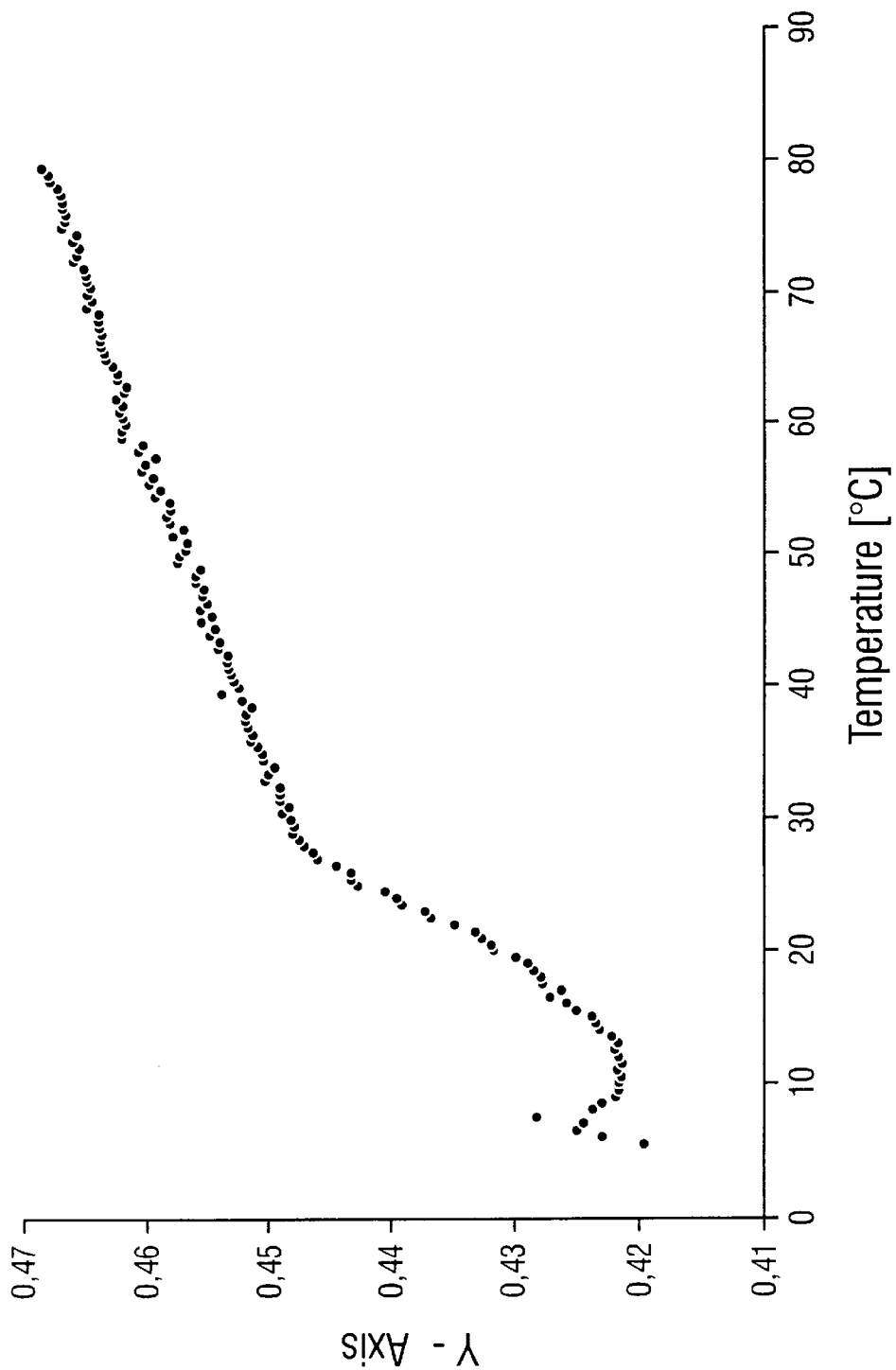
FIG. 1 is a graph showing a UV-Absorbance Profile Versus Temperature for [pmena-t9] in the Presence of 1 eq. dA9 [See Example 56].

The invention therefore relates to compounds of the formula I

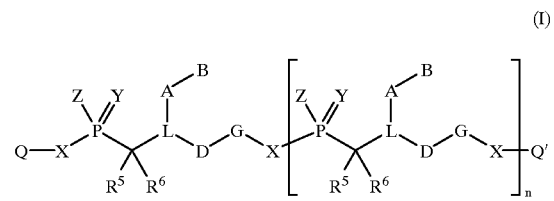

wherein n is a number from zero to 100;

B independently of one another is hydrogen, hydroxyl, $(C_1-C_{20})$-alkyl, $(C_1-C_{20})$-alkoxy, $(C_1-C_{20})$-alkylthio, $(C_6–C_{20})$-aryl, $(C_6–C_{20})$-aryl-$(C_1–C_6)$-alkyl, $(C_6–C_{20})$-aryl-$(C_1–C_6)$-alkoxy, $(C_6–C_{20})$-aryl-$(C_1–C_6)$-alkylthio, an aromatic group or a heterocyclic group, where alkyl, aryl, the aromatic or a heterocyclic group, where alkyl, aryl, the aromatic or heterocyclic group can optionally be substituted one or more times by hydroxyl, $(C_1–C_4)$-alkoxy, —$NR^9R^{10}$, —C(O)OH, oxo, —$C(O)R^8$, —$C(O)NR^9R^{10}$, —CN, —F, —Cl, —Br, —$NO_2$, $(C_2–C_6)$-alkoxyalkyl, —$S(O)_mR^8$, -$(C_1–C_6)$-alkyl- $S(O)_mR_8$, —$NHC(=NH)NHR^8$, —$C(=NH)NHR^8$, —$NR^9C(=O)R^8$, =$NOR^8$, $NR^9C(=O)OR^{10}$, —$OC(=O)NR^9R^{10}$ or —$NR^9C(=O)NR^9R^{10}$, m is zero, 1 or 2

B independently of one another is a natural nucleobase, an unnatural nucleobase or a reporter ligand; and A-B can also be a D- or L-amino acid condensed on via the carboxyl group or peptides consisting of these amino acids having a length of up to 5 amino acid residues, L independently of one another is N or $R^1N^+$, and $R^1$ is hydrogen or $(C_1–C_6)$-alkyl which can be substituted by hydroxyl, $(C_1–C_6)$-alkoxy, $(C_1–C_6)$-alkylthio or amino. Preferably, $R^1$ is hydrogen or methyl;

A independently of one another is a single bond, a methylene group or a group of the formula IIa or IIb;

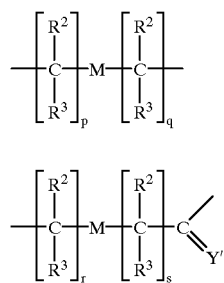

(IIa)

(IIb)

Y' is =O, =S, =$CH_2$, =$C(CH_3)_2$ or =$NR^1$, where $R^1$ is as defined above;

M is a single bond, —O—, —S— or —$NR^1$—, where $R^1$ is as defined above;

$R^2$ and $R^3$ independently of one another are hydrogen, hydroxyl, $(C_1–C_6)$-alkoxy, $(C_1–C_6)$-alkylthio, amino, halogen, such as F, Cl or Br, or $(C_1–C_6)$-alkyl which can optionally be substituted by hydroxyl, $(C_1–C_6)$-alkoxy or $(C_1–C_6)$-alkylthio, but are preferably hydrogen;

p and q independently of one another are zero to 5;

r and s independently of one another are zero to 5;

D and G each represent $CR^5R^6$ which can be the same or different;

$R^5$ and $R^6$ independently of another are hydrogen, $(C_1–C_6)$-alkyl, $(C_6–C_{20})$-aryl, $(C_6–C_{20})$-aryl-$(C_1–C_6)$-alkyl, hydroxyl, $(C_1–C_6)$-alkoxy, $(C_1–C_6)$-alkylthio, and alkyl and aryl can optionally be substituted by $SR^1$ or $NR^1R^{1'}$, where $R^{1'}$ is as defined above and $R^{1'}$ independently or $R^1$ has the same meaning as $R^1$, but $R^5$ and $R^6$ are preferably hydrogen;

X is —O—, —S— or —$NR^1$—, in which $R^1$ is as defined above;

Y is =O or =S;

Z is —$OR^8$, —$NR^9R^{10}$ or X'Q", where X' is defined as X and Q" is defined as Q;

$R^8$ is hydrogen, $(C_1–C_{18})$-alkyl, $(C_2–C_{18})$-alkenyl, $(C_1–C_{18})$-alkynyl, $(C_6–C_{12})$-aryl, $(C_6–C_{12})$-aryl-$(C_1–C_6)$-alkyl, where alkyl can be substituted one or more times by hydroxyl, $(C_1–C_4)$-alkoxy, F, Cl or Br and aryl can be substituted 1–3 times by hydroxyl, $(C_1–C_4)$-alkoxy, $(C_1–C_4)$-alkyl, F, Cl, Br, $NO_2$, —$NR^9R^{10}$, —C(O)OH, —C(O)O—$(C_1–C_6)$-alkyl or —$C(O)NR^9R^{10}$, but preferably $R^8$ is hydrogen, $(C_1–C_4)$-alkyl, $(C_6–C_{12})$-aryl or $(C_6C_{12})$-aryl-$(C_1–C_6)$-alkyl, where aryl can be monosubstituted by $(C_1–C_4)$-alkoxy, $(C_1–C_4)$-alkyl, F, Cl, Br or $NO_2$. More preferably $R^8$ is hydrogen, $(C_1–C_6)$-alkyl, phenyl or 2-(4-nitrophenyl)ethyl;

$R^9$ and $R^{10}$ independently of one another are hydrogen, $(C_1–C_{18})$-alkyl, $(C_1–C_{18})$-alkenyl, $(C_1–C_{18})$-alkynyl, $(C_6–C_{12})$-aryl, $(C_6–C_{12})$-aryl-$(C_1–C_6)$-alkyl, where alkyl can be substituted one or more times by hydroxyl, $(C_1–C_4)$-alkoxy, F, Cl, or Br, or $R^9$ and $R^{10}$ can together form a 4 to 7-membered ring together with the N atom carrying them;

Q and Q' independently of one another are hydrogen or $R^8$.

Alternatively, Q and Q' are conjugates which a) favorably affect the properties of antisense oligonucleotides, b) affect the properties of triple helix-forming oligonucleotides, c) serve as a label of a DNA probe, d) during the hybridization of the oligonucleotide analog to the target nucleic acid, attack the target nucleic acid through binding or crosslinking. Or, Q and Q' are oligonucleotides which can be unmodified or modified, where the following variants are intended to be examples of some modifications (e.g. described in E. Uhlmann and A. Peyman, Chemical Reviews 90 (1990) 543; "Protocols for Oligonucleotides and Analogs", Synthesis and Properties & Synthesis and Analytical Techniques, S. Agrawal, Ed. Humana Press, Totowa, USA (1993):

a) complete or partial replacement of the 3'-and/or the 5'-phosphoric acid diester bridges, for example by phosphorothioate, phosphorodithioate, $NR^4R^{4'}$-phosphoramidate, boranophosphate, phosphate-$(C_1–C_{21})$-O-alkyl ester, phosphate-[$(C_6–C_{12})$aryl-$(C_1–C_{21})$-O-alkyl] ester, 2,2,2-trichlorodimethylethylphosphonate, $(C_1–C_8)$ alkylphosphonate or $(C_6–C_{12})$-arylphosphonate bridges, where $R^4$ and $R^{4'}$ independently of one another are hydrogen, $(C_1–C_{18})$-alkyl, $(C_6–C_{20})$-aryl, $(C_6–C_{14})$-aryl-$(C_1–C_8)$-alkyl or —$(CH_2)_c$-[$NH(CH_2)_c$]$_d$-$NR^7R^7$, in which c is an integer from 2 to 6 and d is an integer from 0 to 6, and $R^7$ independently of one another is hydrogen, $(C_1–C_6)$-alkyl or $(C_1–C_4)$-alkoxy-$(C_1–C_6)$-alkyl, preferably $R^4$ and $R^{4'}$ are hydrogen, $(C_1–C_8)$-alkyl or methoxyethyl, particularly preferably hydrogen, $(C_1–C_4)$-alkyl or methoxyethyl or $R^4$ and $R^{4'}$, together with the nitrogen atom carrying them, can also form a 5 to 6-membered heterocyclic ring which can additionally contain a further heteroatom from the series consisting of O, S and N;

b) complete or partial replacement of the 3'- or 5'-phosphoric acid diester bridges by "dephospho" bridges (see, for example, Uhlmann and Peyman in "Methods in Molecular Biology", Vol. 20, "Protocols for Oligonucleotides and Analogs", S. Agrawal, Ed., Humana Press, Totowa 1993, Chapter 16, 355ff), for example by formacetal, 3'-thioformacetal, methylhydroxylamine, oxime, methylenedimethylhydrazo, dimethylenesulfone or silyl groups;

c) complete or partial replacement of the sugar phosphate backbone, for example by "morpholinonucleoside" oligomers (E. P. Stirchak et al., Nucleic Acids Res. 17 (1989) 6129) or "PNAs" (P. E. Nielsen et al, Bioconj. Chem. (1994) 3), or PNA-DNA hybrids such as described, for example, in DE-P 44 08 528.1 and EP-A 0 672 677;

d) complete or partial replacement of the β-D-2'-deoxyribose units, for example by α-D-2'-deoxyribose, L-2'-deoxyribose, 2'-F-2'-deoxyribose, 2'-O-($C_1$–$C_6$) alkyl- ribose, 2'-O-($C_2$–$C_6$)alkenylribose, 2'-$NH_2$-2'-deoxyribose, β-D-xylofuranose, α-arabinofuranose, 2,4-dideoxy-β-D-erythrohexopyranose, and carbocyclic (e.g. Froehler, J.Am.Chem.Soc. 114 (1992) 8320) and open-chain sugar analogs (e.g. Vandendriessche et al., Tetrahedron 49 (1993) 7223) or bicyclo sugar analogs (e.g. M. Tarkov et al., Helv. Chim. Acta 76 (1993) 481);

e) complete or partial replacement of the natural nucleoside bases, for example by 5-(hydroxymethyl)uracil, 5-aminouracil, pseudouracil, dihydrouracil, 5-($C_2$–$C_6$)-alkynyluracil (for example described in Gutierrez et al., J. Am. Chem. Soc. 116 (1994) 540 or Sagi et al., Tetrahedron Lett. 34 (1993) 2191), 5-($C_1$–$C_6$)-alkylcytosine, 5-($C_2$–$C_6$)-alkenylcytosine, 5-($C_2$–$C_6$)-alkynylcytosine (Gutierrez et al., J. Am. Chem. Soc. 116 (1994) 540 or Sagi et al., Tetrahedron Lett. 34 (1993) 2191), 5-fluorouracil, 5-fluorocytosine, 5-chlorouracil, 5-chlorocytosine, 5-bromouracil, 5-bromocytosine or 7-deaza-7-substituted purines (for example described in Seela, Nucl. Acids Res. 20 (1992) 2297); Heterocycles 34 (1992) 229).

Q and Q' can also be conjugates which favorably affect the properties of antisense oligonucleotides or of triple helix-forming oligonucleotides (such as, for example, cell penetration, nuclease degradation, affinity for the target RNA/DNA, pharmacokinetics) or serve as a label of a DNA probe or during the hybridization of the oligonucleotide analog to the target nucleic acid, attacking the target nucleic acid through binding or crosslinking. Examples of these are conjugates with polylysine, with intercalators such as pyrene, acridine, phenazine, phenanthridine, with fluorescent compounds such as fluorescein, with crosslinkers such as psoralen, azidoproflavine, with lipophilic molecules such as ($C_{12}$–$C_{20}$)-alkyl, with lipids such as 1,2-dihexadecyl-rac-glycerol, with steroids such as cholesterol or testosterone, with vitamins such as vitamin E, with poly- or oligoethylene glycol, with ($C_{12}$–$C_{18}$)-alkyl phosphate diesters, with —O—$CH_2$—CH(OH)—O–($C_{12}$–$C_{18}$)-alkyl. Preferred conjugates are those with lipophilic molecules such as ($C_{12}$–$C_{20}$)-alkyl, with steroids such as cholesterol or testosterone, with poly- or oligoethylene glycol, with vitamin E, with intercalators such as pyrene, with ($C_{14}$–$C_{18}$)-alkylphosphate diesters or with —O—$CH_2$—CH(OH)—O–($C_{12}$–$C_{16}$)-alkyl.

The preparation of oligonucleotide conjugates of this type is known to the person skilled in the art (see, for example, Uhlmann & Peyman, Chem. Rev. 90 (1990) 543; M. Manoharan in "Antisense Research and Applications", Crooke and Lebleu, Eds., CRC Press, Boca Raton, 1993, Chapter 17, p. 303ff and EP-A 0 552 766). Furthermore, the oligonucleotides can carry 3'-3'-and 5'-5'-inversions on the 3' or on the 5'-end (described, for example, in M. Koga et al., J. Org. Chem. 56 (1991) 3757).

Aromatic groups are, for example, phenyl, naphthyl, pyrenyl, anthracenyl, phenanthryl, biphenyl, binaphthyl, tetracenyl, pentacenyl, hexacenyl, triphenylenyl, chrysenyl or benzopyrenyl.

Heterocyclic groups are understood as meaning, for example, chromanyl, chromenylium-1-yl, furanyl, isochromanyl, isochromenyl, isoquinolyl, piperazinyl, quinolinyl, pyridinyl, pyrrolidinyl, imidazolyl, tetrahydrofuranyl, aziridinyl, oxiranyl, thiophenyl, pyrimidinyl, thiolanyl, thiazolyl, azepinyl, pyrrolyl, tetrahydropyrrolyl, benzofuranyl, indolyl, isoindolyl, isatinyl, dioxindolyl, indoxylyl, coumarinyl, coumaronyl, carbazolyl, pyrazolyl, pyrrolyl, indazolyl, oxazolyl, isoxazolyl, thiazolyl, 1,2,4-triazolyl, 1,2,3-triazolyl, tetrazolyl, pentazolyl, piperidinyl, pyridazinyl, phenazinyl, phenoxazinyl, pyenothiazinyl, morpholinyl, thiazinyl, benzodiazepinyl, purinyl, xanthinyl, hypoxanthinyl, theophyllinyl, theobrominyl, caffeinyl, pteridinyl, pterinyl, pteridinyl, alloxazinyl and nortropinyl.

Natural nucleobases are understood as meaning, for example, uracil, cytosine, 5-methyluracil, adenine and guanine and unnatural nucleobases are understood as meaning, for example, 5-nitroindole, 5-(hydroxymethyl)-uracil, 5-aminouracil, pseudouracil, dihydrouracil, 5-($C_1$–$C_6$)-alkyluracil, 5-($C_2$–$C_6$)-alkenyluracil, 5-($C_3$–$C_6$)-alkynyluracil, 5-($C_1$–$C_6$)-alkylcytosine, 5-($C_2$–$C_6$)-alkenylcytosine, 5-($C_3$–$C_6$)-alkynylcytosine, 5-fluorouracil, 5-fluorocytosine, 5-chlorouracil, 5-chlorocytosine, 5-bromouracil, 5-bromocytosine and 7-deaza-7-substituted purines, such as 7-deaza-7-($C_3$–$C_7$)-alkynylguanine, 7-deaza-7-($C_3$–$C_7$)-alkynyladenine, 7-deaza-7-($C_2$–$C_7$)-alkenylguanine, 7-deaza-7-($C_2$–$C_7$)-alkenyladeine, 7-deaza-7-($C_1$–$C_7$)-alkylguanine, 7-deaza-7-($C_1$–$C_7$)-alkyladenine, 7-deaza-7-bromoguanine and 7-deaza-7-bromoadenine.

Preferably, unnatural nucleobases are 5-($C_1$–$C_6$)-alkyluracil, 5-($C_2$–$C_6$)-alkenyluracil, 5-($C_3$–$C_6$)-alkynyluracil, 5-($C_1$–$C_6$)-alkylcytosine, 5-($C_2$–$C_6$)-alkenylcytosine, 5-($C_3$–$C_6$)-alkynylcytosine, 5-chlorocytosine, 5-bromo-uracil, 5-bromocytosine or 7-deaza-7-substituted purines such as 7-deaza-7-($C_3$–$C_7$)-alkynylguanine, 7-deaza-7-($C_3$–$C_7$)-alkynyladenine, 7-deaza-7-($C_2$–$C_7$)-alkenylguanine, 7-deaza-7-($C_2$–$C_7$)-alkenyladenine, 7-deaza-7-($C_2$–$C_7$)-alkenyladeine, 7-deaza-7-($C_1$–$C_7$)-alkylguanine, 7-deaza-7-($C_1$–$C_7$)-alkyladenine, 7-deaza-7-bromoguanine and 7-deaza-7-bromoadenine, particularly preferably 5-($C_3$–$C_6$)-alkyluracil, 5-($C_2$–$C_6$)-alkenyl-uracil, 5-($C_3$–$C_6$)-alkynyluracil, 5-($C_1$–$C_6$)-alkylcytosine 5-($C_2$–$C_6$)-alkenylcytosine, 5-($C_3$–$C_6$)-alkynylcytosine or 7-deaza-7-substituted purines, and very particularly preferably 5-pentynylcytosine, 5-hexynyluracil, 5-hexynylcytosine, 7-deaza-7-propynylguanine, 7-deaza-7-propynylcytosine, 7-deaza-7-methylguanine, 7-deaza-7-methyladenine, 7-deaza-7-propynyladenine, 7-deaza-7-bromoguanine, 7-deaza-7-bromoadenine.

Reporter ligands are, for example, fluorescein, biotin, acridine, phenanthroline, phenanthridine and eosin.

Among D- or L-amino acids, if not stated otherwise, particularly the following may be mentioned (cf. Schröder, Lübke, Peptides, Volume 1, New York 1965, pages XXI-I–XXIII; Houben-Weyl, Methoden der Organischen Chemie, [Methods of Organic Chemistry] Volume XV/1 and 2, Stuttgart 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, hArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val etc., whose abbreviations without a stereo- descriptor stand for the radical in the L-form, and cyclic amino acids, such as pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid;

octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro[(bicyclo[2.2.1]heptane)-2,3-pyrrolidine-5-carboxylic acid]; spiro[(bicyclo[2.2.2]octane)-2,3-pyrrolidine-5-carboxylic acid]; 2-azatricyclo[4.3.0.1$^{6,9}$]decane-3-carboxylic acid; decahydrocyclohepta[b]pyrrole-2-carboxylic acid; decahydrocycloocta[b]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxypyrrolidine-2-carboxylic acid; all of which can be optionally substituted with:

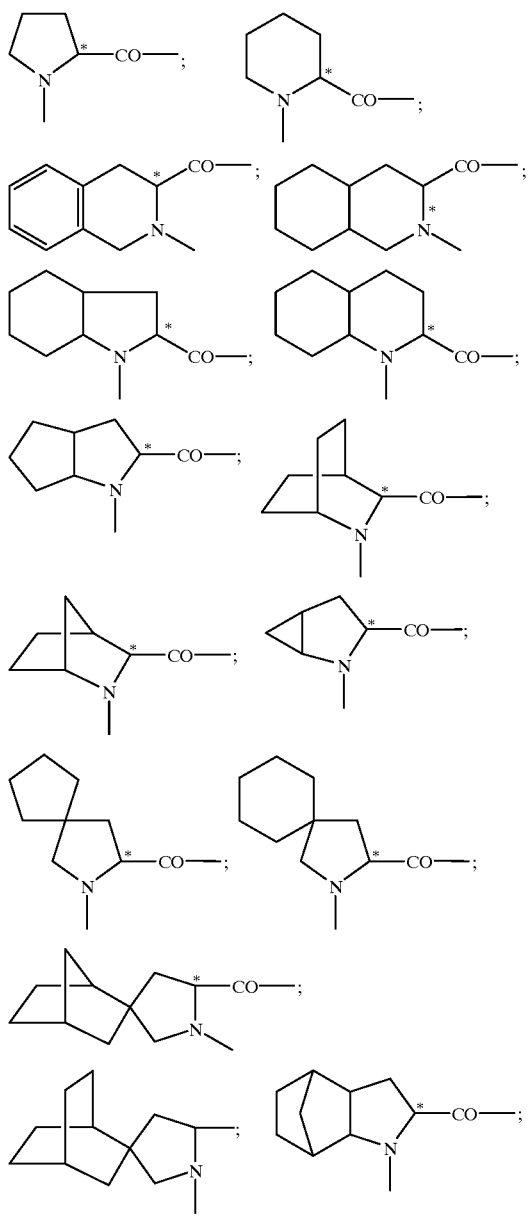

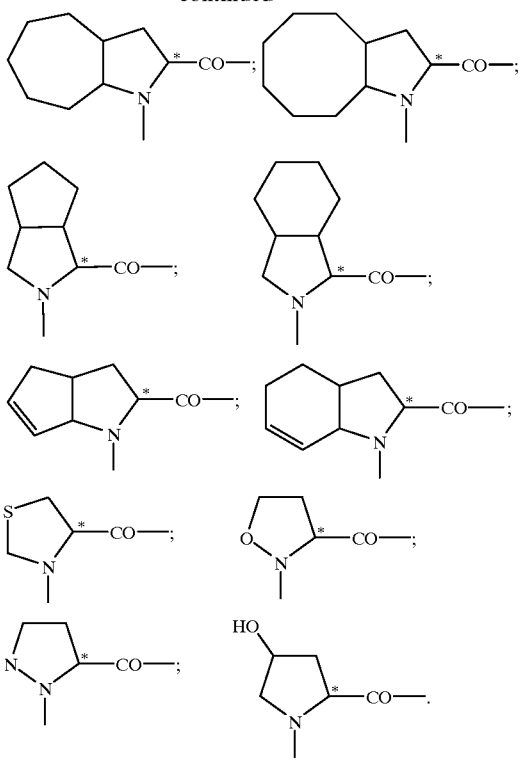

U.S. Pat. Nos. 4,344,949, 4,374,847 and 4,350,704, and EP-A 29 488, EP-A 31 741, EP-A 46 953, EP-A 49 605, EP-A 49 658, EP-A 50 800, EP-A 51 020, EP-A 52 870, EP-A 79 022, EP-A 84 164, EP-A 89 637, EP-A 90 341, EP-A 90 362, EP-A 105 102, EP-A 109 020, EP-A 111 873, EP-A 271 865 and EP-A 344 682 describe cyclic amino acids.

In formula I even when n is greater than 1, the substitutions can be the same or different from each other.

Alkyl and radicals derived therefrom such as alkoxy and alkylthio can be branched, unbranched or cyclic, saturated or mono- or polyunsaturated.

Preferred compounds of the formula I are those wherein n is a number from zero to 50;

B independently of one another is a natural nucleobase or an unnatural nucleobase;

L is N;

A is a group of the formula IIB, in which r=1 and s is zero, and $R^2$, $R^3$=H and Y'=O and M is a single bond;

D and G each independently represent $CHR^5$;

$R^5$ is hydrogen;

X is —O—;

Y is =O;

Z is hydroxyl, methoxy, ethoxy, (4-nitrophenyl)ethoxy, propoxy, isopropoxy, butoxy, pentoxy, phenoxy or allyloxy;

Q and Q' independently of one another are hydrogen, $R^8$ or oligonucleotides unmodified or modified, as follows:

a) the 3'- and/or 5'-phosphoric acid diester bridges are completely or partially replaced by phosphorothioate, phosphorodithioate, $NR^4R^{4'}$-phosphoramidate, N3'-P5'-phosphoramidate (for example described in Gryaznov et al., J. Am. Chem. Soc. 116 (1994) 3143), phosphate O-methyl ester, phosphate O-ethyl ester, phosphate O-isopropyl ester, methylphosphonate or phenylphosphonate bridges;

b) one, two or three 3'- or 5'-phosphoric acid diester bridges in the pyrimidine positions and at the 5'-end and/or at the 3'-end are replaced by formacetals and/or 3'-thioformacetals;

c) the sugar phosphate backbone is completely or partially replaced by "PNAs" or PNA-DNA hybrids;

d) the β-D-2'-deoxyribose units are completely or partially replaced by 2'-F-2'-deoxyribose, 2'-O-$(C_1-C_6)$-alkylribose, 2'-O-$(C_2-C_6)$alkenylribose or 2'-$NH_2$-2'-deoxyribose;

e) the natural nucleoside bases are completely or partially replaced by 5-$(C_1-C_6)$-alkyluracil, 5-$(C_2-C_6)$-alkenyluracil, 5-$(C_2-C_6)$-alkynyluracil, 5-$(C_1-C_6)$-alkylcytosine, 5-$(C_2-C_6)$-alkenylcytosine, 5-$(C_2-C_6)$-alkynylcytosine, 5-fluorouracil, 5-fluorocytosine, 5-chlorouracil, 5-chlorocytosine, 5-bromouracil, 5-bromocytosine, 7-deaza-7-deaza-7-$(C_2-C_7)$-alkynylguanine, 7-deaza-7-$(C_2-C_7)$-alkynyladenine, 7-deaza-7-$(C_2-C_7)$-alkenylguanine, 7-deaza-7-$(C_2-C_7)$-alkenyladenine, 7-deaza-7-$(C_1-C_7)$-alkylguanine, 7-deaza-7-$(C_1-C_7)$-alkyladenine, 7-deaza-7-bromoguanine, 7-deaza-7-bromoadenine.

Particularly preferred compounds of the formula I are those in which n is a number from 0 to 30;

Q and Q' independently of one another are hydrogen, $R^8$, in which $R^8$ is H, $(C_1-C_6)$-alkyl, phenyl or 2-(4-nitrophenyl)ethyl, or are oligonucleotides which can be unmodified or modified as follows:

a) the 3'-and/or 5'-phosphoric acid diester bridges are completely or partially replaced by phosphorothioate, phosphorodithioate or methylphosphonate bridges;

b) one, two or three 3'-or 5'-phosphoric acid diester bridges are replaced at the 5'-and at the 3'-end;

c) the sugar phosphate backbone is completely or partially replaced by "PNAs" or PNA-DNA hybrids;

d) the β-D-2'-deoxyribose units are completely or partially replaced by 2'-F-2'-deoxyribose, 2'-O-$(C_1-C_4)$-alkylribose, 2'-O-$(C_2-C_4)$alkenylribose or 2'-$NH_2$-2'-deoxyribose;

e) the natural nucleoside bases are completely or partially replaced by 5-$(C_3-C_6)$-alkyluracil, 5-$(C_2-C_6)$-alkenyluracil, 5-$(C_2-C_6)$-alkynyluracil, 5-$(C_2-C_6)$-alkylcytosine, 5-$(C_2-C_6)$-alkenylcytosine, 5-$(C_2-C_6)$-alkynylcytosine, 7-deaza-7-$(C_2-C_7)$-alkynylguanine, 7-deaza-7-$(C_2-C_7)$-alkynyladenine, 7-deaza-7-$(C_2-C_7)$-alkenylguanine, 7-deaza-7-$(C_2-C_7)$-alkenyladenine, 7-deaza-7-$(C_1-C_7)$-alkylguanine, 7-deaza-7-$(C_1-C_7)$-alkyladenine, 7-deaza-7-bromoguanine, 7-deaza-7-bromoadenine.

Very particularly preferred compounds of the formula I are those in which n is a number from 0 to 25;

B independently of one another is a natural nucleobase;

Z is hydroxyl, ethoxy, (4-nitrophenyl)ethoxy or phenoxy;

Q and Q' independently of one another is hydrogen, $R^8$, in which $R^8$ is H, $(C_1-C_6)$-alkyl, phenyl or 2-(4-nitrophenyl)ethyl, or are oligonucleotides which can be unmodified or modified as follows, a) the 3'-and/or 5'-phosphoric acid diester bridges are completely or partially replaced by phosphorothioate bridges;

c) the sugar phosphate backbone is completely or partially replaced by "PNAs" or PNA-DNA hybrids;

d) the β-D-2'-deoxyribose units are completely or partially replaced by 2'-O-methyl, 2'-O-allyl or 2'-O-butylribose; or e) the natural nucleoside bases are completely or partially replaced by 5-hexynylcytosine, 5-hexynyluracil, 5-hexynylcytosine, 7-deaza-7-propynylguanine, 7-deaza-7-propynyladenine, 7-deaza-7-methylguanine, 7-deaza-7-methyladenine, 7-deaza-7-bromoguanine, 7-deaza-7-bromoadenine.

The invention further relates to compounds of the formula I in which Q and Q' are linked, i.e. form a cyclic molecule, where the possibility should still apply that Q and Q' together afford a single bond. The synthesis of such compounds can be carried out analogously to described processes, for example Gao et al., Nucl. Acids Res. 23 (1995) 2025, or Wang and Kool, Nucl. Acids Res. 22 (1994) 2326.

The invention further relates to oligonucleotides or modified oligonucleotides, for example PNAs, in which compounds of the formula I are incorporated at the 3'-end or at the 5'-end or at the 5'- and at the 3'-end.

The linkage of the oligonucleotides with the compounds of the formula I is preferably carried out via the 5'-or 3'-hydroxyl group of the nucleotide units, likewise via a phosphonic acid monoester bond. The linkage with oligonucleotides is illustrated by way of example in the formulae XVIII and XIX.

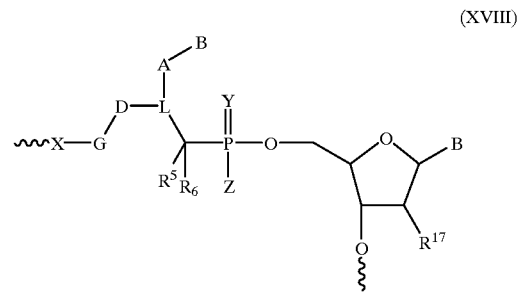

(XVIII)

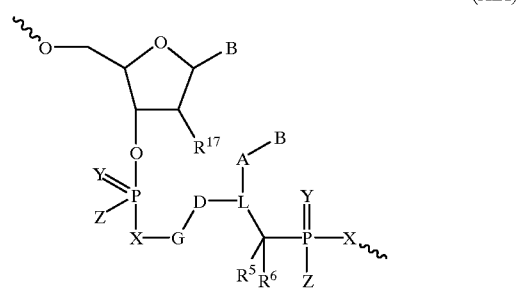

(XIX)

$R^{17}$ is H, OH, F, 2'-O-$(C_1-C_6)$-alkyl or 2'-O-$(C_2-C_6)$-alkenyl, preferably H or methoxy or O-allyl, particularly preferably H. All other variables are illustrated above.

Formula XX and formula XXI, in which the variables have the above meaning, illustrate by way of example the linkage with PNAs.

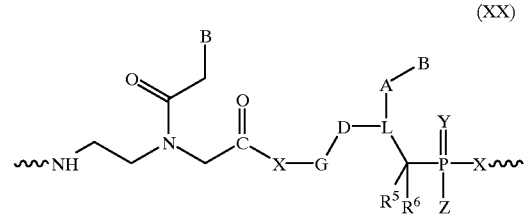

(XX)

11

-continued

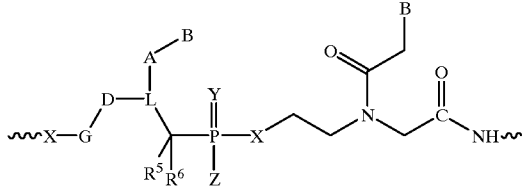

(XXI)

The combinations of the compounds according to the invention utilizing (abbreviated PMENA) oligonucleotides or modified oligonucleotides, will be schematically illustrated again (OLIGO is unmodified or modified oligonucleotides) for example PNAs or other modifications, as are described above:

Examples of such combinations are:
5'-OLIGO-PMENA
5'-PMENA-OLIGO
5'-OLIGO-PMENA-OLIGO
5'-OLIGO-(PMENA-OLIGO)$_a$ (a=1–20)
5'-PMENA-OLIGO-PMENA
5'-PMENA-(OLIGO-PMENA)$_a$ (a=1–20)

The synthesis of these combined compounds is carried out in such a way that, according to the molecule, the synthesis of the PMENA units, which is described in the following, is begun first, which are then coupled with the oligonucleotide units. In this process, the oligonucleotides are coupled as monomer units or by block condensation by solid-phase synthesis or by solution synthesis by methods known to the person skilled in the art (Sonveaux, Bioorganic Chemistry 14 (1986) 274ff). The condensations are alternatively carried out by the amidite method, the H-phosphonate method or the phosphorotriester process (Sonveaux, Bioorganic Chemistry 14 (1986) 274ff). If, conversely, PMENA units are coupled to OLIGO units, this is preferably carried out by the method described in f$_1$) below. Conjugation with PNA units is carried out in the same manner or, if (monomeric or oligomeric) PNA units are coupled to PMENA units, with the methods of peptide synthesis or of ester synthesis known to the person skilled in the art. These combinations can be made by means apparent to those skilled in the art in view of the present specification.

The invention furthermore relates to a compound having one of the formulae:

5'-Q$^{11}$-OLIGO-(PMENA-OLIGO)a-Q$^{12}$;
5'-Q$^{13}$-PMENA-OLIGO-PMENA-Q$^{14}$;
5'-Q$^{15}$-PMENA-(OLIGO-PMENA)a-Q$^{16}$; or
5'-OLIGO-(PMENA-OLIGO)a;

wherein a is 1–20, OLIGO represents an unmodified or modified oligonucleotide, and PMENA represents a compound of formula I':

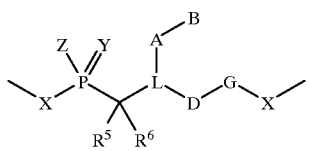

(I)' in which

B independently of one another is hydrogen, hydroxyl, (C$_1$–C$_{20}$)-alkyl, (C$_1$–C$_{20}$)-alkoxy, (C$_1$–C$_{20}$)-alkylthio,

12

(C$_6$–C$_{20}$)-aryl, (C$_6$14 C$_{20}$)-aryl-(C$_1$–C$_6$)-alkyl, (C$_6$–C$_{20}$)-aryl-(C$_1$–C$_6$)-alkoxy, (C$_6$–C$_{20}$)-aryl-(C$_1$–C$_6$)-alkylthio, an aromatic group or a heterocyclic group, wherein alkyl, aryl, aromatic or heterocyclic group is optionally substituted one or more times by hydroxyl, (C$_1$–C$_4$)-alkoxy, —NR$^9$R$^{10}$, —C(O)OH, oxo, —C(O)OR$^8$, —C(O)NR$^9$R$^{10}$, —CN, —F, —Cl, —Br, —NO$_2$, (C$_2$–C$_6$)-alkoxyalkyl, —S(O)$_m$R$^8$, —(C$_1$–C$_6$) —alkyl-S(O)$_m$R$^8$, —NHC(=NH)NHR$^8$, —C(=NH)NHR$^8$, NR$^9$C(=O)R$^8$, =NOR$^8$, NR$^9$C(=O)OR$^{10}$, —OC(=O)NT$^9$R$^{10}$, or —NR$^9$C(=O)NR$^9$R$^{10}$, B independently of one another is a natural nucleobase, an unnatural nucleobase or a reporter ligand;

A-B is a D—or L-amino acid condensed on via the carboxyl group or peptides consisting of amino acids having a length of up to 5 amino acid residues, L independently of one another is N or R$^1$N$^+$, and R$^1$ is hydrogen or (C$_1$–C$_6$)-alkyl optionally substituted by hydroxyl, (C$_1$–C$_6$) -alkoxy, (C$_1$–C$_6$)-alkylthio or amino;

A independently of one another is a single bond, a methylene group or a group of formula IIa or IIb;

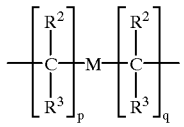

(IIa)

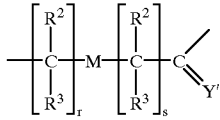

(IIb)

Y' is =O, =S, =CH$_2$, =C(CH$_3$)$_2$ or =NR$^1$, where R$^1$ is as defined above;

M is a single bond, —O—, —S— or —NR$^1$—, where R$^1$ is as defined above;

R$^2$ and R$^3$ independently of one another are hydrogen, hydroxyl, (C$_1$–C$_6$)-alkoxy, (C$_1$–C$_6$)-alkylthio, amino, halogen, or (C$_1$–C$_6$)-alkyl optionally substituted by hydroxyl, (C$_1$–C$_6$)-alkoxy or (C$_1$–C$_6$)-alkylthio;

p and q independently of one another are zero to 5;

r and s independently of one another are zero to 5;

D and G each independently represent Cr$^5$R$^6$ which can be the same or different;

R$^5$ and R$^6$ independently of one another are hydrogen, (C$_1$–C$_6$-alkyl, (C$_6$–C$_{20}$)-aryl, (C$_6$–C$_{20}$) -aryl-(C$_1$–C$_6$)-alkyl, hydroxyl, (C$_1$–C$_6$)-alkoxy, (C$_1$–C$_6$)-alkylthio, wherein alkyl and aryl are optionally substituted by SR$^1$ or NR$^1$R$^{1'}$, where R$^1$ is as defined above and R$^{1'}$ independently of R$^1$ has the same meaning as R$^1$;

X is —O—, —S— or —NR$^1$—, in which R$^1$ is as defined above;

Y is =O or =S;

Z is —OR$^8$, —NR$^9$R$^{10}$ or X'Q', where X'is defined as X and Q' is hydrogen, R$^8$, modified or unmodified oligonucleotides or conjugates which a) favorably affect the properties of antisense oligonucleotide, b) affect the properties of triple helix-forming oligonucleotides, c) serve as a lable of a DNA probe, or d) during the hycridization of the oligonucleotides analog to the target nucleic acid, attack the target nucleic acid with binding or crosslinking;

$R^8$ is hydrogen, $(C_1-C_{18})$-alkyl, $(C_2-C_{18})$-alkenyl, $(C_3-C_{18})$-alkynly, $(C_6-C_{12})$-aryl, $(C_6-C_{12})$-aryl-$(C_1-C_6)$-alkyl, wherein alkyl is optionally substituted one or more times by hydroxyl, $(C_1-C_4)$-alkoxy, F, Cl or Br and wherein aryl is optionally substituted 1–3 times by hydroxyl, $(C_1-C_4)$-alkoxy, $(C_1-C_4)$-alkyl, F, Cl, Br, $NO_2$, $-NR^9R^{10}$, $-C(O)OH$, $-C(O)O-(C_1-C_6)$-alkyl or $-C(O)NR^9R^{10}$;

$R^9$ and $R^{10}$ independently of one another are hydrogen, $(C_1-C_{18})$-alkyl, $(C_2-C_{18})$-alkenyl, $(C_3-C_{18})$-alkynyl, $(C_6-C_{12})$-aryl, $(C_6-C_{12})$-aryl-$(C_1-C_6)$-alkyl, where alkyl is optionally substituted one or more times by hydroxyl, $(C_1-C_4)$-alkyoxy, F, Cl or Br; or $R^9$ and $R^{10}$ form a 4 to 7-membered ring together with the N atom in $-NR^9R^{10}$;

and wherein $Q^{13}$ and $Q^{14}$ either both represent hydrogen or together form a bond in a cyclic molecule; $Q^{15}$ and $Q^{16}$ either both represent hydrogen or together form a bond in a cyclic molecule; and $Q^{11}$ and $Q^{12}$ form a singel bond in a cyclic molecule.

The invention furthermore relates to a process for the preparation of compounds of the formula I, which comprises a₁) reacting a compound of formula III $$H_2L-D_{\diagdown G}\diagup^{X}\diagdown_{S^1} \quad (III)$$

in which

D, G, L and X have the abovementioned meanings and $S^1$ is a suitable protective group, such as dimethoxytrityl, monomethoxytrityl, trityl, pixyl, tert-butoxycarbonyl or fluorenylmethoxycarbonyl, preferably monomethoxytrityl or tert-butoxycarbonyl, with a compound of formula IV $$\underset{R^6}{\overset{R^5}{\diagdown}}=O \quad (IV)$$

in which $R^5$ and $R^6$ have the abovementioned means, in a suitable organic solvent, for example in methanol, ethanol, isopropanol, butanol, acetonitrile, dichloromethane (DCM), chloroform, benzene, dimethylformamide (DMF), dimethyl sulfoxide (DMSO), diethyl ether, ethyl acetate (EA), tetrahydrofuran (THF), N-methylpyrrolidone, petroleum ether, xylene or toluene or mixtures of suitable solvents, preferably in methanol or ethanol, at temperatures sufficient to form (e.g. from 0° C. to 100° C., preferably at 10 to 50° C.) compounds of formula Va or Vb $$\underset{R^6}{\overset{R^5}{\diagdown}}=\underset{L}{\diagup}\diagdown_{D}\diagup^G\diagdown_{X}\diagup_{S^1} \quad (Va)$$

(Vb)

where, in the choice of the reaction conditions which are known to the person skilled in the art (e.g. in S. R. Sandler, W. Karo "Organic Functional Group Preparations", Vol. II, Second Edition, Academic Press, London, 1986, Chapter 12 ("Imines")), care is to be taken that they are compatible with the protective group $S^1$, i.e. if, for example, an acid-labile protective group such as the monomethoxytrityl protective group is chosen, no acid should be added during the reaction, b₁) reacting compounds of the formula Va or Vb with compounds of the formula VIa or VIb, preferably with compounds of the formula VIa $$\underset{S^3-X''}{\overset{S^2-X'}{\diagdown}}P\overset{Y}{\underset{\|}{-}}H \quad (VIa)$$

$$\underset{S^3-X''}{\overset{S^2-X'}{\diagdown}}P-Y-L^1 \quad (VIb)$$

in which

Y is as defined above,

X' and X" independently of one another have the same meaning as X defined above, $S^2$ and $S^3$ independently of one another are protective groups such as methyl, ethyl, phenyl, 2-chlorophenyl, 2,5-dichlorophenyl, 2,4-dichlorophenyl, 4-nitrophenyl, 4-methoxyphenyl, 2-cyanoethyl, 2-(4-nitrophenyl)ethyl, allyl, benzyl, 2,2,2-trichloro-1,1-dimethylethyl, 4-methoxybenzyl, 2,2,2-trichloroethyl, 8-hydroxyquinoline or other phosphate protective groups, such as are known to the person skilled in the art (Sonveaux, Bioorganic Chemistry 14 (1986) 274 ff), but preferably methyl, ethyl, phenyl, 2-(4-nitrophenyl)ethyl, allyl or 2,2,2-trichloroethyl, and $L^1$ is a leaving group, preferably $(C_1-C_4)$-alkyl, in a suitable organic solvent, for example in methanol, ethanol, isopropanol, butanol, acetonitrile, benzene, DMF, DMSO, DCM, EA, chloroform, diethyl ether, THF, N-methylpyrrolidone, petroleum ether, xylene or toluene or mixtures of suitable solvents, preferably in THF, at temperatures sufficient to form a compound of formula VII, e.g. from 0° C. to 100° C., preferably at 50 to 80° C., if appropriate with optional addition of bases, such as tri-$(C_1-C_6$-alkylamine, N-alkylmorpholine, pyridine, N,N-diemthylaminopyridine, butyllithium, lithium diisopropylamide (LDA), sodium hydride, sodium amide, potassium carbonate, cesium carbonate, potassium tert-butoxide or complex bases such as sodium amide-$R^{11}$ONa, where $R^{11}$ is ($C_2$–$C_6$)-alkyl of $CH_3CH_2$—O—$CH_2CH_3$, or uncharged, peralkylated polyaminophosphazene bases (Schwesinger, Nachr. Chem. Techn. Lab. 38 (1990) 1214; Angew. Chem. 99 (1987) 1212), but preferably without addition of base.

Formula VII has the following formula:

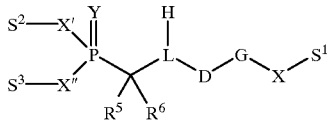
(VII)

in which

D, G, L, $R^5$, $R^6$, $S^1$, $S^2$, $S^3$, X, X', X" and Y are as defined above;

c$_1$) reacting a compound of formula VII with a compound of formula VIII

(VIII)

whose synthesis is described, for example, in Dueholm et al., J. Org. Chem. 59 (1994) 5767 and in which A has the abovementioned meaning.

$B^{PR}$ has the same meaning as B, but is optionally present in protected form, i.e. if B is a natural or unnatural nucleobase, $B^{PR}$ is the nucleobase whose amino or hydroxyl group's are protected by suitable known protective groups, such as the para-nitrophenylethyl group, the benzoyl group, the allyl group and the para-(t-butyl)benzoyl group for the hydroxyl group and the acetyl, benzoyl, para-(t-butyl) benzoyl, para-(methoxy)benzoyl group, para-nitrophenylethoxycarbonyl group, isobutyryl group, para-(t-butyl)phenylacetyl group, N,N-dimethylformamidino group, fluorenylmethyloxycarbonyl group, benzyloxycarbonyl group or phenoxyacetyl group for the amino group or other protective groups customary for nucleobases in oligonucleotide chemistry (Sonveaux, Bioorganic Chemistry 14 (1986) 274ff; Beaucage, Tetrahedron 49 (1993) 2223ff), preferably the following may be mentioned for $B^{PR}$:

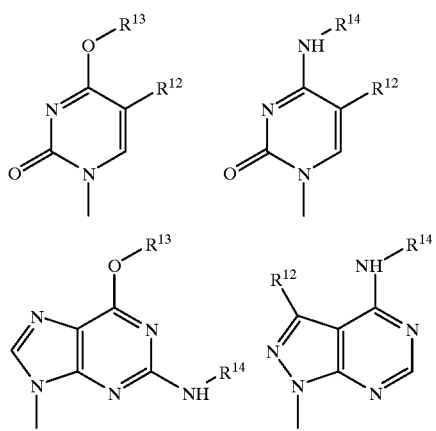

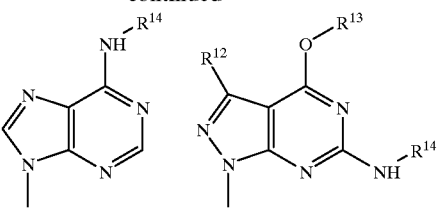

in which $R^{12}$ is hydrogen, 1-propynyl, 1-butynyl, 1-pentynyl or 1-hexynyl, in particular hydrogen, 1-propynyl or 1-hexynyl; and $R^{13}$ is hydrogen, diphenylcarbamoyl or 2-(4-nitrophenyl)-ethyl and $R^{14}$ is acetyl, benzoyl, para-(t-butyl)benzoyl, para-(methoxy)benzoyl, para-nitrophenylethyloxycarbonyl, isobutyryl, para-(t-butyl)phenylacetyl, benzyloxycarbonyl or phenoxyacetyl, and $L^2$ is a leaving group known to the person skilled in the art, such as Cl, Br, O-SO$_2$methyl, O-SO$_2$trifluoromethyl, O-tosylate or O—$C_6F_5$ or, if A has the meaning of formula IIB, can also be OH;

in a suitable organic solvent, for example in acetonitrile, benzene, DMF, DMSO, DCM, EA, chloroform, diethyl ether, tetramethylurea, THF, N-methylpyrrolidone, petroleum ether, xylene or toluene or mixtures of suitable solvents, preferably in DMF, at temperatures sufficient to form a compound of the formula IX, e.g. from −20° C. to 100° C., more preferably at 0 to 50° C., if appropriate with optional addition of bases, such as tri-($C_1$–$C_6$)-alkylamine, N-alkylmorpholine, pyridine, N,N-dimethylaminopyridine, butyllithium, lithium diisopropylamide (LDA), sodium hydride, sodium amide, potassium carbonate, cesium carbonate, potassium tert-butoxide or complex bases such as sodium amide-$R^{11}$ONa, where R is ($C_2$–$C_6$)-alkyl or $CH_3CH_2$—O—$CH_2CH_3$ or the bases are unchanged, peralkylated polyamino-phosphazene bases (Schwesinger, Nachr. Chem. Techn. Lab. 38 (1990) 1214; Angew. Chem. 99 (1987) 1212), and if A is formula IIb and $L^2$ is OH, preferably with addition of triethylamine, diisopropylethylamine or N-ethylmorpholine or without addition of base and with addition of a coupling reagent customary for the coupling of peptide bonds.

Formula IX has the following formula:

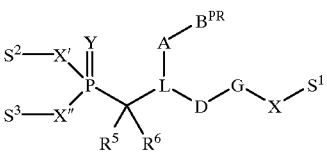
(IX)

in which

A, $B^{PR}$, D, G, L, $R^5$, $R^6$, $S^1$, $S^2$, $S^3$, X, X', X" and Y are as defined above:

d$_1$) removing the protective group $S_3$ from compounds of the formula IX by known processes (e.g. Greene, Wuts, Protective Groups in Organic Synthesis, J. Wiley & Sons, New York 1991). For example, for compounds of the formula IX, in which $S^2$ and $S^3$ are 2-(4-nitrophenyl)ethyl, by treatment with 0.1M 1,8-diazabicyclo[5.4.0]undec-7-ene (DBU) in pyridine or acetonitrile at room temperature or for compounds of the formula IX in which $S^2$ and $S^3$ are phenyl or ethyl, by treatment with an aqueous ammonia or for compounds of the formula IX in which $S^2$ is 2-(4-nitrophenyl)ethyl and $S^3$ is allyl, by treatment with $Pd[P(C_6H_5)_3]_4$ and triphenylphosphine in DCM (Hayakawa et al., J. Org. Chem. 58 (1993) 5551); or for compounds of the formula IX in which $S^2$ is 2-(4-nitrophenyl)ethyl and $S^3$ is ally, by treatment with 0.5M DBU in pyridine or acetonitrile or for compounds of the formula IX in which $S^2$ is 2-cyanoethyl and $S^3$ is allyl, by treatment with triethylamine in pyridine, or for compounds of the formula IX in which $S^2$ is 2-(4-nitrophenyl)ethyl and $S^3$ is 2,2,2-trichloro-1,1-dimethylethyl, by treatment with tributylphosphine.

compounds of the formula X being obtained

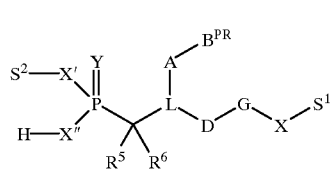

(X)

in which

A, $B^{PR}$, D, G, L, $R^5$, $R^6$, $S^1$, $S^2$, X, X', X" and Y are as defined above;

$e_1$) removing the protective group $S_1$ from compounds of the formula IX by known processes (e.g. Greene, Wuts, Protective Groups in Organic Synthesis, J. Wiley & Sons, New York 1991, Sonveaux, Bioorganic Chemistry 14 (1986) 274 ff), thus, for example, the monomethoxytrityl protective group is removed by treatment with acid, for example by treatment with 80% acetic acid, with 1–4% dichloroacetic acid in methylene chloride or chloroform, with 2% p-toluenesulfonic acid in DCM/methanol or by treatment with 1% trifluoroacetic acid in chloroform, compounds of the formula XI being obtained

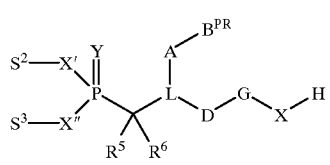

(XI)

in which

A, $B^{PR}$, D, G, L, $R^5$, $R^6$, $S^2$, $S^3$, X, X', X" and Y are as defined above;

$f_1$) reacting compounds of the formula XI with compounds of the formula X according to the "phosphotriester process" known from oligonucleotide chemistry (Sonveaux, Bioorganic Chemistry 14 (1986) 2744ff, Reese, J. Chem. Soc. Perkin Trans. 1993, 2291ff) in a suitable organic solvent, such as acetonitrile, benzene, DMF, DMSO, DCM, EA, chloroform, diethyl ether, tetramethylurea, THF, N-methylpyrrolidone, petroleum ether, xylene or toluene or mixtures of suitable solvents, preferably in pyridine, at temperatures from −20° C. to 100° C., more preferably at 0 to 50° C., with addition of a coupling reagent, such as 6-nitrobenzotriazol-1-yloxytris(dimethylamino) phosphonium hexafluorophosphate (NBOP, Hashmi, Nucleosides & Nucleotides 13 (1994) 1059), benzotriazole-1-yloxytris (dimethylamino) phosphonium hexafluorophosphate (BOP, B. Castro, J. R. Dormoy, G. Evin and C. Selve, Tetrahedron Lett. 1975, 1219–1222), benzotriazol-1-yloxytripyrrolidino) phosphonium hexafluorophosphate (PyBOP, J. Coste, D. Le-Nguyen and B. Castro, Tetrahedron Lett. 1990, 205–208), O-(7-aza)benzotriazol-1-yltetramethyluronium hexafluorophosphate (HATA, L. Carpino, J. Am. Chem. Soc. 1993, 115, 4397), N,N-bis[2-oxo-3-oxazolidinyl]diaminophosphoryl chloride (Katti, Tetrahedron Lett. 26 (1985) 2547), 2-chloro-5,5-dimethyl-2-oxo-1,3,2-dioxaphosphorinane (Stawinski, Nucl. Acids Res., Symp. Ser. 24, 1991, 229) or a compound of the formula XII

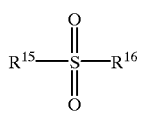

(XII)

in which $R^{15}$ is ($C_6$–$C_{12}$)-aryl, optionally substituted one to four times by ($C_1$–$C_6$)-alkyl, ($C_1$–$C_6$)-alkoxy, nitro, chlorine or bromine and where one to 3 carbon atoms are optionally substituted by heteroatoms, preferably nitrogen, i.e. for example phenyl, tolyl, 2,4,6-trimethylphenyl, 2,4,6-triisopropylphenyl, 2,3,5,6-tetramethylbenzene (Losse, Liebigs Ann. Chem. 1989, 19ff), 4-bromobenzene, 2-nitrobenzene, 4-nitrobenzene or 8-quinolyl, preferably 2,4,6-trimethylphenyl or 2,4,6-triisopropylphenyl, and $R^{16}$ is a leaving group such as chlorine, bromine, imidazole, triazole, 4-nitroimidazole, 1,2,3,4-tetrazole or 3-nitro-1,2,4-triazole.

preferably using a coupling reagent of the compound of the formula XII or BOP, PyBOP or HATU, optionally with addition of a catalyst (Reese, J. Chem. Soc, Perkin Trans. 1993, 2291ff), such as N-methylimidazole, pyridine-N-oxides such as 4-methoxypyridine-N-oxide or 4-ethoxypyridine-N-oxide, 4,6-dinitro-1-hydroxybenzotriazole, 1-hydroxyl-5-phenyltetrazole,1-hydroxy-5-(4-nitrophenyl)tetrazole, 3-nitro-1H-1,2,4-triazole, 5-(3-nitrophenyl)-1H-tetrazole, 5-(3,5-dinitrophenyl)-1H-tetrazole, 5-(1-methylimidazole-2-yl) methyl]-1H-tetrazole, 5-[(1-methylimidazole-2-yl)methyl]-1H-tetrazole or 1-hydroxy-4-nitro-6-(trifluoromethyl) benzotriazole, preferably with 4-ethoxypyridine-N-oxide or 4-methoxypyridine-N-oxide as a catalyst, where the preparation of the coupling reagents can be carried out in situ, or else carried out separately and the solution of the activated species (compound of formula (X) in combination with a coupling reagent) can be added in a suitable solvent.

to give compounds of the formula XIII

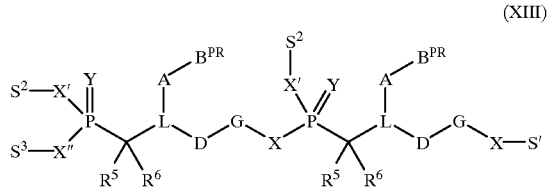

(XIII)

in which

A, $B^{PR}$, D, G, L, $R^5$, $R^6$, $S^1$, $S^2$, $S^3$, X, X', X" and Y are as defined abvoe;

g$_1$) starting from compounds of the formula XIII, repeating the steps e$_1$) and f$_1$) up to the desired chain length, compounds of the formula XIV resulting

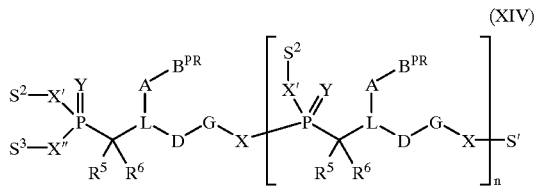

(XIV)

in which
A, B$^{PR}$, D, G, L, R$^5$, R$^6$, S$^1$, S$^2$, S$^3$, X, X', X", Y and n are as defined above;

h$_1$) removing the protective groups S$^1$, S$^2$ and S$^3$ and the protective groups on B$^{PR}$ according to known processes (e.g. Greene, Wuts, Protective Groups in Organic Synthesis, J. Wiley & Sons, New York 1991), i.e., for example, the protective group S$^1$ as described in step e$_1$), the protective groups S$^2$ or S$^3$, if they are 2-(4-nitrophenyl)ethyl, by treatment with 0.5M 1,8-diazabicyclo [5.4.0]undec-7-ene (DBU) in pyridine or acetonitrile at room temperature, if S$^2$ or S$^3$ is phenyl, by treatment with aqueous ammonia, if S$^2$ or S$^3$ is allyl, by treatment with Pd[P(C$_6$H$_5$)$_3$]$_4$ and triphenylphosphine in DCM (Hayakawa et al., J. Org. Chem. 58 (1993) 5551), if S$^2$ or S$^3$ is 2-cyanoethyl, by treatment with triethylamine in pyridine, or if S$^2$ or S$^3$ is 2,2,2-trichloro-1,1-dimethylethyl, by treatment with tributylphosphine, and the protective groups on B$^{PR}$, for example if R$^{14}$ is para-nitrophenylethyloxycarbonyl, with 0.5M DMU in pyridine, if R$^{14}$ is isobutyryl or benzoyl or para-methoxybenzoyl, with conc. NH$_4$OH at 20 to 60° C. or, if R$^{13}$ is 2-(4-nitrophenyl)ethyl, by treatment with 0.5M DBU in pyridine or acetonitrile, is preferred, if S$^1$ equals monomethoxytrityl and S$^2$ equals 2-(para-nitrophenyl)ethyl, preferably the monomethoxytrityl group is first removed as described in e$_1$), then S$^2$ is removed as described, then the remaining protective groups, for example on the nucleobases, are removed;
and optionally introducing the groups Q and Q' according to processes known to the person skilled in the art, (see, for example, Uhlmann & Peyman, Chem. Rev. 90 (1990) 543; M. Manoharan in "Antisense Research and Applications", Crooke and Lebleu, Eds., CRC Press, Boca Raton, 1993, Chapter 17, p.303ff; EP-A 0 552 766; S. Agrawal in Methods in Molecular Biology, Vol. 26, P. 93 ff, Humana Press, Totowa 1994), and optionally cyclizing the compounds obtained according to Wang, Nucl. Acids Res. 22 (1994) 2326, whereby compounds of the formula I result.

Alternatively, conjugates Q' can also be incorporated into the monomer units of the formula XXII by prcoesses known to the person skilled in the art (J. March, "Advanced Organic Chemistry", Fourth Ed., J. Wiley & Sons, 1992), which are then incorporated into the compounds of the formula I according to the processes mentioned.

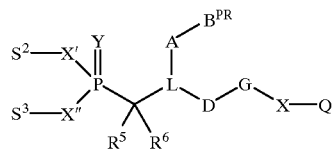

(XXII)

Compounds of the formula XXII can be prepared, for example, for Q'=alkyl, by reaction of compounds of the formula XXIII with compounds of the formula VIa or VIb and further reactions analogously to those described for the formulae Va and Vb.

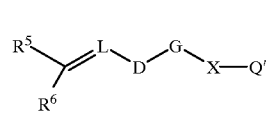

(XXIII)

Compounds of the formula XXII can also be prepared from compounds of the formula IX by removal of the protective group S$^1$ and introduction of the group Q' according to known processes (J. March, "Advanced Organic Chemistry", Fourth Ed., J. Wiley & Sons, 1992).

Alternatively, conjugates Q and Q" can also be incorporated into the monomer units of the formula XXIV by processes known to the person skilled in the art (J. March, "Advanced Organic Chemistry", Fourth Ed., J. Wiley & Sons, 1992), which are then incorporated into the compounds of the formula I according ot the processes mentioned.

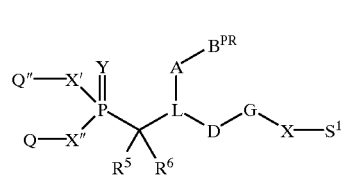

(XXIV)

Coupling reagents for the linkage of peptide bonds (see c$_1$)) are described, for example, in Houben-Weyl, Methoden der oganischen Chemie, [Methods of organic chemistry] Volume 15/2, Georg Thieme Verlag Stutgart 1974 and further reagents such as BOP (B. Castro, J. R. Dormoy, G. Evin and C. Selve, Tetrahedron Lett. 1975, 1219–122), PyBOP (J. Coste, D. Le-Nguyen and B. Castro, Tetrahedron Lett. 1990, 205–208), BroP (J. Coste, M.-N. Dufour, A. Pantaloni and B. Castro, Tetrahedron Lett. 1990, 669–672), PyBroP (J. Coste, E. Frerot, P. Jouin and B. Castro, Tetrahedron Lett. 1991, 1967–1970) and uronium reagents, such as HBTU (V. Dourtoglou, B. Gross, V. Lambropoulou, C. Zioudrou, Synthesis 1984, 572–574), TBTU, TPTU, TSTU, TNTU (R. Knorr, A. Trzeciak, W. Bannwarth and D. Gillessen, Tetrahedron Letters 1989, 1927–1930), TOTU (EP-A-O 460 446), HATU (L. A. Carpino, J. Am. Chem. Soc. 1993, 115, 4397–4398), HAPyU, TAPipU (A. Ehrlich, S. Rothemund, M. Brudel, M. Beyermann, L. A. Carpino and M. Bienert, Tetrahedron Lett. 1993, 4781–4784), BOI (K. Akaji, N. Kuriyama, T. Kimura, Y. Fujiwara and Y. Kiso, Tetrahedron Lett. 1992, 3177–3180) or acid chlorides or acid fluorides (L. A. Carpino, H. G. Chao, M. Beyermann and M. Bienert, J. Org. Chem., 56 (1991), 2635; J.-N. Bertho, A. Loffet, C. Pinel, F. Reuther and G. Sennyey in E. Giralt and D. Andreu (Eds.) Peptides 1990, Escom Science Publishers B. V. 1991, pp. 53–54; J. Green and K. Bradley, Tetrahedron 1993, 4141–4146), 2,4,6-mesitylenesulfonyl-3-nitro-1,2,4-triazolide (MSNT) (B. Blankemeyer-Menge, M. Nimitz and R. Frank, Tetrahedron Lett. 1990, 1701–1704), 2,5-diphenyl-2,3-dihydro-3-oxo-4-hydroxythiophene dioxide (TDO) (R. Kirstgen, R. C. Sheppard, W. Steglich, J. Chem. Soc. Chem. Commun. 1987, 1870–1871) or activated esters (D. Hudson, Peptide Res. 1990, 51–55) in the respective references.

The use of carbodiimides, e.g. dicyclohexylcarbodiimide or diisopropylcarbodiimide, is further preferred. Phosphonium reagents, such as PyBOP or PyBroP, uronium reagents, such as HBTU, TBTU, TPTU, TSTU, TNTU, TOTU or HATU and BOI are also preferably used.

In this case, the coupling can be carried out directly by addition of compounds of the formula VIII using the activating reagent and optionally with addition of additives such as 1-hydroxybenzotriazole (HOBt) (W. König, R. Geiger, Chem. Ber. 103, 788 (1970)) or 3-hydroxy-4-oxo-3,4-dihydrobenzotriazine (HOObt) (W. König, R. Geiger, Chem. Ber. 103, 2034 (1970)) or else the preactivation of the units as an activated ester can be carried out separately and the solution of the activated species in a suitable solvent can be added.

The invention furthermore relates to a process for the preparation of the compounds of the formula I, in which n is 1 to 100, which comprises, in the compounds of the formulae XV and XVI

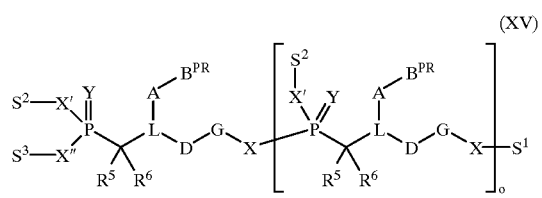

(XV)

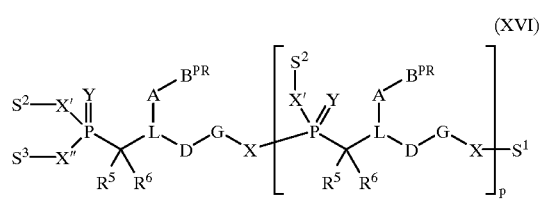

(XVI)

in which
A, $B^{PR}$, D, G, L, $R^5$, $R^6$, $S^1$, $S^2$, $S^3$, X, X', X" and Y are as defined above,
o and p independently of one another are zero to 50, preferably zero to 20 and o+p+1=n;
  $a_2$) in the compounds of the formula XV removing the protective group $S^1$ as described under $e_1$),
  $b_2$) in the compounds of the formula XVI removing the protective group $S^3$ as described under $d_1$) and
  $c_2$) coupling the resulting compounds with one another as described under $f_1$), compounds of the formula XIV resulting

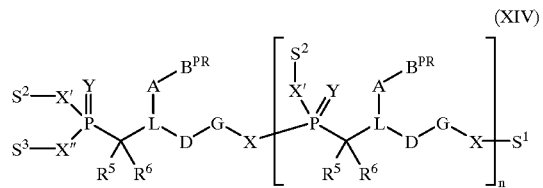

(XIV)

in which
A, $B^{PR}$, D, G, L, $R^5$, $R^6$, $S^1$, $S^3$, X, X', X", Y and n are as defined above,
  $d_2$) and reacting these as described under $h_1$) to give compounds of the formula I.

The invention furthermore relates to a process for the preparation of the compounds of the formula I, which comprises $a_3$) coupling compounds of the formula X

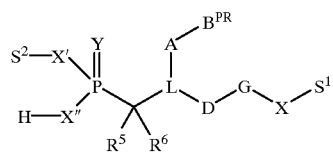

(X)

in which
A, $B^{PR}$, D, G, L, $R^5$, $R^6$, $S^1$, $S^2$, X, X', X" and Y are as defined above,
to a solid support via a SPACER according to known processes, to give compounds of the formula XVII,

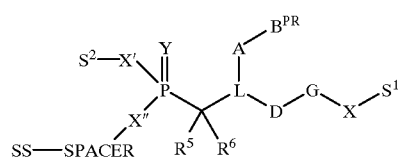

(XVII)

in which
A, $B^{PR}$, D, G, L, $R^5$, $R^6$, $S^1$, $S^2$, X, X', X" and Y are as defined above,
SS is a solid support suitable for solid-phase synthesis, such as aminopropyl-CPG (CPG=®Controlled Pore Glass) or ®Tentagel, and
SPACER is a group removable from the support after synthesis has taken place, such as is known to the person skilled in the art (Sonveaux, Bioorganic Chemistry 14 (1986) 274ff), for example the bis(hydroxyethyl)sulfonyl group, as is described in EP-A 0 552 766 or SPACER is bifunctional conjugate molecules Q, which are linked to the solid support via known removable groups, for example is nucleotides or oligonucleotides which are bound to the solid support via a succinic acid radical (Sonveaux, Bioorganic Chemistry 14 (1986) 274ff) or poly- or oligoethylene glycols which are bound to the solid support via a succinic acid radical (Jäschke, Tetrahedron Lett. 34 (1993) 301) or, for example, cholesterol derivatives which are bound to the solid support via a succinic acid radical (MacKellar, Nucl. Acids Res. 20 (1992) 3411);
  $b_3$) removing the protective group $S^1$ from compounds of the formula XVII

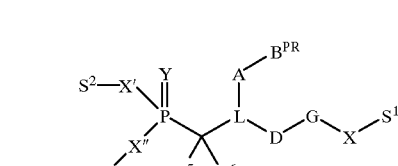

(XVII)

in which
A, $B^{PR}$, D, G, L, $R^5$, $R^6$, $S^1$, $S^2$, SS, SPACER, X, X', X" and Y are as defined above, A variation of the above latter-described process for the preparation of a compound of formula I comprises $a_3$) coupling a compound of formula X

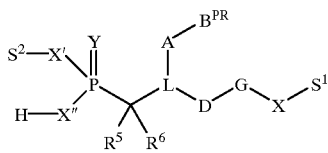
(X)

in which
A, $B^{PR}$, D, G, L, $R^5$, $R^6$, $S^1$, $S^2$, X, X', X" and Y are as defined above,
to a solid support (SS) via a SPACER to form a compound of formula XVII,

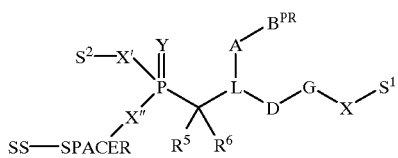
(XVII)

in which
A, $B^{PR}$, D, G, L, $R^5$, $R^6$, $S^1$, $S^2$, X, X', X" and Y are as defined above,
SS is a solid support suitable for solid-phase synthesis, and
SPACER is a group removable from the support after synthesis has taken place, or SPACER is a bifunctional conjugate molecule Q linked to solid support via removable groups, $b_3$) removing the protective group $S^1$ from the compound of formula XVII $c'_3$) reacting the resulting compound with a compound of formula X

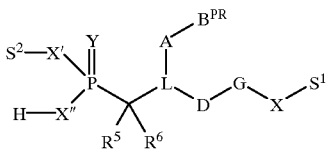
(X)

in an organic solvent, with addition of a coupling reagent or a compound of formula XII

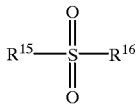
(XII)

in which $R^{15}$ is $(C_6–C_{12})$-aryl, optionally substituted one to four times by $(C_1–C_6)$-alkyl, $(C_1–C_6)$- alkoxy, nitro, chlorine or bromine and where one to 3 ring carbon atoms are optionally substituted by heteroatoms, and $R^{16}$ is a leaving group, optionally with addition of a catalyst, to form a compound of the formula XIII'

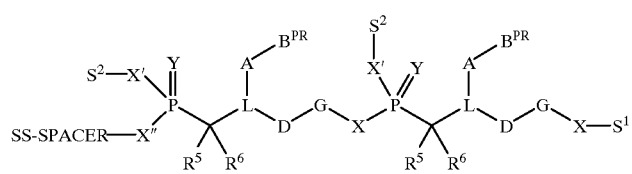
(XIII)'

$d'_3$) starting from the compound (XIII') resulting from said step $c'_3$), repeating steps $b_3$) and $c'_3$) as necessary to form a compound of formula XIV';

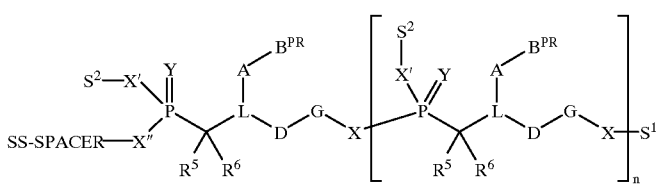
(XIV)'

$e'_3$) in any order, removing the protective groups on $B^{pr}$; removing the protective group $S^1$ and optionally coupling conjugate Q'; removing the resulting compound of step $d'_3$) from the solid support and optionally coupling conjugate Q; removing the protective groups $S^2$ and optionally introducing Q", $R^8$, $R^9$ and $R^{10}$,
in which Q, Q', Q", $R^8$, $R^9$ and $R^{10}$ are as defined above, F'$_3$) optionally cyclizing, to form a compound of formula I.

as described under e$_1$);

c$_3$) reacting the resulting compound with compounds of the formula X

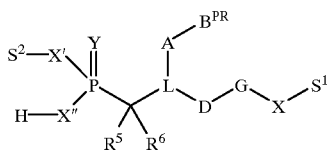

in which

A, B$^{PR}$, D, G, L, $R^5$, $R^6$, $S^1$, $S^2$, X, X', X" and Y are as defined above, as described under f$_1$);

d$_3$) repeating the steps b$_3$) and c$_3$) up to the desired chain length;

e$_3$) optionally coupling conjugates Q' by known processes (see, for example, Uhlmann & Peyman, Chem. Rev. 90 (1990) 543; M. Manoharan in "Antisense Research and Applications", Crooke and Lebleu, Eds., CRC Press, Boca Raton, 1993, Chapter 17, P.303ff; EP-A 0 552 766; S. Agrawal in "Methods in Molecular Biology", Vol. 26, P. 93ff, Humana Press, Totowa 1994);

f$_3$) removing the compounds produced in this way from the solid support by known proceses, for example the bis(hydroxyethyl)sulfonyl linkers, as described in EP-A 0 552 766, (HOE92/F012) by treatment with DBU, the succinic acid linker by treatment with aqueous ammonia and the protective groups as described in step h$_1$), where the removal of the protective groups can also be carried out before the cleavage from the support.

The compounds of the formula I are used as inhibitors of gene expression. The invention therefore further relates to the use of therapeutically active compounds according to the invention for the production of a pharmaceutical and to a process for the production of a pharmaceutical which comprises mixing the compounds according to the invention with a physiologically acceptable excipient and also, if appropriate, suitable additives and/or auxiliaries.

Therapeutically active compounds are understood in general as meaning those which, on account of the sequence of the units B which correspond to the nucleobases, carry out a function as analogs of antisense oligonucleotides, triple helix-forming oligonucleotides, aptamesr (RNA or DNA molecules which can bind to specific target molecules, e.g. proteins or receptors (e.g. L. C. Bock et al., Nature 1992, 355, 564) or ribozymes (catralytic RNA, see for example, Castanetto et al., Critical Rev. Eukar. Gene Expr. 1992, 2, 331), in particular as analogs of antisense oligonucleotides and triple helix-forming oligonucleotides.

Moreover, the present invention further relates to the use of the compounds according tothe invention as a diagnostic, for example for the detection of the presence or absence or the amount of a specific double-stranded or single-stranded nucleic acid molecule in a biological sample.

For use according to the invention, the compounds according to the invention generally have a length (n−1) of about 6–100, preferably of about 10–40, in particular of about 12–31 nucleotides. Otherwise, the preferred ranges, modifications or conjugations described above also apply here.

The pharmaceuticals of the present invention can be used, for example, for the treatment of illnesses which are caused by viruses, for example by HIV, SV-1, HSV-2, influenza, VSV, heptatitis B or papilloma viruses.

```
a) against HIV, e.g.
ACACCCAATTCTGAAAATGG            SEQ ID NO:1

AGGTCCCTGTTCGGGCGCCA            SEQ ID NO:2

GGTCCCTGTTCGGGCGCCA             SEQ ID NO:26

GTCGACACCCAATTCTGAAAATGGATAA    SEQ ID NO:3

GCTATGtCGACACCCAATTCTGAAA       SEQ ID NO:4

GTCGCTGTCTCCGCTTCTTCTTCCTG      SEQ ID NO:5

GTCTCCGCTTC-TICTTCCTGCCATAGG    SEQ ID NO:6 b) against HSV-1, e.g.
GCGGGGCTCCATGGGGGTCG            SEQ ID NO:7

GGAGGATGCTGAGGAGG               SEQ ID NO:28

GGAGGATGCTGAGG                  SEQ ID NO:29

CAGGAGGATGCTGAGGAGG             SEQ ID NO:30
```

The pharmaceuticals of the present invention are also suitable, for example, for the treatment of cancer or of restenosis. For example, in this case sequences (base sequences) can be used which are directed against targets which are responsible for carcinogenesis or cancer growth. Such targets are, for example:

1) Nuclear oncoproteins such as c-myc, N-myc, c-myb, c-fos, c-fos/jun, PCNA, p120
2) Cytoplasmic/membrane-associated oncoproteins such as EJ-ras, c-Ha-ras, N-ras, rrg, bcl-2, cdc-2, c-raf-1, c-mos, c-src, c-abl
3) Cellular receptors such as EGF receptor, c-erbA, retinoid receptors, protein kinase regulatory subunits, c-fms
4) Cytokines, growth factors, extracellular matrix such as CSF-1, IL-6, IL-1a, IL-1b, IL-2, IL-5, bFGF, myeloblastin, fibronectin.
4) Cytokines, growth factors, extracellular matrix such as CSF-1, IL-6, IL-1a, IL-1b, IL-2, IL-4, bFGF, myeloblastin, fibronectin.

Sequences according to the invention (base sequences) which are active against targets of this type are, for example,

```
a) against c-Ha-ras, e.g.
CAGCTGCAACCCAGC                 SEQ ID NO:8 c) c-myc, e.g.
GGCTGCTGGAGCGGGGCACAC           SEQ ID NO:9

AACGTTGAGGGGCAT                 SEQ ID NO:10 d) c-myb, e.g.
GTGCCGGGTCTTCGGGC               SEQ ID NO:11

GTGCCGGGTCTTCGGG                SEQ ID NO:27 e) c-fos, e.g.
GGAGAACATCATGGTCGAAG            SEQ ID NO:12

CCCGAGAACATCATGGTCGAAG          SEQ ID NO:13

GGGGAAAGCCCGGCAAGGGG            SEQ ID NO:14 f) p120, e.g.
CACCCGCCTTGGCCTCCCAC            SEQ ID NO:15
```

-continued

```
g) EGF receptor, e.g.
GGGACTCCGGCGAGCGC              SEQ ID NO:16

GGCAAACTTTCTTTTCCTCC           SEQ ID NO:17 h) p53 tumor suppressor, e.g.
GGGAAGGAGGAGGATGAGG            SEQ ID NO:18

GGCAGTCATCCAGCTTCGGAG          SEQ ID NO:19 i) bFGF, e.g.
GGCTGCCATGGTCCC                SEQ ID NO:31
```

The pharmaceuticals of the present invention are further suitable, for example, for the treatment of illnesses which are affected by integrins or cell-cell adhesion receptors, for example by VLA-4, VLA-2, ICAM or ELAM.

Sequences according to the invention (base sequences) which are active against targets of this type are, for example

```
a) VLA-4, e.g.
GCAGTAAGCATCCATATC             SEQ ID NO:20 b) ICAM, e.g.
CCCCCACCACTTCCCCTCTC           SEQ ID NO:21

CTCCCCCACCACTTCCCCTC           SEQ ID NO:22

GCTGGGAGCCATAGCGAGG            SEQ ID NO:23 c) ELAM-1, e.g.
ACTGCTGCCTCTTGTCTCAGG          SEQ ID NO:24

CAATCAATGACTTCAAGAGTTC         SEQ ID NO:25
```

The pharmaceuticals of the present invention are further suitable, for example, for the treatment of illnesses which are induced by factors such as TNF alpha.

Sequences according to the invention (base sequences) which are active against targets of this type are, for example

```
a) TNF-alpha, e.g.
TCATGGTGTCCTTTGCAGCC           SEQ ID NO:32

TCATGGTGTCCTTTGCAG             SEQ ID NO:33
```

The pharmaceuticals can be used, for example, in the form of pharmaceutical preparations which can be administered, for example, topically or orally, e.g. in the form of tablets, coated tablets, hard or soft gelating capsules, solutions, emulsions or suspensions. They can also be administered rectally, e.g. in the form of suppositories, or parenterally, e.g. in the form of injection solutions. For the production of pharmaceutical preparations, these compounds can be processed in therapeutically inert organic and inorganic excipients. Examples of such excipients for tablets, coated tablets and hard gelatin capsules are lactose, maize starch or derivatives thereof, talc and stearic acid or salts thereof. Suitable excipients for the production of solutions are water, polyols, sucrose, invert sugar and glucose. Suitable excipients for injection solutiosn are water, alcohols, polyols, glycerol and vegetble oils. Suitable excipients for suppositories are vegetable and hardened oils, waxes, fats and semiliquid polyols. The pharmaceutical preparations can also contain preservatives, solvents, stabilizers, wetting agents, emulsifiers, sweeteners, colorants, flavorings, salts for changing the osmotic pressure, buffers, coating compositions, antioxidants, and also, if appropriate, other therapeutic active compounds.

A preferred administration is oral administration. A further preferred form of administration is injection. For this, the antisense oligonucleotides are formulated in a liquid solution, preferably in a physiologically acceptable buffer, such as Hank's solution or Ringer's solution. The therapeutically active compounds according to the invention, however, can also be formulated in solid form and dissolved or suspended before use. The preferred dosages for systemic administration are about 0.01 mg/kg to about 50 mg/kg of body weight per day.

List of sequences

```
ACACCCAATTCTGAAAATGG           SEQ ID NO:1
AGGTCCCTGTTCGGGCGCCA           SEQ ID NO:2
GTCGACACCCAATTCTGAAAATGGATAA   SEQ ID NO:3
GCTATGTCGACACCCAATTCTGAAA      SEQ ID NO:4
GTCGCTGTCTCCGCTTCTTCTTCCTG     SEQ ID NO:5
GTCTCCGCTTCTTCTTCCTGCCATAGG    SEQ ID NO:6
GCGGGGCTCCATGGGGGTCG           SEQ ID NO:7
CAGCTGCAACCCAGC                SEQ ID NO:8
GGCTGCTGGAGCGGGGCACAC          SEQ ID NO:9
AACGTTGAGGGGCAT                SEQ ID NO:10
GTGCCGGGGTCTTCGGGC             SEQ ID NO:11
GGAGAACATCATGGTCGAAAG          SEQ ID NO:12
CCCGAGAACATCATGGTCGAAG         SEQ ID NO:13
GGGGAAAGCCCGGCAAGGGG           SEQ ID NO:14
CACCCGCCTTGGCCTCCCAC           SEQ ID NO:15
GGGACTCCGGCGCAGCGC             SEQ ID NO:16
GGCAAACTTTCTTTTCCTCC           SEQ ID NO:17
GGGAAGGAGGAGGATGAGG            SEQ ID NO:18
GGCAGTCATCCAGCTTCGGAG          SEQ ID NO:19
GCAGTAAGCATCCATATC             SEQ ID NO:20
CCCCCACCACTTCCCCTCTC           SEQ ID NO:21
CTCCCCCACCACTTCCCCTC           SEQ ID NO:22
GCTGGGAGCCATAGCGAGG            SEQ ID NO:23
ACTGCTGCCTCTTGTCTCAGG          SEQ ID NO:24
CAATCAATGACTTCAAGAGTTC         SEQ ID NO:25
GGTCCCTGTTCGGGCGCCA            SEQ ID NO:26
GTGCCGGGGTCTTCGGG              SEQ ID NO:27
GGAGGATGCTGAGGAGG              SEQ ID NO:28
GGAGGATGCTGAGG                 SEQ ID NO:29
CAGGAGGATGCTGAGGAGG            SEQ ID NO:30
GGCTGCCATGGTCCC                SEQ ID NO:31
TCATGGTGTCCTTTGCAGCC           SEQ ID NO:32
TCATGGTGTCCTTTGCAG             SEQ ID NO:33
```

EXAMPLES

1) Di(2-(p-nitrophenyl)ethyl) N-(4-methoxytriphenylmethoxy) ethylaminomethanephosphonate 1a) N-Fluorenylmethoxycarbonyl-2-aminoethanol 8.61 g (0.141 mol) of 2-aminoethanol wer dissolved in 250 ml of dioxane and 150 ml of $H_2O$. At 15–20° C., 17.79 g (0.212 mol) of $NaHCO_3$ were first added, then 50 g (0.148 mol) of fluorenylmethoxycarbonyl-N-succinimide in portions. The mixture was stirred at room temperature for 1 h, then it was evaporated to dryness. The residue was partitioned between dichloromethane (DCM) and $H_2O$, the organic phase was dried over $Na_2SO_4$ and the solvent was evaporated in vacuo. The residue was stirred with 100 ml of ether, and the product was filtered off with suction and washed well with ether. The yield was 38.77 g (97%).

MS (ES+): 284.2 (M+H)$^+$; $^1$H-NMR (200 MHz, DMSO, TMS): δ=3.05 (dd, 2H, $CH_2OH$); 3.39 (dd, 2H, N=$CH_2$); 4.25 (m, 3H, Ar—CH—$CH_2$); 4.61 (t, 1H, OH); 7.14–7.98 (m, 15H, Ar—H, NH).

1b) N-Fluorenylmethoxycarbonyl-2-amino-1-(4-methoxytriphenylmethoxy)ethane 10 g (35.3 mmol) of N-fluorenylmethoxycarbonyl-2-amino-ethanol (from Example 1a), dissolved in 100 ml of absol. N,N-dimethylformamide (DMF), were treated at 0° C. with 5.93 g (45.93 mmol) of diisopropylethylamine (DIPEA) and 10.91 g (35.3 mmol) of 4-methoxytriphenylmethyl chloride and stirred first at 0° C. for 1 h, then at room temperature for 1 h. The reaction mixture was evaporated and partitioned between DCM and a saturated aqueous $NaHCO_3$ solution. The organic phase was washed with $H_2O$ and dried over $Na_2SO_4$, and the solvent was evaporated in vacuo. To purify the product, it was chromatographed on silica gel (first n-heptane/ethyl acetate (EA)/triethylamine (TEA) 70:29:1; then EA/TEA 99:1). The yield was 14.4 g (73%).

MS (FAB): 562.3 (M+Li)$^+$; $^1$H-NMR (200 MHz, DMSO, TMS): δ=2.95 (t, 2H, $CH_2O$—MMTr); 3.21 (dd, 2H, N—$CH_2$); 3.75 (s, 3H, $OCH_3$); 4.25 (m, 3H, Ar—CH—$CH_2$); 4.61 (t, 1H, OH); 6.80–7.96 (m, 23H, Ar—H, NH).

1c) 2-Amino-1-(4-methoxytriphenylmethoxy)ethane 5.0 g (9 mmol) of N-fluorenylmethoxycarbonyl-2-amino-1-(4-methoxytriphenylmethoxy)ethane (from Example 1b), dissolved in 50 ml of absol. DMF, were treated at room temperature with 6.55 g (90 mmol) of diethylamine and the mixture was stirred for 2 h. To purify it, it was chromatographed on silica gel (first n-heptane/EA/TEA 50:49:1; then EA/methanol/TEA 79:20:1). The yield was 2.96 g (98.7%).

MS (ES+): 340.3 (M+Li)$^+$; $^1$H-NMR (200 MHz, DMSO, TMS): δ=2.75 (t, 2H, $CH_2O$—MMTr); 2.93 (dd, 2H, N—$CH_2$); 3.75 (s, 3H, $OCH_3$); 6.83–7.47 (m, 14H, Ar—H).

1d) 2-Methylimino-1-(4-methoxytriphenylmethoxy)ethane (trimer)

2.96 g (8.9 mmol) of 2-amino-1-(4-methoxytriphenylmethoxy)ethane (from Example 1c), dissolved in 10 ml of methanol were treated with ice cooling with 1.08 g (13.22 mmol) of 37% formaldehyde and stirred at room temperature for 4 h, a viscous precipitate being formed. The reaction mixture was evaporated and the residue was chromatographed on silica gel to purify it (n-heptane/EA/TEA 50:49:1). The yield was 1.7 g (55%).

MS (FAB): 1042.8 (M+Li)$^+$; 1034.8 (M−H)$^+$. $^1$H-NMR (200 MHz, DMSO, TMS): δ=2.60 (t, 6H, O—$CH_2$); 2.99 (t, 6H, N—$CH_2$); 3.69 (s, 9H, $OCH_3$); 6.78–7.42 (m, 42H, Ar—H).

1e) Di(2-(4-nitrophenyl)ethyl) phosphite 23.42 g (0.1 mol) of diphenyl phosphite were heated at 100° C. for 14 h under argon together with 33.43 g (0.2 mol) of p-nitrophenylethanol, and to purify it to the mixture was chromatographed on silica gel (n-heptane/EA 50:50; then EA/methanol 80:20). Yield: 55%.

MS (FAB): 403.1 (M+Na)$^+$; 381.1 (M+H)$^+$. $^1$H-NMR (200 MHz, DMSO, TMS): δ=3.03 (t, 4H, Ar—$CH_2$); 4.20 (4H, dt, O—$CH_2$); 6.71 (d, J=140 Hz; 1H; PH); 7.52 (d, 4H, Ar—H); 8.17 (d, 4H, Ar—H).

1f) Di-(2-(p-nitrophenyl)ethyl) N-(4-methoxytriphenylmethoxy)ethylaminomethanephosphonate 341 mg (0.329 mmol) of 2-methylimino-1-(4-methoxytriphenylmethoxy)ethane (trimer) (from Example 1d) were added to 500 mg (1.32 mmol) of di(2-(4-nitrophenyl)ethyl) phosphite (from Example 1e), dissolved in 2 ml of absol. Tetrahydrofuran (THF), and the mixture was stirred at 80° C. for 3 h. The solvent was evaporated and the residue was stirred at 100° C. for a further 30 min. To purify it, it was chromatographed on silica gel (first EA/TEA 99:1; then EA/methanol/TEA 90:9:1). Yield: 83%.

MS (FAB): 732.3 (M+Li)$^+$. $^1$H-NMR (200 MHz, DMSO, TMS): δ=2.64–3.06 (m, 10H, Ar—$CH_2$+P—$CH_2$+$CH_2$—OMMTr+N—$CH_2$); 3.73 (s, 3H, $OCH_3$); 4.16 (dt, 4H, PO—$CH_2$); 6.78–8.08 (m, 22H, Ar—H).

2) Di(2-(p-nitrophenyl)ethyl) N-(N$^6$-Anisoyl)cytosin)-1-yl-acetyl-N-(4-methoxytriphenylmethoxy)ethylaminomethanephosphonate 2a) 0.952 g (8.27 mmol) of N-ethylmorpholine (NEM), 0.834 g (2.76 mmol) of (N$^6$-anisoyl)cytosin-1-yl-acetic acid and 1.153 g (3.03 mmol) of O-(7-aza)benzotriazol-1-yltetramethyluronium hexafluorophosphate (HATU, L. Carpino, J. Am. Chem. Soc. 1993, 115, 4397) was added to 2.00 g (2.76 mmol) of di(2-(p-nitrophenyl)ethyl) N-(4-methoxytriphenylmethoxy)ethylaminomethanephosphonate (from Example 1f), dissolved in 60 ml of absol. DMF, and the mixture was stired at room temperature for 12 h. The same amount of HATU was then added once again and the mixture stirred at room temperature for a further 3 h. To purify it, it was chromatographed on silica gel (DCM/methanol/TEA 95:4:1). The yield was 2.7 g (97%).

MS (ES+): 1012.0 (M+H)$^+$. $^1$H-NMR (200 MHz, DMSO, TMS): δ=2.94 (t, 4H, P—O—$CH_2$—$CH_2$—Ar); 3.06 (t, 2H, MMTr—O—$CH_2$); 3.23–3.63 (m, 4H, P—$CH_2$+N—$CH_2$); 3.76 (s, 3H, $OCH_3$); 3.83 (s, 3H, $OCH_3$); 4.10 (dt, 4H, P—O—$CH_2$); 4.79 (s, broad, 2H, CO—$CH_2$); 6.80–8.18 (m, 28H, Ar—H, cytosinyl-H); 11.03 (s, broad, 1H, NH).

2b) Mixture as in Example 2a, but using O-(cyano(ethoxycarbonyl)methylamino)-1,1,3,3-tetramethyluronium tetrafluoroborate (TOTU, EP 0460446) instead of HATU. The yield was 57%. Spectroscopic data: see Example 2a.

3) N-(N$^6$-Anisoyl)cytosin-1-yl-acetyl-N-(4-methoxytriphenylmethoxy)ethylaminomethanephosphonic acid (2-(p-nitrophenyl)ethyl) monoester (triethylammonium salt)

1 g (0.99 mmol) of di(2-(p-nitrophenyl)ethyl) N-(N$^6$-anisoyl)cytosin-1-yl-acetyl-N-(4-methoxytriphenylmethoxy)ethylaminomethanephosphonate (from Example 2) was dissolved in 20 ml of a 0.1M solution of 1,8-diazabicyclo[5.4.0]undec-7-ene (DBU) in absol. acetonitrile and the mixture was stirred at room temperature for 4 h. The reaction mixture was partitioned between DCM and an aqueous $KH_2PO_4$ solution (pH 7), the organic phase was dried over $Na_2SO_4$ and the solvent was evaporated in vacuo. To purify the residue, it was chromatographed on silica gel (EA/methanol/TEA 70:29:1). The yield was 540 mg (57%).

MS (FAB): 906.5 (M—H+2Na)$^+$; 884.6 (M+Na)$^+$; 862.5 (M+H)$^+$. $^1$H-NMR (200 MHz, DMSO, TMS): δ=3.00 (m, 4H, P—O—$CH_2$—$CH_2$—Ar+MMTr—O—$CH_2$);

3.38–3.60 (m, 4H, P—CH$_2$+N—CH$_2$); 3.73 (s, 3H, OCH$_3$); 3.82 (s, 3H, OCH$_3$); 4.01 (dt, 2H, P—O—CH$_2$); 4.79 & 5.03 (in each case s, broad, 2H, CO—CH$_2$); 6.78–8.20 (m, 24H, Ar—H, cytosinyl-H); 11.00 (s broad, 1H, NH).

4) Di(2-(p-nitrophenyl)ethyl) N-(N$^6$-anisoyl)cytosin-1-yl-acetyl-N-(2-hydroxy)ethylamino-methanephosphonate 1.00 g (0.99 mmol) of di(2-(p-nitrophenyl)ethyl) N-(N$^6$-anisoyl)cytosin-1-yl-acetyl-N-(4-methoxytriphenylmethoxy)ethylaminomethanephosphonate (from Example 2) was dissolved in 80 ml of 80% aqueous acetic acid and the solution was stirred at room temperature for 4 h. The solvent was evaporated and the residue was coevaporated twice with toluene. To purify it, it was chromatographed on silica gel (EA/methanol/TEA 85:14:1). The yield was 522 mg (71%).
MS (FAB): 761.2 (M+Na)$^+$; 739.3 (M+H)$^+$. $^1$H-NMR (200 MHz, DMSO, TMS): δ=2.98 (t, 4H, P—O—CH$_2$—Ar) 3.38–3.67 (m, 4H, N—CH$_2$CH$_2$—OH); 3.80–3.89 (m, 2H, P—CH$_2$); 3.91 (s, 3H, OCH$_3$); 4.12 (dt, 4H, P—O—CH$_2$); 4.78 & 4.87 (in each case s, broad, 2H, CO—CH$_2$); 6.98–8.19 (m, 14H, Ar—H, cytosinyl-H); 11.02 (s, broad, 1H, NH).

5) 5'MMTr-C$^{An}$-(P(ONPE)-C$^{An}$-P(ONPE)$_2$

The synthesis was carried out analogously to Example 7 from N-(N$^6$-anisoyl)cytosin-1-yl-acetyl-N-(4-methoxytriphenylmethoxy)ethylaminomethanephosphonic acid (2-(p-nitrophenyl)ethyl monoester (triethylammonium salt) (Example 3) and di(2-(p-nitrophenyl)ethyl) N-(N$^6$-anisoyl) cytosin-1-yl-acetyl-N-(2-hydroxy) ethylaminomethanephosphonate (Example 4) To purify it, the compound was chromatrographed on silica gel (EA/methanol/TEA 85/14/1). Yield: 73%.
MS (FAB): 1605 (M+Na)$^+$; 1583 (M+H)$^+$. $^1$H-NMR (200 MHz, DMSO, TMS): δ=2.94–3.18 (m, 6H, P—O—CH$_2$—CH$_2$—Ar) 3.26–3.95 (m, 10H); 3.75 (s, 3H, OCH$_3$); 3.85 (s, 6H, OCH$_3$); 3.99–4.36 (m, 8H, P—O—CH$_2$); 4.75–4.92 (m, broad, 4H, CO—CH$_2$); 6.83–8.18 (m, 38H, Ar—H, cytosinyl-H); 10.98 & 11.03 (in each case s, broad, 2H, NH).

6) 5'-HO-C$^{An}$-P(ONPE)-C$^{An}$-O(ONPE)$_2$

The synthesis was carried out analogously to Example 4 from "5'-MMTr-C$^{An}$-P(ONPE)-C$^{An}$-P(ONPE)$_2$." (Example 5). To purify it, the compound was chromatographed on silica gel (EA/methanol/TEA 85:14:1). The yield was 74%.
MS (FAB): 1332.4 (M+Na)$^+$; 1310.3 (M+H)$^+$;

7) Diethyl N-(4-methoxytriphenylmethoxy) ethylaminomethanephosphonate

The synthesis was carried out analogously to Example 1f, but using diethyl phosphite. Yield: 87.5%
MS (FAB): 490.2 (M+Li)$^+$. $^1$H-NMR (200 MHz, DMSO, TMS): δ=1.22 (t, 6H, CH$_2$—CH$_3$); 2.80 (t, 2H, N—CH$_2$); 2.91 (d, J=12.5 Hz, 2H, P—CH$_2$); 3.02 (t, 2H, CH$_2$—OMMTr); 3.75 (s, 3H, OCH$_3$); 4.01 (dq, 4H, PO—CH$_2$); 6.84–7.45 (m, 14H, Ar—H).

8) Diethkyl N-thymin-1-yl-acetyl-N-(4-methoxytriphenylmethoxy)ethylaminomethanephosphonate 570.3 mg (4.22 mmol) of hydroxybenzotriazole (HOBT), 972.1 mg (8.44 mmol) of NEM, 777 mg (4.22 mmol) of thymidin-1-yl-acetic acid and 639 mg (5.06 mmol) of diisopropylcarbodiimide were added to 2.04 g (4.22 mmol) of diethyl N-(4-methoxytriphenylmethoxy) ethylaminomethanephosphonate Example 7), dissolved in 50 ml of absol. DMF. The mixture was stirred at room temperature for 16 h, the solvent was evaporated, the residue was dissolved in DCM and the solution was extracted with saturated aqueous NaHCO$_3$ solution, then was saturated with aqueous NaCl solution. The extract was dried over sodium sulfate and the solvent was evaporated. To purify it, the residue was chromatographed on silica gel (EA/methanol/ TEA 98:2:1). The yield was 2.47 g (90%).
MS (FAB): 662.3 (M+Na)$^+$; 656.3 (M+Li)$^+$. $^1$H-NMR (200 MHz, DMSO, TMS): δ=1.12–1.32 (m, 6H, CH$_2$—CH$_3$); 1.68 & 1.75 (in each case s, 3H, T—CH$_3$); 3.10–3.40 (m, 2H, CH$_2$—OMMTr); 3.53–3.70 (m, 4H, P—CH$_2$+N—CH$_2$); 3.75 (s, 3H, OCH$_3$); 3.83–4.16 (m, 4H, PO—CH$_2$); 4.62 & 4.72 (in each case s, 2H, CO—CH$_2$); 6.83–7.42 (m, 15H, Ar—H, T—H); 11.28 (s, 1H, NH).

9) N-thymin-1-yl-acetyl-N-(4-methoxytriphenylmethoxy)ethylaminomethanephosphonic acid monoethyl ester (triethylammonium salt)

811 mg (1.25 mmol) of diethyl N-thymin-1-yl-acetyl-N-(4-methoxytriphenylmethoxy) ethylaminomethanephosphonate (Example 8) were suspended in 3.75 ml of 1N NaOH. The mixture was stirred at room temperature for 3 h, then at 50° C. for 6 h. The reaction mixture was concentrated in vacuo and the residue was chromatographed on silica gel (EA/methanol/TEA 100:10:10, then 100:40:10). The yield was 897 mg (99.5%).
MS (ES-): 620.4 (M–H)$^-$. $^1$H-NMR (200 MHz, DMSO, TMS): δ=1.18 (t, 9H, N—CH$_2$—CH$_3$); 1.68 & 1.74 (in each case s, 3H, T—CH$_3$); 2.96–3.08 (q, 6H, N—CH$_2$—CH$_3$); 3.35 (m, 2H, N—CH$_2$); 3.43–3.70 (d, J=11 Hz, 2H, P—CH$_2$); 3.63 (t, 2H, CH$_2$—OMMTr); 3.75 (s, 3H, OCH$_3$); 3.78 (dq, 2H, PO—CH$_2$); 4.60 & 4.86 (in each case s, 2H, CO—CH$_2$); 6.82–7.41 (m, 15H, Ar—H, T—H); 11.24 (s, 1H, NH).

10) Diethyl N-thymin-1-yl-acetyl-N-(2-hydroxy) ethylaminomethanephosphonate

The systhesis was carried out analogously to Example 4 from diethyl N-thymin-1-yl-acetyl-N-(4-methoxytriphenylmethoxy)ethylaminomethanephosphonate (Example 8). To purify it, the product was chromatographed on silica gel (EA/methanol 90:10). Yield: 80%.
MS (FAB): 400:1 (M+Na)$^+$; 378.1 (M+H)$^+$. $^1$H-NMR (200 MHz, DMSO, TMS): δ=1.17–1.32 (m, 6H, CH$_2$—CH$_3$); 1.78 (s, 3H, T—CH$_3$); 3.40–3.69 (m, 4H, CH$_2$—OH+N—CH$_2$); 3.89 (d, J=11 Hz, 2H, P—CH$_2$); 3.92–4.19 (m, 4H, PO—CH$_2$); 4.70 (s, 2H, CO—CH$_2$); 4.98 (t, 1H, OH); 7.22 & 7.30 (in each case s, 1H, T—H); 11.25 (s, 1H, NH).

11) Diphenyl N-(4-methoxytriphenylmethoxy) ethylaminomethanephosphonate

The synthesis was carried out analogously to Example 1f, but using diethyl phosphite. Yield: 100%.
MS (FAB): 58.2 (M+Li)$^+$.

12) N-Thymin-1-yl-acetyl-N-(4-methoxytriphenylmethoxy)ethylaminomethanephosphonic acid monophenyl ester (triethylammonium salt)

The synthesis was carried out analogously to Example 81 from diphenyl N-(4-methoxytriphenylmethoxy) ethylaminomethanephosphonate (Example 11) and thymidin-1-yl-acetic acid. To purify it, the product was chromatographed on silica gel (EA/methanol/TEA/H$_2$O 90:10:5:0.5). Yield: 47%.
MS (FAB): 682.3 (M+2Li—H)$^+$. $^1$H-NMR (200 MHz, DMSO, TMS): δ=1.16 (t, 9H, N—CH$_2$—CH$_3$); 1.67 & 1.72 (in each case s, 3H, T—CH$_3$); 2.96–3.70 (m, 12H, N—CH$_2$—CH$_3$+N—CH$_2$+P—CH$_2$+CH$_2$—OMMTr); 3.75 (s, 3H, OCH$_3$); 4.58 & 4.88 (in each case s, 2H, CO—CH$_2$); 6.74–7.46 (m, 20H, Ar—H, T—H); 11.23 (s, 1H, NH).

13) Phenyl 4-nitrophenylethyl N-thymin-1-yl-acetyl-N-(4-methoxytriphenylmethoxy) ethylaminomethanephosphonate 385.4 mg (0.5 mmol) of N-thymin-1-yl-acetyl-N-(4-methoxytriphenylmethoxy)ethylaminomethanephosphonic acid monophenyl ester (triethylammonium salt) (Example 12) and 92 mg (0.55 mmol) of 4-nitrophenylethanol were coevaporated three times with absol. pyridine, then dissolved in 15 ml of absol. pyridine. 403.4 mg (0.15 mmol) of 3-nitro-1-(p-toluenesulfonyl)-1H-1,2,4-triazole (TSNT) were added at 0° C., then the mixture was stirred at 0–5° C. for 16 h, the pyridine was distilled off in vacuo, the residue was taken up in EA and the solution was washed successively with saturated aqueous NaHCO$_3$ solution, then with NaCl solution. To purify it, the product was charomatographed on silica gel (EA/TEA 100:2). The yield was 162 mg.

MS (FAB): 831.3 (M+2Li—H)$^+$; (M+Li)$^+$.

14) Di(2-(p-nitrophenyl)ethyl) N-thymin-1-yl-acetyl-N-(4-methoxytriphenylmethoxy)ethylaminomethanephosphonate The synthesis was carried out analogously to Example 8 from di-(2-(p-nitrophenyl)ethyl) N-(4-methoxytriphenylmethoxy)ethylaminomethanephosphonate (Example 1f) and thymidin 1-yl-acetic acid. Yield: 63%

MS (ES+): 898.4 (M+Li)$^+$. $^1$H-NMR (200 MHz, DMSO, TMS): δ=1.65 & 1.72 (in each case s, 3H, T—CH$_3$); 2.96 (t, 4H, P—O—CH$_2$—CH$_2$—Ar); 3.06 (t, 2H, N—CH$_2$); 3.67 (d, J=11 Hz, 2H, P—CH$_2$); 3.70 (m, 2H, MMTr—O—CH$_2$); 3.75 (s, 3H, OCH$_3$); 3.83 (s, 3H, OCH$_3$); 4.10 (dt, 4H, P—O—CH$_2$); 4.59 & 4.62 (in each case s, broad, 2H, CO—CH$_2$); 6.83–8.18 (m, 23H, Ar—H, T—H); 11.30 (s, broad, 1H, NH).

15) N-Thymin-1-yl-acetyl-N-(4-methoxytriphenylmethoxy)ethylaminomethanephosphonic acid 4-nitrophenylethyl monoester (triethylammonium salt)

15a) From 30 mg of phenyl 4-nitrophenylethyl N-thymin-1-yl-acetyl-N-(4-methoxytriphenylmethoxy)ethylaminomethanephosphonate (Example 13)

30 mg of phenyl 4-nitrophenylethyl N-thymin-1-yl-acetyl-N-(4-methoxytriphenylmethoxy)ethylaminomethanephosphonate (Example 13) were dissolved in a mixture of 1 ml of TEA, 1 ml of dioxane and 80 mg of p-nitrobenzaldoxime and the solution was stirred at room temperature for 3 h. The solvent was evaporated in vacuo and the residue was coevaporated three times with pyridine and twice with toluene. The residue was chromatographed on silica gel (EA/TEA 100:2, then EA/methanol/TEA 60:40:2). The yield was 23 mg.

MS (FAB): 755.3 (M+2Li—H)$^+$. $^1$H-NMR (200 MHz, DMSO, TMS): δ=1.15 (t, 9H, N—CH$_2$—CH$_3$); 1.60 & 1.79 (m, 3H, T—CH$_3$); 2.80–3.60 (m, 14H, N—CH$_2$—CH$_3$+N—CH$_2$+P—CH$_2$+CH$_2$—OMMTr+Ar—CH$_2$); 3.73 (s, 3H, OCH$_3$); 4.01 (dt, 2H, P—O—CH$_2$); 4.58–4.92 m, 2H CO—CH$_2$); 6.82–8.18 (m, 19H, Ar—H, T—H); 11.30 (s, 1H, NH).

15b) From di(2-(p-nitrophenyl)ethyl) N-thymin-1-yl-acetyl-N-(4-methoxytriphenylmethoxy)ethylaminomethanephosphonate (Example 14)

The synthesis was carried out analogously to Example 3 from di(2-(p-nitrophenyl)ethyl) N-thymin-1-yl-acetyl-N-(4-methoxytriphenylmethoxy)ethylaminomethanephosphonate (Example 14), but in pyridine as a solvent. Yield: 82%. Spectrascopic data: see Example 15a.

16) N-Thymin-1-yl-acetyl-N-(4-methoxytriphenylmethoxy)ethylaminomethanephosphonic acid The synthesis was carried out analogously to Example 15b. N-thymin-1-yl-acetyl-N-(4-methoxytriphenylmethoxy)ethylaminomethanephosphonic acid is obtained in 18% yield as a by-product.

MS (ES−): 592.2 (M−H)$^−$.

17) 5'-MMTr-T-P(O-ethyl)-T-P-(O-ethyl)$_2$ 361 mg (0.5 mmol) of N-thymin-1-yl-acetyl-N-4-methoxytriphenylmethoxy)ethylaminomethanephosphonic acid monoethyl ester (triethylammonium salt) (9) and 188.7 mg (0.5 mmol) of diethyl N-thymin-1-yl-acetyl-N-(2-hydroxy)ethylaminomethanephosphonate (10) were coevaporated together twice with absol. pyridine, then dissolved in 10 ml of absol. pyridine. 1.5 mmol of TSNT were added at 5–10° C. and the mixture was stirred at room temperature for 16 h. The pyridine was evaporated in vacuo, the residue was dissolved in EA and the solution was washed successively with saturated aqueous NaHCO$_3$ solution, then NaCl solution. It was dried over Na$_2$SO$_4$, concentrated and to purify the residue it was chromatographed on silica gel (EA/methanol/TEA 92:8:2). The yield was 223 mg (46%).
MS (FAB): 987.5 (M+Li)$^+$. $^1$H-NMR (200 MHz, DMSO, TMS) Characteristic signals are: Ar—H & thymine-H: 6.82–7.43 (m, 16H); CO—CH$_2$: 4.59–4.78 (m, 4H); thymine-CH$_3$: 1.63–1.80 (m, 6H).

18) 5'-HO-T-P(O-phenyl)-T-P(O-ethyl)$_2$

The synthesis was carried out analogously to Example 4 from 5'-MMTr-T-P(O-ethyl-T-P(O-ethyl)$_2$ (Example 17). To purify the product, it was chromatographed on silica gel (EA/methanol/TEA 85:15:2, then 100:50:1.5). The yield was 95%.

MS (FAB): 731.2 (M+Na)$^+$ 709.1. (M+Li)$^+$. $^1$H-NMR (200 MHz, DMSO, TMS) Characteristic signals are: thymine-H: 7.21–7.36 (m, 2H); CO—CH$_2$: 4.60–4.76 (m, 4H); thymine-CH$_3$: 1.63–1.79 (m, 6H).

19) 5'-MMTr-T-P(O-phenyl)-T-P(O-ethyl)$_2$

The synthesis was carried out analogously to Example 17 from diethyl N-thymin-1-yl-acetyl-N-(2-hydroxy)ethylaminomethanephosphonate (Example 10) and N-thymin-1-yl-acetyl-N-(4-methoxytriphenylmethoxy)ethylaminomethanephosphonic acid monophenyl ester (triethylammonium salt) (Example 12). To purify the product, it was chromatographed on silica gel (EA/methanol/TEA 93:7:2). Yield: 58%.

MS (FAB): 1051.4 (M+Na)$^+$; 1029.5 (M+H)$^+$. $^1$H-NMR (200 MHz, DMSO, TMS) Characteristic signals are: Ar—H & thymine-H: 6.82–7.53 (m, 21H); CO—CH$_2$: 4.52–4.82 (m, 4H); thymine-CH$_3$: 1.62–1.80 (m, 6H).

20) Di(4-nitrophenylethyl N-thymin-1-yl-acetyl-N-(2-hydroxyethyl)aminomethanephosphonate The synthesis was carried out analogously to Example 4 from di(2-(p-nitrophenyl)ethyl) N-thymin-1-yl-acetyl-N-(4-methoxytriphenylmethoxy)ethylaminomethanephosphonate (Example 14). To purify the product, it was chromatographed on silica gel (EA/methanol 90:10). Yield: 85%.

MS (ES+): 620.3 (M+H)$^+$. $^1$H-NMR (500 MHz, DMSO, TMS): δ=1.73 (s, 3H, T—CH$_3$); 2.97 (t, 4H, P—O—CH$_2$—CH$_2$—Ar); 3.41 (m, 2H, N—CH$_2$); 3.59 (m, 2H, CH$_2$—OH); 3.83 (d, 2H, J=11 Hz; P—CH$_2$); 4.08–4.30 (m, 4H, P—O—CH$_2$); 4.54 & 4.78 (in each case s, broad, 2H, CO—CH$_2$); 4.99 (t, 1H, OH); 7.14–8.19 (m, 9H, Ar—H, thymidinyl-H); 11.30 (s, broad, 1H, NH).

21) 5'-MMTr-T-P(ONPE)-T-P(O-ethyl)$_2$

The synthesis was carried out analogously to Example 17 from diethyl N-thymin-1-yl-acetyl-N-(2-hydroxy)ethylaminomethanephosphonate (Example 10) and N-thymin-1-yl-acetyl-N-(4-methoxytriphenylmethoxy)ethylaminomethanephosphonic acid 4-nitrophenylethyl monoester (triethylammonium salt) (Example 15). Instead of TSNT, 3-nitro-1-(2,4,6-triisopropylphenylsulfonyl)-1H-1,2,4-triazole (TIPSNT) was employed for the coupling. To purify the product, it was chromatographed on silica gel (EA/methanol/TEA 95:5:2, then 90:10:2). Yield: >90%.

MS (ES+): 1109.0 (M+Li)$^+$. $^1$H-NMR ( 200 MHz, DMSO, TMS) Characteristic signals are: Ar—H & thymine-H: 6.82–8.18 (m, 20H); CO—CH$_2$: 4.51–4.76 (m, 4H); thymine-CH$_3$: 1.61–1.78 (m, 6H).

22) 5'-MMTr-T-P(ONPE)-T-P(OEt)$_2$

The synthesis was carried out analogously to Example 21 from diethyl N-thymin-1-yl-acetyl-N-(2-hydroxy) ethylaminomethanephosphonate (Example 10) and N-thymin-1-yl-acetyl-N-(4-methoxytriphenylmethoxy) ethylaminomethanephosphonic acid 4-nitrophenylethyl monoester (triethylammonium salt) (Example 15). Instead of TSNT, 3-nitro-1-(2,4,6-triisopropylphenylsulfonyl)-1H-1,2,4-triazole (TIPSNT) was employed for the coupling Yield: >90%.

For spectroscopic data see Example 21.

23) 5'-HO-T-P(ONPE)-T-P(OEt)$_2$

Synthesis was carried out analogously to Example 4 from "5'-MMTr-T-P(ONPE)-T-P(OEt)$_2$" (Example 22). To purify the product, it was chromatographed on silica gel (EA/methanol/TEA 90:10:2, then 80:20:2). The yield was 75%. MS (ES+): 836.3 (M+Li)$^+$. $^1$H-NMR (200 MHz, DMSO, TMS) Characteristic signals are: Ar—H & thymine-H: 7.11–8.22 (m, 6H); CO—CH$_2$: 4.55–4.77 (m, 4H); thymine-CH$_3$:1.71 (s, broad, 6H).

24) 5'-HO-T-P(OH)-T-P(O-ethyl)$_2$ 10 mg (0.012 mmol) of "5'-HO-T-P(ONPE)-T-P(OEt)$_2$" (Example 23) were dissolved in 1 ml of a 0.5M solution of DBU in pyridie and stirred first at 4° C. for 24 h, then at room temperature for 24 h. The solvent was evaporated in vacuo, and the residue was digested twice with pentane, then twice with ether, then to purify the product it was chromatographed on silca gel (EA/methanol/TEA 9:1:0.2, then 70:30:2, then 60:40:2). Yield: 10.2 mg.

MS (FAB): 725.3 (M+2Na—H)$^+$; 703.3 (M+Na)$^+$. $^1$H-NMR (200 MHz, DMSO, TMS) Characteristic signals are: thymine-H: 7.15–7.70 (m, 2H); CO—CH$_2$: 4.67–4.92 (m, 4H); thymine-CH$_3$: 1.67–1.81 (m, 6H).

25) 5'-MMTr-T-P(ONPE)-T-P(ONPE)-T-P(OEt)$_2$

The synthesis was carried out analogously to Example 17 from "5'-HO-T-P(ONPE)-T-P(OEt)$_2$" (Example 22) and N-thymin-1-yl-acetyl-N-(4-methoxytriphenylmethoxy) ethylaminomethanephosphonic acid 4-nitrophenylethyl monoester (triethylammonium salt) (Example 15) with addition of 1.5 eq (based on Example 23) of 4-methoxypyridine-N-oxide. To purify the product, it was chromatographed on silica gel (EA/methanol/TEA 90:10:2, then 85:15:2). Yield: 61%.

MS (ES+): 1555.8 (M+H)$^+$. $^1$H-NMR (200 MHz, DMSO, TMS) Characteristic signals are: Ar—H & thymine-H: 6.83–8.20 (m, 25H); CO—CH$_2$: 4.52–4.75 (m, 6H); thymine-CH$_3$: 1.61–1.78 (m, 9H).

26) 5'-HO-T-P-(ONPE)-T-P(ONPE)-T-P(OEt)$_2$

The synthesis was carried out analogously to Example 4 from "5'-MMTr-T-P(ONPE)-T-P(ONPE)-T-P(OEt)$_2$" (Example 25). To purify the product, it was chromatographed on silica gel (EA/methanol/TEA 70:30:2). The yield was 89%.

MS (ES+): 1283.1 (M+H)$^+$; 1305.0 (M+Na$^+$).

27) 5'-MMTr-T-P(ONPE)-T-P(ONPE)-T-P(ONPE)-T-P(OEt)$_2$

The synthesis was carried out analogously to Example 17 from "5'-HO-T-P-(ONPE)-T-P(ONPE)-T-P(OEt)$_2$" (Example 26) and N-thymin-1-yl-acetyl-N-(4-methoxytriphenylmethoxy)ethylaminomethanephosphonic acid 4-nitrophenylethyl monoester (triethylammonium salt) (Example 15) with addition of 1.5 eq (based on Example 23) of 4-methoxypyridine-N-oxide. To purify the product, it was chromatographed on silica gel (EA/methanol/TEA 90:10:2, then 80:20:2). Yield: 15%.

MS (ES+): 2007 (M+H)$^+$; 2029 (M+Na)$^+$. $^1$H-NMR (200 MHz, DMSO, TMS) Characteristic signals are: Ar—H & thymine-H: 6.79–8.21 (m, 30H); CO—CH$_2$: 4.53–4.87 (m, 8H); thymine-CH$_3$: 1.58–1.89 (m, 12H).

28) 5'-HO-T-P(ONPE)-T-P(ONPE)-T-P(ONPE)-T-P(OEt)$_2$

The synthesis was carried out analogously to Example 4 from "5'-MMTr-T-P(ONPE)-T-P(ONPE)-T-P(ONPE)-T-P(OEt)$_2$" (Example 27). To purify the product, it was chromatographed on silica gel (EA/methanol/TEA 70:30:2). The yield was 55%.

MS (FAB): 1735 (M+H)$^+$; 1757 (M+Na)$^+$.

29) 5'-MMTr-T-P(ONPE)-T-P(ONPE)$_2$

The synthesis was carried out analogously to Example 17 from di(4-nitrophenylethyl) N-thymin-1-yl-acetyl-N-(2hydroxyethyl)aminomethanephosphonate (Example 20) and N-thymin-1-yl-acetyl-N-(4-methoxytriphenylmethoxy) ethylaminomethanephosphonic acid 4-nitrophenylethyl monoester (triethylammonium salt) (Example 15). To purify the product, it was chromatographed on silica gel (EA/methanol/TEA 100:10:1, then 90:10:1). Yield: 87%.

MS (FAB): 1356.2 (M+2Li—H)$^+$. $^1$H-NMR (200 MHz, DMSO, TMS) Characteristic signals are: Ar—H & thymine-H: 6.82–8.18 (m, 28H); CO—CH$_2$: 4.50–4.71 (m, 4H); thymine-CH$_3$: 1.59–1.78 (m, 6H).

30) 5'-HO-T-P(ONPE)-T-P(ONPE)$_2$

The synthesis was carried out analogously to Example 4 from "5'-MMTr-T-P(ONPE)-T-P(ONPE)$_2$" (Example 29). To purify the product, it was chromatographed on silica gel (EA/methanol/TEA 85:15:1, then 80:20:1). The yield was 78%.

MS (ES+): 1072.7 (M+H)$^+$. $^1$H-NMR (200 MHz, DMSO, TMS) Characteristic signals are: Ar-H & thymine-H: 7.08–8.20 (m, 14H); CO—CH$_2$: 4.52–4.80 (m, 4H); thymine-CH$_3$: 1.70 (s, broad, 6H).

31) 5'-MMTr-C$^{An}$-P(ONPE)-C$^{An}$-P(ONPE)-C$^{An}$-P(ONPE)$_2$

The synthesis was carried out analogously to Example 17 from N-(N$^6$-anisoyl)cytosin-1-yl-acetyl-N-(4-methoxytriphenylmethoxy)ethylaminomethanephosphonic acid 2-(p-nitropyhenyl)ethyl monoester (triethylammonium salt) (Example 3) and "5'-HO-C$^{An}$-P(ONPE)-C$^{An}$-P(ONPE)$_2$" (Example 6). To purify the product, it was chromatographed on silica gel (EA/methanol/TEA 80:19:1). Yield: 66%.

MS (FAB): 2155 (M+H)$^+$; 2161 (M+Li)$^+$; 2177 (M+Na)$^+$.

32) 5'-HO-C$^{An}$-P(ONPE)-C$^{An}$-P(ONPE)-C$^{An}$-P(ONPE)$_2$

The synthesis was carried out analogously to Example 4 from "5'-MMTr-C$^{An}$-P(ONPE)-C$^{An}$-P(ONPE)-C$^{An}$-P(ONPE)$_2$" (Example 31). To purify the product, it was chromatographed on silica gel (EA/methanol/TEA 85:15:1, then 80:20:1). The yield was 70%.

MS (FAB): 1882 (M+H)$^+$; 1904 (M+Na)$^+$.

33) Allyl 2-(p-nitrophenyl)ethyl N-(N$^6$-anisoyl)cytosin-1-yl-acetyl-N-(4-methoxytriphenylmethoxy) ethylaminomethanephosphonate The synthesis was carried out analogously to Example 17 from N-(N$^6$-anisoyl)cytosin-1-yl-acetyl-N-(4-methoxytriphenylmethoxy)ethylaminomethanephosphonic acid 2-(p-nitrophenyl)ethyl monoester (triethylammonium salt) (Example 3) and allyl alcohol. To purify the product, it was chromatographed on silica gel (EA/methanol/TEA 95:5:1).

MS (ES+): 902.1 (M+H)$^+$; 924.1 (M+Na)$^+$. $^1$H-NMR (200 MHz, DMSO, TMS): δ=2.94–3.70 (m, 8H, P—O—CH$_2$—

Ar+MMTr—O—CH$_2$+N—CH$_2$+P—CH$_2$); 3.75 (s, 3H, OCH$_3$); 3.86 (s, 3H, OCH$_3$); 4.10–4.60 (m, 4H, P—O—CH$_2$); 4.79 & 4.84 (in each case s, broad, 2H, CO—CH$_2$); 5.09–5.39 (m, 2H, H$_2$C=CH—); 5.71–6.00 (m, 1H, H$_2$C=CH—); 6.83–8.19 (m, 24H, Ar—H, cytosinyl-H); 11.03 (s, broad, 1H, NH).

34) Allyl 2-(p-nitrophenyl)ethyl N-(N$^6$-anisoyl)cytosin-1-yl-acetyl-N-(2-hydroxy)ethylaminomethanephosphonate The synthesis was carried out analogously to Example 4 from allyl 2-(p-nitropyenyl)ethyl N-(N$^6$-anisoyl)cytosin-1-yl-acetyl-N-(4-methoxytriphenylmethoxy) ethylaminomethanephosphonate (Example 33). To purify the product, it was chromatographed on silica gel (EA/methanol/TEA 94:5:1). The yield was 83%.

MS (ES+): 630.2 (M+H)$^+$. $^1$H-NMR (200 MHz, DMSO, TMS): δ=3.02 (t, 2H, P—O—CH$_2$—CH$_2$—Ar); 3.37–3.72 (m, 4H, HO—CH$_2$CH$_2$); 3.86 (s, 3H, OCH$_3$); 3.91 (d, J=11 Hz, 2H, P—CH$_2$); 4.22 (dt, 2H, P—O—CH$_2$—CH$_2$—Ar); 4.40 (dd, 2H, O—CH$_2$—CH=CH$_2$); 4.78 & 501 (m, 2H, CO—CH$_2$); 5.11–5.33 (m, 2H, H$_2$C=CH—); 5.71–6.00 (m, 1H, H$_2$C=CH—); 6.99–8.21 (m, 14H, Ar—H, cytosinyl-H); 11.03 (s, broad, 1H, NH).

35) Allyl 2-(p-nitrophenyl)ethyl N-thymin-1-yl-acetyl-N-(4-methoxytriphenylmethoxy) ethylaminomethanephosphonate The synthesis was carried out analogously to Example 17 from N-thymin-1-yl-acetyl-N-(4-methoxytriphenylmethoxy)ethylaminomethanephosphonic acid 4-nitrophenylethyl monoester (triethylammonium salt) (Example 15) and allyl alcohol. To purify the product, it was chromatographed on silica gel (EA/methanol/TEA 97:3:2). The yield was 100%.

MS (FAB): 805.3 (M+Na)$^+$.

36) Allyl 2-(p-nitrophenyl)ethyl N-thymin-1-yl-acetyl-N-(2-hydroxy)ethylaminomethanephosphonate Synthesis analogously to Example 4 from allyl 2-(p-nitrophenyl)ethyl N-thymin-1-yl-acetyl-N-(4-methoxytriphenylmethoxy)ethylaminomethanephosphonate (Example 35). to purify the product, it was chromatographed on silica gel (EA/methanol/TEA 90:10:2). The yield was 86%.

MS (ES+): 511.1 (M+H)$^+$ 37) 5'-MMTr-T-P(ONPE)-T-P(ONPE) (O-allyl)

Synthesis analogously to Example 17 from allyl 2-(p-nitrophenyl)ethyl N-thymin-1-yl-acetyl-N-(2-hydroxy)ethylaminomethanephosphonate (Example 36) and N-thymin-1-yl-acetyl-N-(4-methoxytriphenylmethoxy) ethylaminomethanephosphonic acid 4-nitrophenylethyl monoester (triethylammonium salt) (Example 15). To purify the product, it was chromatographed on silica gel (EA/methanol/TEA 90:10:2). Yield: 90%.

MS (FAB): 1257.3 (M+Na)$^+$.

38) 5'-MMTr-T-P(ONPE)-T-P(ONPE)-T-P(ONPE)-T-P(ONPE)-T-P(OEt)$_2$

Synthesis analogously to Example 17 from "5'-HO-T-P(ONPE)-T-P(ONPE)-T-P(ONPE)-T-P(OEt)$_2$" (Example 28) and N-thymin-1-yl-acetyl-N-(4-methoxytriphenylmethoxy) ethylaminomethanephosphonic acid 4-nitrophenylethyl monoester (triethylammonium salt) (Example 15). To purify the product, it was chromatographed on silica gel (EA/methanol/TEA 80:20:2). Yield: 57%.

MS (FAB): 2460 (M+H)$^+$; 2482 (M+Na)$^+$.

39) 5'-HO-T-P(ONPE)-T-P(ONPE)-T-P(ONPE)-T-P(ONPE)-T-P(OEt)$_2$

Synthesis analogously to Example 4 from "5'-MMTr-T-P(ONPE)-T-P(ONPE)-T-P(ONPE)-T-P(ONPE)-T-P(OEt)$_2$" (Example 38). To purify the product, it was chromatographed on silica gel (EA/methanol/TEA 70:30:2). The yield was 55%.

MS (FAB): 2209 (M+Na)$^+$.

40) 5'-HO-T-P(OH)-T-P(OH)-T-P(OH)-T-P(OH)-T-P(OEt)$_2$ 4.0 mg (0.00183 mmol) of "5'-HO-T-P(ONPE)-T-P(ONPE)-T-P(ONPE)-T-P(ONPE)-T-P(OEt)$_2$" (Example 39) were dissolved in 1.1 ml of a 0.5 molar solution of DBU in pyridine and stirred at room temperature for 24 h. The reaction mixture was evaporated in acuo and the residue was stirred several times with toluene. The solvent was removed using a syringe, the residue was stirred again with pentane, and the solvent was removed again using a syringe. The product was dried in vacuo. The yield was 4 mg of a strongly hygroscopic powder.

MS (ES–): 1589.7 (M–H$^-$)$^-$; 1611.8 (M+Na—2H)$^-$.

41) 5'-MMTr-T-P(ONPE)-T-P(ONPE)-T-P(ONPE)-T-P(ONPE)-T-P(ONPE)-T-P(OEt)$_2$ a) Synthesis analogously to Example 17 from "5'-HO-T-P(ONPE)-T-P(ONPE)-T-P(ONPE)-T-P)ONPE)-T-P(OEt)$_2$" (Example 39) and N-thymin-1-yl-acetyl-N-(4-methoxytriphenylmethoxy) ethylaminomethanephosphonic acid 4-nitrophenylethyl monoester (triethylammonium salt) (Example 15). To purify the product, it was chromatographed on silica gel (EA/methanol/TEA 80:20:2, then 70:30:2).

MS (FAB): 2934 (M+Na)$^+$, 2957 (M+2Na—H)$^+$, 2978 (M+3Na—2H)$^+$.

b) Synthesis analogously to Example 17 from "5'-HO-T-P(ONPE)-T-P(ONPE)-T-P(ONPE)-T-P(OEt)$_2$" (Example 28) and "5'-MMTr-T-P(ONPE)-T-P(ONPE) (OH)" (Example 42). To purify the product, it was chromatographed on silica gel (EA/methanol/TEA 80:20:2, then 70:30:2). The target fraction was evaporated in vacuo, then triturated with pentane and ether. MS as above.

42) 5'-MMTr-T-P(ONPE)-T-P(ONPE) (OH)

24.7 mg (0.02 mmol) of "5'-MMTr-T-P(ONPE) (O-allyl)" (Example 37 ) were dissolved in 2 ml of absol. DCM together with 16.2 mg (0.12 mmol) of diethylammonium hydrogencarbonate. At 15–20° C., a solution of 13.9 mg (0.012 mmol) of tetrakis(triphenylphosphine) palladium (0) and 2.1 mg (0.008 mmol) of triphenylphosphine in 2 ml of absol. DCM was added dropwise during the course of 2 min. The mixture was stirred at room temp. for 30 min. To purify the product, the reaction mixture was chromatographed on silica gel (Ea/methanol/TEA 80:20:1, then 60:40:1). The product fraction was evaporated in vacuo, and the residue was triturated with pentane, then with EA/ether, then again with pentane and dried in vacuo. Yield: 57%.

MS (ES–): 1993.6 (M–H)$^-$.

$^1$H-NMR (200 MHz, DMSO, TMS): characteristic signals: δ=1.67 & 1.72 (in each case s, 3H, T—CH$_3$); 4.60 & 4.82 (in each case s, 2H, CO—CH$_2$); 6.83–8.19 (m, 24H, Ar—H, T—H);

43) 5'-HO-T-P(ONPE)-T-P(ONPE)-T-P(ONPE)-T-P(ONPE)-T-P(ONPE)-T-P(OEt)$_2$

Synthesis analogously to Example 4 from "5'-MMTr-T-P(ONPE)-T-P (ONPE)-T-P(ONPE)-T-P(ONPE)-T-P(ONPE)-T-P(OEt)$_2$" (Example 41). After reaction had taken place, the reaction mixture was concentrated, and the residue was coevaporated three times with toluene, then stirred, first with EA/ether, then with pentane. The residue was dried in vacuo.

MS (FAB): 2662 (M+Na)$^+$·

44) 5'-HO-T-P(ONPE)-T-P(ONPE) (O-allyl)

Synthesis analogously to Example 4 from 5'-MMTr-T-P(ONPE)-T-P(ONPE) (O-allyl) (Example 37). To purify the product, it was chromatographed on silica gel (EA/methanol/TEA 90:10:1, then 80:20:1). The yield was 87%. MS (FAB): 963.0 (M+H)⁺; 985.1 (M+Na)⁺.

45) 5'-MMTr-T-P(ONPE)-T-P(ONPE)-T-P(ONPE) (OH)

a) 5'-MMTr-T-P(ONPE)-T-P(ONPE)-T-P(ONPE) (O-allyl)

Synthesis analogously to Example 17 from "5-HO-T-P(ONPE)-T-P(ONPE) (O-allyl)" (Example 44) and N-thymin-1-yl-acetyl-N-(4-methoxytriphenylmethoxy)ethylaminomethanephosphonic acid 4-nitrophenylethyl monoester (triethylammonium salt) 4-nitrophenylethyl monoester (triethylammonium salt) (Example 15). To purify the product, it was chromatographed on silica gel (EA/methanol/TEA 90:10:1, then 85:15:1). Yield: 55% b) 5'-MMTr-T-P(ONPE)-T-P(ONPE)-T-P(ONPE) (OH)

"5'-MMTr-T-P(ONPE)-T-P(ONPE)-T-P(ONPE) (O-allyl)" (Example 45a) was reacted with tetrakis(triphenylphosphine)palladium (O) as described in Example 42. To purify the product, it was chromatographed on silica gel (EA/methanol/TEA 80:20:2, then 70:30:2). The product fraction was evaporated in vacuo, and the residue was triturated with pentane and ether. Yield: 98%.

MS (ES+; LiCl): 1654.1 (M+Li⁺)

46) 5'-MMTr-T-P(ONPE)-T-P(ONPE)-T-P(OEt)₂

Synthesis analogously to Example 17 from diethyl N-thymin-1-yl-acetyl-N-(2-hydroxy)ethylaminomethanephosphonate (Example 10) and "5'-MMTr-T-P(ONPE)-T-P(ONPE)-T-P(ONPE) (OH)" (Example 45b). To purify the product, it was chromatographed on silica gel (EA/methanol/TEA 90:10:2, then 80:20:2). Working up, purification and characteristics as in Example 27.

47) 5'-MMTr-T-P(ONPE)-T-P(ONPE)-T-P(ONPE)-T-P(ONPE)-T-P(OEt)₂

Synthesis analogously to Example 17 from "5'-HO-T-P-(ONPE)-T-P(ONPE)-T-P(OEt)₂" (Example 26) and "5'-MMTr-T-P(ONPE)-T-P(ONPE)-T-P(ONPE (OH)" (Example 45b). To purify the product, it was chromatographed on silica gel (EA/methanol/TEA 80:20:2). The product fraction was evaporated in vacuo, coevaporated with toluene and purified by preparative HPLC (high-pressure liquid chromatography): RP8 LiChrospher 60, water/acetonitrile/:1:1, 0.1% ammonium acetate; 1 ml/min. R_f=12.97 min.

48) 5'-HO-T-P(OH)-T-P(OH)-T-P(OH)-T-P(OH)-T-P-(OH)-T-P(OEt)₂ a) 5'-HO-T-P(ONPE)-T-P(ONPE)-T-P(ONPE)-T-P(ONPE)-T-P(ONPE)-T-P(OEt)₂

Synthesis analogously to Example 4 from "5'-MMTr-T-P(ONPE)-T-P-(ONPE)-T-P(ONPE)-T-P(ONPE)-T-P(ONPE)-T-P(OEt)₂" (Example 47). To purify the product, it was chromatographed on silica gel (EA/methanol/TEA 70:30:2, then 60:40:2). The product fraction was evaporated in vacuo, and the residue was stirred, first with pentane, then with ether, and dried in vacuo. Yield: 100%.

MS (FAB): 2662 (M+Na)⁺, 2684 (M+2Na—H)⁺, 2706 (M+3Na—2H)⁺.

b) 5'-HO-T-P(OH)-T-P(OH)-T-P(OH)-T-P(OH)-T-P-(OH)-T-P-(OEt)₂

"5'-HO-T-P(ONPE)-T-P(ONPE)-T-P(ONPE)-T-P(ONPE)-T-P(ONPE)-T-P(OEt)₂" (Example 48a) was reacted with DBU and worked up analogously to Example 40.

MS (ES-): 1892 (M-H⁻); 1915 (M+Na-2H)⁻.

49) 5'MMTr-T-P(ONPE)-T-P(ONPE)-T-P(ONPE)-T-P(ONPE)-T-P(ONPE)-T-P(OEt)₂

Synthesis analogously to Example 17 from "5'-HO-T-P(ONPE)-T-P(ONPE)-T-P(ONPE)-T-P(OEt)₂" (Example 28) and "5'-MMTr-T-P(ONPE)-T-P(ONPE)-T-P(ONPE) (OH)" (Example 45b). To purify the product, it was chromatographed on silica gel (EA/methanol/TEA 80:20:2, then 70:30:2). The product fraction was evaporated in vacuo, coevaporated with toluene and purified by preparative HPLC:RP8 LiChrospher 60, water/acetonitrile: 1:1; 0.1% ammonium acetate; 1 ml/min, R_f=15.24 min.

MS (FAB): 3386 (M+Na)⁺, 3409 (M+2Na–H)⁺, 50) 5'-HO-T-P(ONPE)-T-P(ONPE)-T-P(ONPE)-T-P(ONPE)-T-P(ONPE)-T-P(ONPE)-T-P(OEt)₂

Synthesis analogously to Example 4 from "5'MMTr-T-P(ONPE)-T-P(ONPE)-T-P(ONPE)-T-P(ONPE)-T-P(ONPE)-T-P-(ONPE)-T-P(OEt)₂" (Example 49). To purify the product, it was evaporated in vacuo and coevaporated three times with toluene, and the residue was stirred, first with pentane, then with ether, and dried in vacuo. Yield: >90%.

MS (FAB): 3114 (M+Na)⁺

51) 5'-HO-T-P(OH)-T-P(OH)-T-P(OH)-T-P(OH)-T-P-(OH)-T-P(OH)-T-P(OEt)₂

"5'-HO-T-P(ONPE)-T-P(ONPE)-T-P(ONPE)-T-P(ONPE)-T-P-(ONPE)-T-P(OEt)₂" (Example 50) was reacted with DBU and worked up analogously to Example 40.

MS (ES-): 2196 (M-H⁺)⁻; 2218 (M+Na-2H)-.

52) 5'-MMTr-T-P(ONPE)-T-P(ONPE)-T-P(ONPE)-T-P(ONPE)-T-P(ONPE)-T-P-(ONPE)-T-P(ONPE)-T-P-(ONPE)-T-P(OEt)₂

Synthesis analogously to Example 17 from "5'-HO-T-P(ONPE)-T-P(ONPE)-T-P(ONPE)-T-P(ONPE)-T-P(ONPE)-T-P(OEt)₂" (Example 48a) and "5'-MMTr-T-P(ONPE)-T-P(ONPE)(OH)" (Example 45b). To purify the product, it was chromatographed on silica gel (EA/methanol/TEA 70:30:2, then 60:40:2). The product fraction was evaporated in vacuo, coevaporated with toluene and purified by preparative HPLC: RP8 LiChrospher 60, water/acetonitrile: 1:1; 0.1% ammonium acetate; 1 ml/min. R_f=23.95 min.

53) 5'-HO-T-P(OH)-T-P(OH)-T-P(OH)-T-P(OH)-T-P-(OH)-T-P(OH)-T-P-(OH)-T-P(OH)-T-P(OEt)₂ a) 5'-HO-T-P(ONPE)-T-P(ONPE)-T-P(ONPE)-T-P(ONPE)-T-P(ONPE)-T-P(ONPE)-T-P(ONPE)-T-P(ONPE)-T-P(OEt)₂

Synthesis analogously to Example 4 from "5'-MMTr-T-P(ONPE)-T-P(ONPE)-T-P(ONPE)-T-P(ONPE)-T-P(ONPE)-T-P-(ONPE)-T-P-(ONPE)-T-P-(ONPE)-T-P(OEt)₂" (Example 52). To purify the product, it was evaporated in vacuo and coevaporated three times with toluene, and the residue was stirred, first with pentane, then with ether, and dried in vacuo. Yield: <90%.

b) "5'-HO-T-P(OH)-T-P(ONPE)-T-P(ONPE)-T-P(ONPE)-T-P(ONPE)-T-P(ONPE)-T-P(ONPE)-T-P(ONPE)-T-P(ONPE)-T-P(OEt)₂" (Example 53a) was reacted with DBU and worked up analogously to Example 40.

MS (ES-): 2802 (M-H⁻)⁻; 2825 (M+NA-2H)⁻.

54) Di(2-(p-nitrophenyl)ethyl) 2-(N'-tert-butoxycarbonylamino)ethylaminomethanephosphonate a) 1-Methylimino-2-(N'-tert-butoxycarbonylamino)ethane (trimer)

2.0 g (12.5 mmol) of 2-amino-1-(N'-tert-butoxycarbonylamino)ethane, dissolved in 8 ml of methanol, were treated with ice cooling with 1.52 ml (18.72 mmol) of 37% formaldehyde and the mixture was stirred at room temp. for 1 h. The residue was taken up in EA, washed twice with saturated NaHCO₃ solution, then with NaCl solution, dried, filtered and evaporated in vacuo. To purify the product, it was chromatographed on silica gel (EA/TEA 100:0.2, then EA/methanol/TEA 90:10:0.2). The yield was 0.8 g.

MS (FAB/LiCl) 523.4 (M+2Li—H)$^+$. $^1$H-NMR (200 MHz, DMSO, TMS): δ=1.38 (s, 27H, tBu-H); 2.40 (t, 6H, N-CH$_2$); 2.99 (t, 6H, N-CH$_2$); 3.25 (t, 6H, N-CH$_2$); 6.81 (t, broad, 3H, NH).

b) 2-Di(2-(p-nitrophenyl)ethyl) 2-(N'-tert-butoxycarbonylamino)ethylaminomethanephosphonate 1-Methylimino-2-(N'-tert-butoxycarbonylamino)ethane (trimer) (Example 54a) was reacted with di(2-(4-nitrophenyl)ethyl) phosphite (Example 1e) analogously to Example 1f. To purify the product, it was chromatographed on silica gel (first toluene/EA/TEA 20:80:0.2; then EA/TEA 100:0.2, then EA/methanol/TEA 0.5:5:0.2). Yield: 25%.

MS(ES+LiCl) 553.3 (M+H)$^+$, 559.3 M+Li)$^+$, $^1$H-NMR (200 MHz, DMSO, TMS): δ=1.37 (s, 9H, tBu-H); 2.83 (d, J=12 Hz, 2H, P-CH$_2$); 2.55 (t, 4H, Ar-CH$_2$); 2.90–3.09 (m, 4H, N-CH$_2$—CH$_2$-N); 4.16 (dt, 4H, PO-CH$_2$); 7.52 & 8.15 (in each case d, 8H, Ar-H).

55) Di-(2-(p-nitrophenyl)ethyl N-thymin-1yl-acetyl-N-(2-N'-tert-butoxycarbonylamino)ethylaminomethanephosphonate Synthesis analogously to Example 8 from di(2-(p-nitrophenyl)ethyl) 2-(N'-tert-butoxycarbonylamino)ethylamino-m-ethanephonate (Example 54b) and thymidin-1-yl-acetic acid.

Yield: 86%

MS (FAB/LiCl): 725.3 (M+Li)$^+$. $^1$H-NMR (200 MHz, DMSO, TMS): δ=1.42 (s, 9H, tBu-H); 1.91 (s, 3H, T-CH$_3$); 2.99–3.58 (m, 8H, P-O-CH$_2$-CH$_2$-Ar & N-CH$_2$—CH$_2$-N); 3.75 (d, J=12 Hz, 2H, P-CH$_2$); 4.06–4.38 (m, 4H, PO-CH$_2$); 7.37 & 8.15 (in each case d, 8H, Ar-H).

56) Interaction with DNA: UV melting curve

The interaction of the compounds according to the invention with complementary nucleic acids was demonstrated by way of example of the recording of the UV melting curve of "5'-HO-T-P(OH)-T-P(OH)-T-P(OH)-T-P(OH)-T-P-(OH)-T-P-(OH)-T-P-(OH)-T-P(OH)-T-P(OEt)$_2$" (Example 53b) with (dA)$_9$. To do this, a 0.3 OD of "5'-HO-T-P(OH)-T-P(OH)-T-P(OH)-T-P(OH)-T-P(OH)-T-P-(OH)-T-P(OH)-T-P(OEt)$_2$" and (dA)$_9$ in each case was prepared in 1 ml of a buffer (1M NaCl, 20 mM MgCl$_2$, 10 mM HEPES, pH 7.5) and the change in extinction at 260 nm was recorded as a function of the temperature (0 to 80° C.). The results can be seen in FIG. 1. A T$_m$ value of about 23° C. was determined from the melting curve obtained.

57) Interaction with DNA; gel shift experiment

Figure 2:
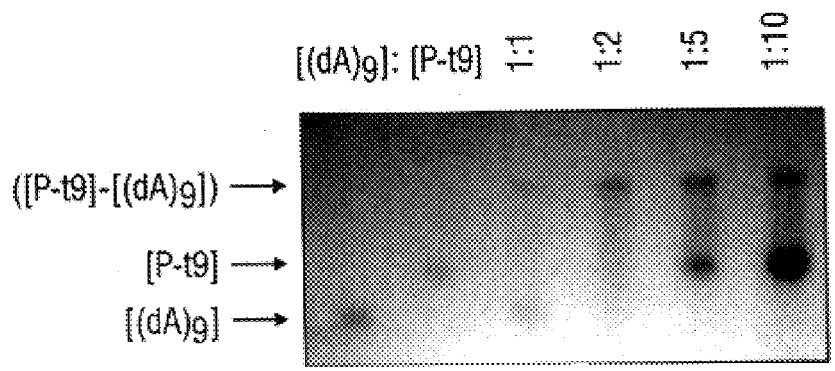
FIG. 2 is a chart showing proof of PMENA-DNA binding by Gel-Shift [See Example 57].

The interaction of the compounds according to the invention with complementary nucleic acids was demonstrated by way of example by the hybridization of "5'-HO-T-P(OH)-T-P(OH)-T-P(OH)-T-P-(OH)-T-P(OH)-T-P-(OH)-T-P(OH)-T-P(OEt)$_2$" (Example 53b) with (dA)$_9$ in a gel shift experiment. To do this, "5'-HO-T-P(OH)-T-P-(OH)-T-P (OH)-T-P(OH)-T-P-(OH)-T-P(OH)-T-P-(OH)-T-P(OH)-T-P (OEt)$_2$" (Example 53b) and (dA)$_9$ were in each case applied on their own and mixed in the ratio 1:1, 1:2, 1:5 and 1:10 to a nondenatured polyacrylamide gel (20%, running buffer 1×TBE, 10 mM MgCl$_2$) and the running behavior determined. The results can be seen in FIG. 2: (dA)$_9$ runs faster than "5'-HO-T-P(OH)-T-P(OH)-T-P(OH)-T-P(OH)-T-P-(OH)-T-P(OH)-T-P-(OH)-T-P(OH)-T-P(OEt)$_2$" and in the 1:1 mixture both can only be seen weakly, instead a slower band is formed which corresponds to a complex between the two components. In the 2:1 mixture, (dA)$_9$ can no longer be seen, instead the new band is all the more distinct. The same applies for the 5:1 or 10:1 mixture, in which additionally the distinct excess of "5'-HO-T-P(OH)-T-P(OH)-T-P(OH)-T-P (OH)-T-P-(OH)-T-P(OH)-T-P(OH)-T-P(OEt)$_2$" can be detected.

58) 5'-MMTr-T-P(ONPE)-T-P(OEthyl)$_2$ [see also Example 21, alternative syntheses]

a) 8.44 mg (10 μmol) of N-thymin-1-yl-acetyl-N-(4-methoxytriphenylmethoxy)ethylaminomethanephosphonic acid 4-nitrophenylethyl monoester (triethylammonium salt) (Example 15), 3.77 mg (10 μmol) of diethyl N-thymin-1-yl-acetyl-N-(2-hydroxy)ethylaminomethanephosphonate (Example 10) and 64.6 mg (500 μmol) of N-ethyldiisopropylamine (DIPEA) were dissolved in 0.3 ml of absol. DMF. 44.2 mg (100 μmol) of benzotriazolyloxy) tris(dimethylamino)phosphonium hexafluorophosphate (BOP) were added thereto. The mixture was stirred at room temp. for 24 h. About 70% yield according to TLC (EA/methanol/TEA 100:20:2; R$_f$=0.5).

b) Analogously to Example 58a, but using 30 μmol of HATU (O-(7-azabenzotriazol-1-yl)-N,N,N',N'-tetramethyluronium hexafluorophosphate) instead of 100 μmol of BOP. About 65% yield according to TLC.

59) 2-(p-Nitrophenyl)ethyl 5'-(3'-levuloyl)thymidine N-thymin-1-yl-acetyl-N-(4-methoxytriphenylmethoxy) ethylaminomethanephosphonate Synthesis according to Example 17 from N-thymin-1-yl-acetyl-N-(4-methoxytriphenylmethoxy)ethylaminomethanephosphonic acid 4-nitrophenylethyl monoester (triethylammonium salt, Example 15) and 3'-levuloylthymidine. To purify the product, it was chromatographed on silica gel (DCM/methanol/TEA 98:2:0.25). The yield was 46%.

MS (FAB/LiCl): 1071.4 (M+Li)$^+$.

60) N-Thymin-1-yl-acetyl-N-(4-methoxytriphenylmethoxy)ethylaminomethanephosphonic acid 2-(p-nitrophenyl)ethyl 5'-thymidine diester 64 mg (0.06 mmol) of 2-(p-nitrophenyl)ethyl 5'-(3'-levuloyl thymidine N-thymin-1-yl-acetyl-N-(4-methoxytriphenylmethoxy)ethylaminomethanephosphonate (Example 59) were dissolved in 0.5 ml of dioxane. 9 mg (0.23 mmol) of NaBH$_4$ in 0.12 ml of water were added and the mixture was stirred at room temperature for 20 min. The solvent was evaporated in vacuo, the residue was taken up in DCM, and the solution was extracted with water and dried. To purify the product, it was chromatographed on silica gel (DCM/methanol/TEA 92:8:0.5). The yield was 72%.

MS (FAB/LiCl): 973.4 (M+Li)$^+$, 979.4 (M+2Li–H)$^+$, 985.4 (M+3Li–2H)$^+$.

61) N-Thymin-1-yl-acetyl-N-(4-methoxytriphenylmethoxy)-ethylaminomethanephosphonic acid (2-(p-nitrophenyl)ethyl 5'-thymidin-3'-(cyanoethyl-N,N-diisopropyl phosphoramidite)

31 mg (0.032 mmol) of N-thymin-1-yl-acetyl-N-(4-methoxytriphenylmethoxy)ethylaminomethanephosphonic acid 2-(p-nitrophenyl)ethyl 5'-thymidine diester (Example 60) were coevaporated twice with absol. CH$_3$CN and dissolved in 0.4 ml absol. THF. First 12.4 mg (0.096 mmol) of diisopropylethylamine, then 9.8 mg (0.045 mmol) of cyanoethyl chlorodiisopropylphosphoramidite were added thereto. The mixture was stirred for 3 h, filtered and evaporated in vacuo. The yield was 63%.

MS (FAB/LiCl): 1173.3 (M+Li)$^+$, 1180.4 (M+2Li-H)$^+$, 1186.4 (M+3Li-2H)$^+$.

62) Di(2-p-nitrophenyl)ethyl) N-[N9-(O6-diphenylcarbamoyl-N2-acetylguanine]acetyl-N-(4-methoxytriphenyl-methoxy)ethylaminomethanephosphonate Synthesis analogously to Example 2 from di(2-p-nitrophenyl)ethyl N-(4-methoxytriphenylmethoxy)ethylamino-methanephosphonate (Example 1f) and O6-diphenylcarbamoyl-N2-acetylguanineacetic acid. To purify the product, it was chromatographed on silica gel (EA/TEA 98:2). Yield: 87%

MS (FAB/LiCl): 1154.8 (M+H)$^+$, 1160.7 (M+Li)$^+$.

63) Di(2-(p-nitrophenyl)ethyl, N-[N9-(N4-anisoyladenine]acetyl-N-(4-methoxytriphenylmethoxy) ethylaminomethane-phosponate Synthesis analogously to Example 2 from di(2-p-nitrophenyl)ethyl, N-(4-methoxytriphenylmethoxy) ethylaminomethanephosphonate (Example 1f) and N4-anisoyladenine-acetic acid. To purify the product, it was chromatographed on silica gel (DCM/methanol/TEA 95:4:1). Yield: 82%; MS (ES+): 1035.7 (M+H)$^+$. $^1$H-NMR (200 MHz, DMSO, TMS): δ=2.93 (t, 4H, P-O-CH$_2$—CH$_2$—Ar); 3.09 (t, 2H, MMTr—O—CH$_2$); 3.23–3.75 (m, 4H, P—CH$_2$+N—CH$_2$); 3.75 (s, 3H, OCH$_3$); 3.87 (s, 3H, OCH$_3$); 4.08 (dt, 4H, P—O—CH$_2$); 5.28–5.42 (m, 2H, CO—CH$_2$); 6.81–8.20 (m, 28H, Ar—H, A—H); 11.00 (s broad, 1H, NH).

64) N-[N9-(N4-Anisoyladenine]acetyl-N-(4-methoxytriphenylmethoxy)ethylaminomethanephosphonic acid mono(2-p-nitrophenyl)ethyl ester Synthesis analogously to Example 3 from di(2-(p-nitrophenyl)ethyl) N-[N9-(N4-anisoyladenine]acetyl-N-(4-methoxytriphenylmethoxy)ethylaminomethanephosphonate (Example 63). To purify the product, it was chromatographed on silica gel (EA/methanol/TEA 65:35:2). The yield was 52%.

MS (FAB/LiCl): 874.3 (M+2Li–H)$^+$.

65) Di(2-p-nitrophenyl)ethyl), N-thymin-1yl-acetyl-N-(2-methoxy)ethylaminomethanephosphonate Synthesis analogously to Example 2 from di(2-p-nitrophenyl)ethyl) N-(2-methoxy)ethylaminomethanephosphonate (prepared analogously to Example 1 starting from 2-methoxyethylamine by reaction with formaldehyde and di(2-(4-nitrophenyl)ethyl phosphite) and thymidin-1-yl-acetic acid. To purify the product, it was chromatographed on silica gel (EA/methanol 90:10). Yield: 64%

MS (FAB/LiCl): 640.3 (M+Li)$^+$.

66) 5'-MMTr-C$^{An}$-P(ONPE)-C$^{An}$-P(ONPE) (OAllyl)

Synthesis analogously to Example 17 from N-(N$^6$-anisoyl)-cytosin-1-yl-acetyl-N-(4-methoxytriphenylmethoxy)ethylaminomethanephosphonic acid (2-(p-nitrophenyl)ethyl) monoester (triethylammonium salt) (Example 3) and allyl 2-(p-nitrophenyl)ethyl N-(N$^6$-anisoyl)cytosin-1-yl-acetyl-N-(2-hydroxy) ethylaminomethanephosphonate (Example 34). To purify the product, it was chromatographed on silica gel (EA/methanol/TEA 85:14:1). Yield: 36%.

MS (FAB): 1474 (M+H)$^+$; 1496 (M+Na)$^+$.

67) 5'-HO-C$^{An}$-P(ONPE)-C$^{An}$-P(ONPE) (OAllyl)

Synthesis analogously to Example 4 from "5'-MMTr-C$^{An}$-P(ONPE)-C$^{An}$-P(ONPE) (OAllyl)" (Example 66). To purify the product, it was chromatographed on silica gel (EA/methanol/TEA 80:19:1). The yield was 55%.

MS (FAB): 1201.3 (M+H)$^+$, 1223.3 (M+Na)$^+$.

68) 5'-MMTr-C$^{An}$-P(ONPE)-C$^{An}$-P(ONPE)-C$^{An}$-P(ONPE) (O-allyl)

Synthesis analogously to Example 17 from N-(N$^6$-anisoyl)cytosin-1-yl-acetyl-N-(4-methoxytriphenylmethoxy)ethylaminomethanephosphonic acid 2-(p-nitrophenyl)ethyl monester (triethylammonium salt) (Example 3) and 5'-HO-C$^{An}$-P(ONPE)-C$^{An}$-P(ONPE) (OAllyl) (Example 67). To purify the product, it was chromatographed on silica gel (EA/methanol/TEA 80:20:1). Yield 58%.

MS (FAB): 2046 (M+H)$^+$; 2068 (M+Na)$^+$.

69) 5'-MMTr-C$^{An}$-P(ONPE)-C$^{An}$-P(ONPE)-C$^{An}$-P(ONPE) (OH)

Synthesis analogously to Example 42 from 5'-MMTr-C$^{An}$-P(ONPE)-C$^{An}$-P(ONPE)-C$^{An}$-P(ONPE) (O-allyl) (Example 68). To purify the product, it was chromatographed on silica gel (EA/methanol/TEA 60:38:2). Yield: 66%.

MS (FAB): 2027 (M+Na)$^+$; 2049 (M+2Na—H)$^+$.

70) 5'-MMTr-C$^{An}$-P(ONPE)-C$^{An}$-P(ONPE)-C$^{An}$-P(ONPE)-C$^{An}$-P(ONPE)-C$^{An}$-P(ONPE)-C$^{An}$-P(ONPE)$_2$

Synthesis analogously to Example 17 from "5'-MMTr-C$^{An}$-P(ONPE)-C$^{An}$-P(ONPE)-C$^{An}$-P(ONPE) (OH)" (Example 69) and "5'-HO-C$^{An}$-P(ONPE)-C$^{An}$-P(ONPE)-C$^{An}$-P(ONPE)$_2$" (Example 32). To purify the product, it was chromatographed on silica gel (EA/methanol/TEA 70:30:2). Yield: 58%.

MS (FAB): 3892 (M+Na)$^+$; 3914 (M+2Na—H)$^+$.

71) 5'-MMTr-T-P(ONPE)-T-P(ONPE)-T-P(ONPE)-C$^{An}$-P(ONPE)-C$^{An}$-P(ONPE)-C$^{An}$-P(ONPE)$_2$

Synthesis analogously to Example 17 from "5'-MMTr-T-P(ONPE)-T-P-(ONPE)-T-P(ONPE) (OH)" (Example 45) and "5'-HO-C$^{An}$-P(ONPE)-C$^{An}$-P(ONPE)-C$^{An}$-P(ONPE)$_2$" (Example 32). To purify the product, it was chromatographed on silica gel (EA/methanol/TEA 60:40:2). The product fraction was evaporated in vacuo and purified by preparative HPLC (high pressure liquid chromatography): RP8 LiChrospher 60, water/acetonitrile: 1:1; 0.1% ammonium acetate; 1 ml/min) R$_f$=16.6 min MS (FAB): 3534 (M+Na)$^+$; 3556 (M+2Na—H)$^+$.

72) 5'-MMTr-T-P(OH)-T-P(OH)-T-P(OH)-C$^{An}$-P(OH)-C$^{An}$-P(OH)-C$^{An}$-P(OH)$_2$

Synthesis analogously to Example 40 from "5'-MMTr-T-P(ONPE)-T-P(ONPE)-T-P(ONPE)-C$^{An}$-P(ONPE)-C$^{An}$-P(ONPE)-C$^{An}$-P(ONPE)$_2$" (2 mg) (Example 71).

MS (ES–): 2466.4 (M–H).

73) 5'-MMTr-T-P(OH)-T-P(OH)-T-P(OH)-C-P(OH)-C-P(OH)-C-P(OH)$_2$

About 1 mg of "5'-MMTr-T-P(OH)-T-P-(OH)-T-P(OH)-C$^{An}$-P(OH)-C$^{An}$-P(OH)-C$^{An}$-P(OH)$_2$" (Example 72) was treated with 3 ml of 33% aqueous NH$_4$OH and stirred at room temperature for 24 h. The reaction mixture was evaporated in vacuo. Yield: about 0.6 mg (19 OD)

MS (ES–): 2064.5 (M–H)$^-$.

74) 5'-HO-T-P(OH)-T-P(OH)-C-P(OH)-C-P(OH)-C-P(OH)$_2$

8 OD of "5'-MMTr-T-P(OH)-T-P(OH)-T-P(OH)-C-P(OH)-C-P(OH)-C-P(OH)$_2$" (Example 73) were dissolved in 0.5 ml of water and added to a PolyPak™ (Glen Research, #60-1100-10). The MMTr group was removed following the instructions of the manufacturer (Glen Research User Guide). Yield: about 0.35 mg (11 OD).

MS (ES–): 1792.6 (M–H)$^-$.

75) 5'-MMTr-C$^{An}$-P(ONPE)-C$^{An}$-P(ONPE)-C$^{An}$-P(ONPE)-T-P(ONPE)-T-P(ONPE)-T-P(ONPE)$_2$

Synthesis analogously to Example 17 from "5'-MMTr-C$^{An}$-P(ONPE)-C$^{An}$-P(ONPE)-C$^{An}$-P(ONPE) (OH)" (Example 69) and "5'-HO-T-P-(ONPE)-T-P(ONPE)-T-P (OEt)$_2$" (Example 26). To purify the product, it was chromatographed on silica gel (EA/methanol/TEA 80:20:2, then 70:30:2). The product fraction was coevaporated with toluene, evaporated in vacuo and triturated with pentane. Yield: 48%.

MS (FAB): 3744 (M+Na)$^+$; 3766 (M+2Na–H)$^+$.

What is claimed is:

1. A method for the treatment of viruses comprising the step of administering to a patient in need of such treatment a composition comprising a compound of formula I

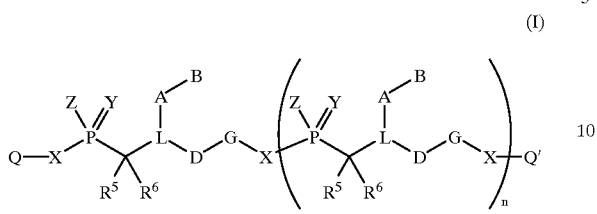

in which n is a number from zero to 100;

A independently of one another is a single bond, a methylene group or a group of formula IIa or IIb;

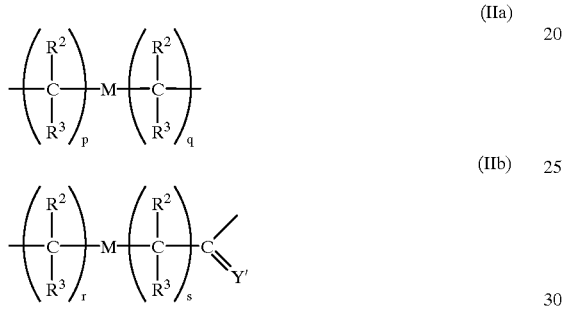

in which

M is single bond, —O—, —S— or —NR$^1$—, where R$^1$ is hydrogen or (C$_1$–C$_6$)-alkyl optionally substituted by hydroxyl, (C$_1$–C$_6$)-alkoxy, (C$_1$–C$_6$)-alkylthio or amino;

R$^2$ and R$^3$ independently of one another are hydrogen, hydroxyl, (C$_1$–C$_6$)-alkoxy, (C$_1$–C$_6$)-alkylthio, amino, halogen, or (C$_1$–C$_6$)-alkyl optionally substituted by hydroxyl, (C$_1$–C$_6$)-alkoxy or (C$_1$–C$_6$)-alkylthio;

p and q independently of one another are zero to 5; and r and s independently of one another are zero to 5;

B independently of one another is hydrogen, hydroxyl, (C$_1$–C$_{20}$)-alkyl, (C$_1$–C$_{20}$)-alkoxy, (C$_1$–C$_{20}$)-alkylthio, (C$_6$–C$_{20}$)-aryl-(C$_1$–C$_8$)-alkyl, (C$_6$–C$_{20}$)-aryl-(C$_1$–C$_6$)-alkoxy, (C$_6$–C$_{20}$)-aryl-(C$_1$–C$_6$)-alkylthio, an aromatic group or a heterocyclic group, wherein the alkyl, alkyl portion of alkoxy or alkylthio, aromatic or heterocyclic group is optionally substituted one or more times by hydroxyl, (C$_1$–C$_4$)-alkoxy, —NR$^9$R$^{10}$, oxo, —C(O)OR$^8$, —C(O)NR$^9$R$^{10}$, —CN, —F, —Cl, —Br, —NO$_2$, (C$_2$–C$_6$)-alkoxyalkyl, —S(O)$_m$R$^6$, —(C$_1$–C$_6$)-alkyl-S(O)$_m$R$^8$, —NHC(=NH)NHR$^8$, —C(=NH)NHR$^8$, NR$^9$C(=O)R$^8$, =NOR$^8$, NR$^9$C(=O)OR$^{10}$, —OC(=O)NR$^9$R$^{10}$, —NR$^9$C(=O)NR$^9$R$^{10}$, a natural nucleobase, an unnatural nucleobase or a reporter ligand, with the proviso that at least one B moiety is a nucleobase;

m is zero, 1 or 2;

or,

A-B independent of other A and B groups, can be a D- or L-amino acid condensed on via the carboxyl group or a peptide containing amino acids having a length of up to 5 amino acid residues, with the proviso that at least one B moiety is a nucleobase;

L independently of one another is N or R$^1$N$^+$, where R$^1$ is as defined above; and Y' is =O, =S, =CH$_2$, =C(CH$_3$)$_2$ or =NR$^1$, where R$^1$ is as defined above;

D and G each independently represent CR$^5$R$^6$ which can be the same or different;

R$^5$ and R$^6$ independently of one another are hydrogen, (C$_1$–C$_6$)-alkyl, (C$_6$–C$_{20}$)-aryl, (C$_6$–C$_{20}$)-aryl-(C$_1$–C$_6$)-alkyl, hydroxyl, (C$_1$–C$_6$)-alkoxy, (C$_1$–C$_6$)-alkylthio, wherein the alkyl, alkyl portion of alkoxy or alkylthio, or aryl group is optionally substituted by SR$^1$ or NR$^1$R$^{1'}$, where R$^1$ is as defined above and R$^{1'}$ independently of R$^1$ has the same meaning as R$^1$;

X independently of one another is —O—, —S— or —NR$^1$—, in which R$^1$ is as defined above;

Y independently of one another is =O or =S;

Z independently of one another is —OR$^8$, —NR$^9$R$^{10}$ or X'Q", where X' is defined as X above and Q" is defined as Q below;

R$^8$ is hydrogen, (C$_1$–C$_{18}$)-alkyl, (C$_2$–C$_{18}$)-alkenyl, (C$_3$–C$_{18}$)-alkynyl, (C$_6$–C$_{12}$)-aryl, (C$_6$–C$_{12}$)-aryl-(C$_1$–C$_6$)-alkyl, wherein alkyl is optionally substituted one or more times by hydroxyl, (C$_1$–C$_4$)-alkoxy, F, Cl or Br and wherein aryl is optionally substituted 1–3 times by hydroxyl, (C$_1$–C$_4$)-alkoxy, (C$_1$–C$_4$)-alkyl, F, Cl, Br, NO$_2$, —NR$^9$R$^{10}$, —C(O)OH, —C(O)O—(C$_1$–C$_6$)-alkyl or —C(O)NR$^9$R$^{10}$;

R$^9$ and R$^{10}$ independently of one another are hydrogen, (C$_1$–C$_{18}$)-alkyl, (C$_2$–C$_{18}$)-alkenyl, (C$_3$–C$_{18}$)-alkynyl, (C$_6$–C$_{12}$)-aryl, (C$_6$–C$_{12}$)-aryl-(C$_1$–C$_6$)-alkyl, where alkyl is optionally substituted one or more times by hydroxyl, (C$_1$–C$_4$)-alkoxy, F, Cl or Br; or R$^9$ and R$^{10}$ form a 4 to 7-membered ring together with the N atom in —NR$^9$R$^{10}$;

Q and Q' independently of one another are R$^8$, modified or unmodified oligonucleotides or conjugates which a) favorably affect the properties of antisense oligonucleotides, b) affect the properties of triple helix-forming oligonucleotides, c) serve as a label of a DNA probe, or d) during the hybridization of the oligonucleotide analog to the target nucleic acid, attack the target nucleic acid with binding or cross-linking; or Q and Q' alone or together are a single bond in a cyclic molecule; or Q and Q', when neither is hydrogen, can be linked together to form a cyclic molecule;

wherein said compound comprises at least 6 nucleotides; together with a physiologically acceptable excipient.

2. A method for the treatment of cancer or restenosis comprising the step of administering to a patient in need of such treatment an effective amount of a composition comprising a compound of formula I

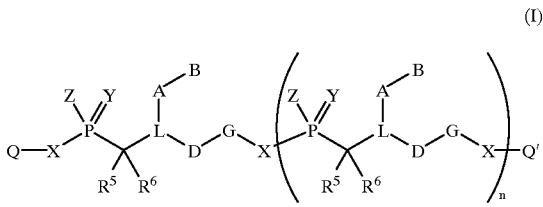

in which n is a number from zero to 100;

A independently of one another is a single bond, a methylene group or a group of formula IIa or IIb;

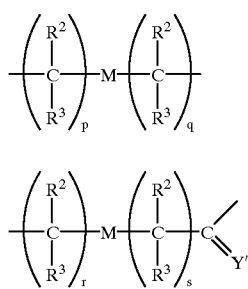

(IIa)

(IIb)

in which

M is a single bond, —O—, —S— or —NR$^1$—, where R$^1$ is hydrogen or $(C_1-C_6)$-alkyl optionally substituted by hydroxyl, $(C_1-C_6)$-alkoxy, $(C_1-C_6)$-alkylthio or amino;

R$^2$ and R$^3$ independently of one another are hydrogen, hydroxyl, $(C_1-C_6)$-alkoxy, $(C_1-C_6)$-alkylthio, amino, halogen, or $(C_1-C_6)$-alkyl optionally substituted by hydroxyl, $(C_1-C_6)$-alkoxy or $(C_1-C_6)$-alkylthio;

p and q independently of one another are zero to 5; and r and s independently of one another are zero to 5;

B independently of one another is hydrogen, hydroxyl, $(C_1-C_{20})$-alkyl, $(C_1-C_{20})$-alkoxy, $(C_1-C_{20})$-alkylthio, $(C_6-C_{20})$-aryl-$(C_1-C_6)$-alkyl, $(C_6-C_{20})$-aryl-$(C_1-C_6)$-alkoxy, $(C_6-C_{20})$-aryl-$(C_1-C_6)$-alkylthio, an aromatic group or a heterocyclic group, wherein the alkyl, alkyl portion of alkoxy or alkylthio, aromatic or heterocyclic group is optionally substituted one or more times by hydroxyl, $(C_1-C_4)$-alkoxy, —NR$^9$R$^{10}$, oxo, —C(O)OR$^8$, —C(O)NR$^9$R$^{10}$, —CN, —F, —Cl, —Br, —NO$_2$, $(C_2-C_6)$-alkoxyalkyl, —S(O)$_m$R$^8$, —$(C_1-C_6)$-alkyl-S(O)$_m$R$^8$, —NHC(=NH)NHR$^8$, —C(=NH)NHR$^8$, NR$^9$C(=O)R$^8$, =NOR$^8$, NR$^9$C(=O)OR$^{10}$, —OC(=O)NR$^9$R$^{10}$, —NR$^9$C(=O)NR$^9$R$^{10}$, a natural nucleobase, an unnatural nucleobase or a reporter ligand, with the proviso that at least one B moiety is a nucleobase;

m is zero, 1 or 2;

or

A-B independent of other A and B groups, can be a D- or L-amino acid condensed on via the carboxy group or a peptide containing amino acids having a length of up to 5 amino acid residues, with the proviso that at least one B moiety is a nucleobase;

L independently of one another is N or R$^1$N$^+$, where R$^1$ is as defined above; and Y' is =O, =S, =CH$_2$, =C(CH$_3$)$_2$ or =NR$^1$, where R$^1$ is as defined above;

D and G each independently represent CR$^5$R$^6$ which can be the same or different;

R$^5$ and R$^6$ independently of one another are hydrogen, $(C_1-C_6)$-alkyl, $(C_6-C_{20})$-aryl, $(C_6-C_{20})$-aryl-$(C_1-C_6)$-alkyl, hydroxyl, $(C_1-C_6)$-alkoxy, $(C_1-C_6)$-alkylthio, wherein the alkyl, alkyl portion of alkoxy or alkylthio, or aryl group is optionally substituted by SR$^1$ or NR$^1$R$^{1'}$, where R$^1$ is as defined above and R$^{1'}$ independently of R$^1$ has the same meaning as R$^1$;

X independently of one another is —O—, —S— or —NR$^1$—, in which R$^1$ is as defined above;

Y independently of one another is =O or =S;

Z independently of one another is —OR$^8$, —NR$^9$R$^{10}$ or X'Q", where X' is defined as X above and Q" is defined as Q below;

R$^8$ is hydrogen, $(C_1-C_{18})$-alkyl, $(C_2-C_{18})$-alkenyl, $(C_3-C_{18})$-alkynyl, $(C_6-C_{12})$-aryl, $(C_6-C_{12})$-aryl-$(C_1-C_6)$-alkyl, wherein alkyl is optionally substituted one or more times by hydroxyl, $(C_1-C_4)$-alkoxy, F, Cl or Br and wherein aryl is optionally substituted 1–3 times by hydroxyl, $(C_1-C_4)$-alkoxy, $(C_1-C_4)$-alkyl, F, Cl, Br, NO$_2$, —NR$^9$R$^{10}$, —C(O)OH, —C(O)O—$(C_1-C_6)$-alkyl or —C(O)NR$^9$R$^{10}$;

R$^9$ and R$^{10}$ independently of one another are hydrogen, $(C_1-C_{18})$-alkyl, $(C_2-C_{18})$-alkenyl, $(C_3-C_{18})$-alkynyl, $(C_8-C_{12})$-aryl, $(C_6-C_{12})$-aryl-$(C_1-C_6)$-alkyl, where alkyl is optionally substituted one or more times by hydroxyl, $(C_1-C_4)$-alkoxy, F, Cl or Br; or R$^9$ and R$^{10}$ form a 4 to 7-membered ring together with the N atom in —NR$^9$R$^{10}$;

Q and Q' independently of one another are R$^8$, modified or unmodified oligonucleotides or conjugates which a) favorably affect the properties of antisense oligonucleotides, b) affect the properties of triple helix-forming oligonucleotides, c) serve as a label of a DNA probe, or d) during the hybridization of the oligonucleotide analog to the target nucleic acid, attack the target nucleic acid with binding or cross-linking; or Q and Q' alone or together are a single bond in a cyclic molecule; or Q and Q', when neither is hydrogen, can be linked together to form a cyclic molecule;

wherein said compound comprises at least 6 nucleotides;

together with a physiologically acceptable excipient.

3. The method according to claim 1, wherein said virus is HIV, HSV-1, HSV-2, influenza, RSV, hepatitis B, or papilloma virus.

4. A method for the treatment of medical conditions resulting from integrins or cell-cell adhesion receptors comprising administering to a patient in need of such treatment an effective amount of a composition comprising a compound of formula I

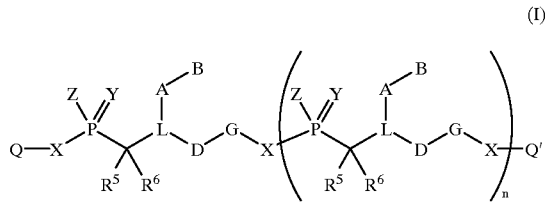

(I)

in which n is a number from zero to 100;

A independently of one another is a single bond, a methylene group or a group of formula IIa or IIb;

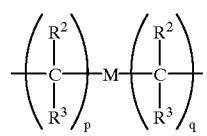

(IIa)

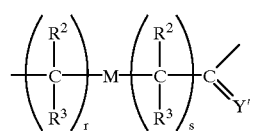

(IIb)

in which

M is a single bond, —O—, —S— or —NR$^1$—, where R$^1$ is hydrogen or $(C_1-C_6)$-alkyl optionally substituted by hydroxyl, $(C_1-C_6)$-alkoxy, $(C_1-C_6)$-alkylthio or amino;

$R^2$ and $R^3$ independently of one another are hydrogen, hydroxyl, $(C_1-C_6)$-alkoxy, $(C_1-C_6)$-alkylthio, amino, halogen, or $(C_1-C_6)$-alkyl optionally substituted by hydroxyl, $(C_1-C_6)$-alkoxy or $(C_1-C_6)$-alkylthio;

p and q independently of one another are zero to 5; and r and s independently of one another are zero to 5;

B independently of one another is hydrogen, hydroxyl, $(C_1-C_{20})$-alkyl, $(C_1-C_{20})$-alkoxy, $(C_1-C_{20})$-alkylthio, $(C_6-C_{20})$-aryl-$(C_1-C_6)$-alkyl, $(C_6-C_{20})$-aryl-$(C_1-C_8)$-alkoxy, $(C_6-C_{20})$-aryl-$(C_1-C_6)$-alkylthio, an aromatic group or a heterocyclic group, wherein the alkyl, alkyl portion of alkoxy or alkylthio, aromatic or heterocyclic group is optionally substituted one or more time by hydroxyl, $(C_1-C_4)$-alkoxy, —$NR^9R^{10}$, oxo, —C(O)$OR^8$, —C(O)$NR^9R^{10}$, —CN, —F, —Cl, —Br, —$NO_2$, $(C_2-C_6)$-alkoxyalkyl, —$S(O)_mR^8$, —$(C_1-C_6)$-alkyl-S$(O)_mR^8$, —NHC(=NH)$NHR^8$, —C(=NH)$NHR^8$, $NR^9C(=O)R^8$, =$NOR^8$, $NR^9C(=O)OR^{10}$, —OC(=O)$NR^9R^{10}$, —$NR^9C(=O)NR^9R^{10}$, a natural nucleobase, an unnatural nucleobase or a reporter ligand, with the proviso that at least one B moiety is a nucleobase;

m is zero, 1 or 2;

or,

A-B independent of other A and B groups, can be a D- or L-amino acid condensed on via the carboxyl group or a peptide containing amino acids having a length of up to 5 amino acid residues, with the proviso that at least one B moiety is a nucleobase;

L independently of one another is N or $R^1N^+$, where $R^1$ is as defined above; and Y' is =O, =S, =$CH_2$, =$C(CH_3)_2$ or =$NR^1$, where $R^1$ is as defined above;

D and G each independently represent $CR^5R^6$ which can be the same or different;

$R^5$ and $R^6$ independently of one another are hydrogen, $(C_1-C_6)$-alkyl, $(C_6-C_{20})$-aryl, $(C_6-C_{20})$-aryl-$(C_1-C_6)$-alkyl, hydroxyl, $(C_1-C_6)$-alkoxy, $(C_1-C_6)$-alkylthio, wherein the alkyl, alkyl portion of alkoxy or alkylthio, or aryl group is optionally substituted by $SR^1$ or $NR^1R^{1'}$, where $R^1$ is as defined above and $R^{1'}$ independently of $R^1$ has the same meaning as $R^1$;

X independently of one another is —O—, —S— or —$NR^1$—, in which $R^1$ is as defined above;

Y independently of one another is =O or =S;

Z independently of one another is —$OR^8$, —$NR^9R^{10}$ or X'Q", where W' is defined as X above and Q" is defined as Q below;

$R^8$ is hydrogen, $(C_1-C_{18})$-alkyl, $(C_2-C_{18})$-alkenyl, $(C_3-C_{18})$-alkynyl, $(C_6-C_{12})$-aryl, $(C_6-C_{12})$-aryl-$(C_1-C_6)$-alkyl, wherein alkyl is optionally substituted one or more times by hydroxyl, $(C_1-C_4)$-alkoxy, F, Cl or Br and wherein aryl is optionally substituted 1–3 times by hydroxyl, $(C_1-C_4)$-alkoxy, $(C_1-C_4)$-alkyl, F, Cl, Br, $NO_2$, —$NR^9R^{10}$, —C(O)OH, —C(O)O—$(C_1-C_6)$-alkyl or —C(O)$NR^9R^{10}$;

$R^9$ and $R^{10}$ independently of one another are hydrogen, $(C_1-C_{18})$-alkyl, $(C_2-C_{18})$-alkenyl, $(C_3-C_{18})$-alkynyl, $(C_6-C_{12})$-aryl, $(C_6-C_{12})$-aryl-$(C_1-C_6)$-alkyl, where alkyl is optionally substituted one or more times by hydroxyl, $(C_1-C_4)$-alkoxy, F, Cl or Br; or $R^9$ and $R^{10}$ form a 4 to 7-membered ring together with the N atom in —$NR^9R^{10}$;

Q and Q' independently of one another are $R^8$, modified or unmodified oligonucleotides or conjugates which a) favorably affect the properties of antisense oligonucleotides, b) affect the properties of triple helix-forming oligonucleotides, c) serve as a label of a DNA probe, or d) during the hybridization of the oligonucleotide analog to the target nucleic acid, attack the target nucleic acid with binding or cross-linking; or Q and Q' alone or together are a single bond in a cyclic molecule; or Q and Q', when neither is hydrogen, can be linked together to form a cyclic molecule;

wherein said compound comprises at least 6 nucleotides; together with a physiologically acceptable excipient.

5. A method for the treatment of medical conditions induced by growth factors comprising the step of administering to a patient in need of such treatment an effective amount of a composition comprising a compound of formula I

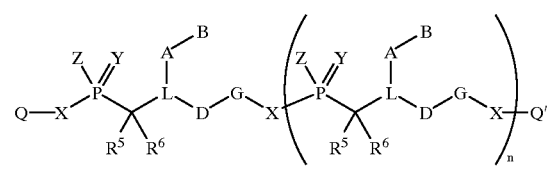

(I)

in which n is a number from zero to 100;

A independently of one another is a single bond, a methylene group or a group of formula IIa or IIb;

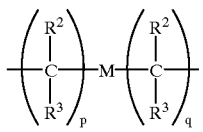

(IIa)

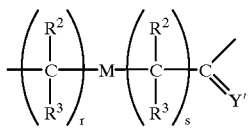

(IIb)

in which

M is a single bond, —O—, —S— or —$NR^1$—, where $R^1$ is hydrogen or $(C_1-C_6)$-alkyl optionally substituted by hydroxyl, $(C_1-C_6)$-alkoxy, $(C_1-C_6)$-alkylthio or amino;

$R^2$ and $R^3$ independently of one another are hydrogen, hydroxyl, $(C_1-C_6)$-alkoxy, $(C_1-C_6)$-alkylthio, amino, halogen, or $(C_1-C_6)$-alkyl optionally substituted by hydroxyl, $(C_1-C_6)$-alkoxy or $(C_1-C_6)$-alkylthio;

p and q independently of one another are zero to 5; and r and s independently of one another are zero to 5;

B independently of one another is hydrogen, hydroxyl, $(C_1-C_{20})$-alkyl, $(C_1-C_{20})$-alkoxy, $(C_1-C_{20})$-alkylthio, $(C_6-C_{20})$-aryl-$(C_1-C_6)$-alkyl, $(C_6-C_{20})$-aryl-$(C_1-C_6)$-alkoxy, $(C_6-C_{20})$-aryl-$(C_1-C_6)$-alkylthio, an aromatic group or a heterocyclic group, wherein the alkyl, alkyl portion of alkoxy or alkylthio, aromatic or heterocyclic group is optionally substituted one or more times by hydroxyl, $(C_1-C_4)$-alkoxy, —$NR^9R^{10}$, oxo, —C(O)$OR^8$, —C(O)$NR^9R^{10}$, —CN, —F, —Cl, —Br, —$NO_2$, $(C_2-C_5)$-alkoxyalkyl, —$S(O)_mR^8$, —$(C_1-C_6)$-alkyl-S$(O)_mR^8$, —NHC(=NH)$NHR^8$, —C(=NH)$NHR^8$, $NR^9C(=O)R^8$, =$NOR^8$, $NR^9C(=O)OR^{10}$, —OC(=O)$NR^9R^{10}$, —$NR^9C(=O)NR^9R^{10}$, a natural nucleobase, an unnatural nucleobase or a reporter ligand, with the proviso that at least one B moiety is a nucleobase;

m is zero, 1 or 2;

or,

A-B independent of other A and B groups, can be a D- or L-amino acid condensed on via the carboxyl group or a peptide containing amino acids having a length of up to 5 amino acid residues, with the proviso that at least one B moiety is a nucleobase;

L independently of one another is N or $R^1N^+$, where $R^1$ is as defined above; and Y' is =O, =S, =CH$_2$, =C(CH$_3$)$_2$ or =NR$^1$, where $R^1$ is as defined above;

D and G each independently represent $CR^5R^6$ which can be the same or different;

$R^5$ and $R^6$ independently of one another are hydrogen, $(C_1-C_6)$-alkyl, $(C_6-C_{20})$-aryl, $(C_6-C_{20})$-aryl-$(C_1-C_6)$-alkyl, hydroxyl, $(C_1-C_6)$-alkoxy, $(C_1-C_6)$-alkylthio, wherein the alkyl, alkyl portion of alkoxy or alkylthio, or aryl group is optionally substituted by $SR^1$ or $NR^1R^{1'}$, where $R^1$ is as defined above and $R^{1'}$ independently of $R^1$ has the same meaning as $R^1$;

X independently of one another is —O—, —S— or —NR$^1$—, in which $R^1$ is as defined above;

Y independently of one another is =O or =S;

Z independently of one another is —OR$^8$, —NR$^9$R$^{10}$ or X'Q", where X' is defined as X above and Q" is defined as Q below;

$R^8$ is hydrogen, $(C_1-C_{18})$-alkyl, $(C_2-C_{18})$-alkenyl, $(C_3-C_{18})$-alkynyl, $(C_6-C_{12})$-aryl, $(C_6-C_{12})$-aryl-$(C_1-C_6)$-alkyl, wherein alkyl is optionally substituted one or more times by hydroxyl, $(C_1-C_4)$-alkoxy, F, Cl or Br and wherein aryl is optionally substituted 1–3 times by hydroxyl, $(C_1-C_4)$-alkoxy, $(C_1-C_4)$-alkyl, F, Cl, Br, NO$_2$, —NR$^9$R$^{10}$, —C(O)OH, —C(O)O—$(C_1-C_6)$-alkyl or —C(O)NR$^9$R$^{10}$;

$R^9$ and $R^{10}$ independently of one another are hydrogen, $(C_1-C_{18})$-alkyl, $(C_2-C_{18})$-alkenyl, $(C_3-C_{18})$-alkynyl, $(C_6-C_{12})$-aryl, $(C_6-C_{12})$-aryl-$(C_1-C_6)$-alkyl, where alkyl is optionally substituted one or more time by hydroxy, $(C_1-C_4)$-alkoxy, F, Cl or Br; or $R^9$ and $R^{10}$ form a 4 to 7-membered ring together with the N atom in —NR$^9$R$^{10}$;

Q and Q' independently of one another are $R^8$, modified or unmodified oligonucleotides or conjugates which a) favorably affect the properties of antisense oligonucleotides, b) affect the properties of triple helix-forming oligonucleotides, c) serve as a label of a DNA probe, or d) during the hybridization of the oligonucleotide analog to the target nucleic acid, attack the target nucleic acid with binding or cross-linking; or Q and Q' alone or together are a single bond in a cyclic molecule; or Q and Q', when neither is hydrogen, can be linked together to form a cyclic molecule;

wherein said compound comprises at least 6 nucleotides;

together with a physiologically acceptable excipient.

6. The method according to claim 5, wherein said growth factor is TNF-α.

* * * * *

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) ANTISENSE: yes (ix) FEATURE:
         (A) NAME/KEY: exon
         (B) LOCATION: 1..20

(xi) SEQUENCE DESCRIPTION: SEQ ID NO: 1:

ACACCCAATT CTGAAAATGG                                            20

(2) INFORMATION FOR SEQ ID NO: 2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) ANTISENSE: yes (ix) FEATURE:
         (A) NAME/KEY: exon
         (B) LOCATION: 1..20

(xi) SEQUENCE DESCRIPTION: SEQ ID NO: 2:

AGGTCCCTGT TCGGGCGCCA                                            20

(2) INFORMATION FOR SEQ ID NO: 3:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(iii) ANTISENSE: yes (ix) FEATURE:
         (A) NAME/KEY: exon
         (B) LOCATION: 1..28

(xi) SEQUENCE DESCRIPTION: SEQ ID NO: 3:

GTCGACACCC AATTCTGAAA ATGGATAA                                   28

(2) INFORMATION FOR SEQ ID NO: 4:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

-continued (iii) ANTISENSE: yes (ix) FEATURE:
              (A) NAME/KEY: exon
              (B) LOCATION: 1..25

(xi) SEQUENCE DESCRIPTION: SEQ ID NO: 4:

GCTATGTCGA CACCCAATTC TGAAA                                           25

(2) INFORMATION FOR SEQ ID NO: 5:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (genomic)

(iii) ANTISENSE: yes (ix) FEATURE:
              (A) NAME/KEY: exon
              (B) LOCATION: 1..26

(xi) SEQUENCE DESCRIPTION: SEQ ID NO: 5:

GTCGCTGTCT CCGCTTCTTC TTCCTG                                          26

(2) INFORMATION FOR SEQ ID NO: 6:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (genomic)

(iii) ANTISENSE: yes (ix) FEATURE:
              (A) NAME/KEY: exon
              (B) LOCATION: 1..27

(xi) SEQUENCE DESCRIPTION: SEQ ID NO: 6:

GTCTCCGCTT CTTCTTCCTG CCATAGG                                         27

(2) INFORMATION FOR SEQ ID NO: 7:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) ANTISENSE: yes (ix) FEATURE:
              (A) NAME/KEY: exon
              (B) LOCATION: 1..20

(xi) SEQUENCE DESCRIPTION: SEQ ID NO: 7:

GCGGGGCTCC ATGGGGTCG                                                  20

(2) INFORMATION FOR SEQ ID NO: 8:

(i) SEQUENCE CHARACTERISTICS:
              (A) LENGTH: 15 base pairs
              (B) TYPE: nucleic acid (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..15

(xi) SEQUENCE DESCRIPTION: SEQ ID NO: 8:

CAGCTGCAAC CCAGC                                                        15

(2) INFORMATION FOR SEQ ID NO: 9:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..21

(xi) SEQUENCE DESCRIPTION: SEQ ID NO: 9:

GGCTGCTGGA GCGGGGCACA C                                                 21

(2) INFORMATION FOR SEQ ID NO: 10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..15

(xi) SEQUENCE DESCRIPTION: SEQ ID NO: 10:

AACGTTGAGG GGCAT                                                        15

(2) INFORMATION FOR SEQ ID NO: 11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..18

(xi) SEQUENCE DESCRIPTION: SEQ ID NO: 11:

GTGCCGGGGT CTTCGGGC                                                     18

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..21

(xi) SEQUENCE DESCRIPTION: SEQ ID NO: 12:

GGAGAACATC ATGGTCGAAA G                                  21

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..22

(xi) SEQUENCE DESCRIPTION: SEQ ID NO: 13:

CCCGAGAACA TCATGGTCGA AG                               22

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..20

(xi) SEQUENCE DESCRIPTION: SEQ ID NO: 14:

GGGGAAAGCC CGGCAAGGGG                                   20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..20

```
    (xi) SEQUENCE DESCRIPTION: SEQ ID NO: 15:

CACCCGCCTT GGCCTCCCAC                                                   20

(2) INFORMATION FOR SEQ ID NO: 16

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..18

(xi) SEQUENCE DESCRIPTION: SEQ ID NO: 16:

GGGACTCCGG CGCAGCGC                                                     18

(2) INFORMATION FOR SEQ ID NO: 17

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..20

(xi) SEQUENCE DESCRIPTION: SEQ ID NO: 17:

GGCAAACTTT CTTTTCCTCC                                                   20

(2) INFORMATION FOR SEQ ID NO: 18

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..19

(xi) SEQUENCE DESCRIPTION: SEQ ID NO: 18:

GGGAAGGAGG AGGATGAGG                                                    19

(2) INFORMATION FOR SEQ ID NO: 19

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes
```

```
        (ix) FEATURE:
              (A) NAME/KEY: exon
              (B) LOCATION: 1..21

(xi) SEQUENCE DESCRIPTION: SEQ ID NO: 19:

GGCAGTCATC CAGCTTCGGA G                                              21

(2) INFORMATION FOR SEQ ID NO: 20

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: DNA (genomic)

(iii) ANTISENSE: yes (ix) FEATURE:
              (A) NAME/KEY: exon
              (B) LOCATION: 1..18

(xi) SEQUENCE DESCRIPTION: SEQ ID NO: 20:

GCAGTAAGCA TCCATATC                                                  18

(2) INFORMATION FOR SEQ ID NO: 21

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) ANTISENSE: yes (ix) FEATURE:
              (A) NAME/KEY: exon
              (B) LOCATION: 1..20

(xi) SEQUENCE DESCRIPTION: SEQ ID NO: 21:

CCCCCACCAC TTCCCCTCTC                                                20

(2) INFORMATION FOR SEQ ID NO: 22

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) ANTISENSE: yes (ix) FEATURE:
              (A) NAME/KEY: exon
              (B) LOCATION: 1..20

(xi) SEQUENCE DESCRIPTION: SEQ ID NO: 22:

CTCCCCCACC ACTTCCCCTC                                                20

(2) INFORMATION FOR SEQ ID NO: 23

(i) SEQUENCE CHARACTERISTICS:
              (A) LENGTH: 19 base pairs
              (B) TYPE: nucleic acid
              (C) STRANDEDNESS: single
              (D) TOPOLOGY: linear
```

```
     (ii) MOLECULE TYPE: DNA (genomic)

(iii) ANTISENSE: yes (ix) FEATURE:
          (A) NAME/KEY: exon
          (B) LOCATION: 1..19

(xi) SEQUENCE DESCRIPTION: SEQ ID NO: 23:

GCTGGGAGCC ATAGCGAGG                                                19

(2) INFORMATION FOR SEQ ID NO: 24

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) ANTISENSE: yes (ix) FEATURE:
          (A) NAME/KEY: exon
          (B) LOCATION: 1..21

(xi) SEQUENCE DESCRIPTION: SEQ ID NO: 24:

ACTGCTGCCT CTTGTCTCAG G                                             21

(2) INFORMATION FOR SEQ ID NO: 25

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(iii) ANTISENSE: yes (ix) FEATURE:
          (A) NAME/KEY: exon
          (B) LOCATION: 1..22

(xi) SEQUENCE DESCRIPTION: SEQ ID NO: 25:

CAATCAATGA CTTCAAGAGT TC                                            22

(2) INFORMATION FOR SEQ ID NO: 26

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iii) ANTISENSE: yes (ix) FEATURE:
          (A) NAME/KEY: exon
          (B) LOCATION: 1..19

(xi) SEQUENCE DESCRIPTION: SEQ ID NO: 26:

GGTCCCTGTT CGGGCGCCA                                                19
```

(2) INFORMATION FOR SEQ ID NO: 27

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..17

(xi) SEQUENCE DESCRIPTION: SEQ ID NO: 27:

GTGCCGGGGT CTTCGGG        17

(2) INFORMATION FOR SEQ ID NO: 28

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..17

(xi) SEQUENCE DESCRIPTION: SEQ ID NO: 28:

GGAGGATGCT GAGGAGG        17

(2) INFORMATION FOR SEQ ID NO: 29

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
        (A) NAME/KEY: exon
        (B) LOCATION: 1..14

(xi) SEQUENCE DESCRIPTION: SEQ ID NO: 29:

GGAGGATGCT GAGG        14

(2) INFORMATION FOR SEQ ID NO: 30

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..19

(xi) SEQUENCE DESCRIPTION: SEQ ID NO: 30:

CAGGAGGATG CTGAGGAGG                                                                 19

(2) INFORMATION FOR SEQ ID NO: 31

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..15

(xi) SEQUENCE DESCRIPTION: SEQ ID NO: 31:

GGCTGCCATG GTCCC                                                                     15

(2) INFORMATION FOR SEQ ID NO: 32

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..20

(xi) SEQUENCE DESCRIPTION: SEQ ID NO: 32:

TCATGGTGTC CTTTGCAGCC                                                                20

(2) INFORMATION FOR SEQ ID NO: 33

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) ANTISENSE: yes (ix) FEATURE:
            (A) NAME/KEY: exon
            (B) LOCATION: 1..18

(xi) SEQUENCE DESCRIPTION: SEQ ID NO: 33:

TCATGGTGTC CTTTGCAG                                                                  18